United States Patent [19]

Michaely et al.

[11] Patent Number: 4,780,127
[45] Date of Patent: Oct. 25, 1988

[54] CERTAIN 2-(SUBSTITUTED BENZOYL)-1,3-CYCLOHEXANEDIONES AND THEIR USE AS HERBICIDES

[75] Inventors: William J. Michaely, El Cerrito; Gary W. Kraatz, San Jose, both of Calif.

[73] Assignee: Stauffer Chemical Company, Westport, Conn.

[21] Appl. No.: 880,370

[22] Filed: Jun. 30, 1986

Related U.S. Application Data

[63] Continuation-in-part of Ser. No. 772,593, Sep. 5, 1985, abandoned, which is a continuation-in-part of Ser. No. 634,408, Jul. 31, 1984, abandoned, which is a continuation-in-part of Ser. No. 587,331, Mar. 7, 1984, abandoned, which is a continuation-in-part of Ser. No. 532,869, Sep. 16, 1983, abandoned, which is a continuation-in-part of Ser. No. 464,251, Feb. 9, 1983, abandoned, which is a continuation-in-part of Ser. No. 361,658, Mar. 25, 1982, abandoned.

[51] Int. Cl.$^4$ ............... A01N 41/00; C07C 101/78; C07C 103/20; C07C 121/50
[52] U.S. Cl. ............................... 71/103; 71/98; 71/105; 71/107; 71/111; 71/118; 71/123; 558/415; 560/12; 560/13; 560/18; 560/21; 560/24; 560/25; 560/27; 560/36; 560/52; 564/85; 564/86; 564/87; 564/88
[58] Field of Search ............... 71/103, 105, 107, 111, 71/118, 123, 98; 560/12, 13, 18, 21, 24, 25, 27, 36, 52; 568/306, 42, 43, 27, 28, 30, 31, 25, 331; 564/85, 86, 87, 88, 152, 153, 154, 155, 162, 163, 165, 166, 167, 306; 558/415

[56] References Cited
U.S. PATENT DOCUMENTS
4,209,532 6/1980 Wheeler ........................... 514/681
4,350,705 9/1982 Hamano et al. ................... 514/453

OTHER PUBLICATIONS
Akhrem et al.; *Synthesis*, International Journal of Methods in Synthetic Organic Chemistry, No. 12, pp. 925–927, (Dec. 1978).

Primary Examiner—Werren B. Lone
Assistant Examiner—Vera C. Clarke
Attorney, Agent, or Firm—Edwin H. Baker

[57] ABSTRACT

Compounds of the formula

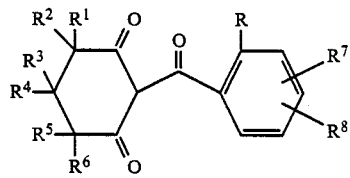

wherein R is halogen, $C_1$–$C_4$ alkoxy, $C_1$–$C_4$ alkyl, $C_1$–$C_4$ haloalkyl, cyano, nitro, $S(O)_nR$ wherein R is $C_1$–$C_4$ alkyl and n is the integer 0, 1 or 2; and $R^2$ through $R^8$ are hydrogen or certain substituents, their salts, herbicidal compositions containing the compound or salts and the herbicidal use thereof.

64 Claims, No Drawings

CERTAIN 2-(SUBSTITUTED BENZOYL)-1,3-CYCLOHEXANEDIONES AND THEIR USE AS HERBICIDES

CROSS-REFERENCE TO RELATED APPLICATIONS

This application is a continuation-in-part application of Ser. No. 772,593, filed Sept. 5, 1985 now abandoned; which in turn is a continuation-in-part application of Ser. No. 634,408, filed July 31, 1984, now abandoned; which in turn is a continuation-in-part application of Ser. No. 587,331, filed Mar. 7, 1984, now abandoned; which in turn is a continuation-inpart of application Ser. No. 532,869, filed Sept. 16, 1983, now abandoned; which in turn is a continuation-in-part application of Ser. No. 464,251, filed Feb. 9, 1983, now abandoned; which in turn is a continuation-in-part application of Ser. No. 361,658, filed Mar. 25, 1982, now abandoned.

Applicants specifically incorporate by reference the contents of the above listed U.S. patent applications.

BACKGROUND OF THE INVENTION

Compounds having the structural formula

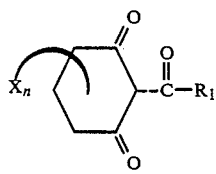

wherein X can be alkyl, n can be 0, 1, or 2, and $R_1$ can be phenyl or substituted phenyl are described in Japanese Patent Application No. 84632-1974 as being intermediates for the preparation of herbicidal compounds of the formula

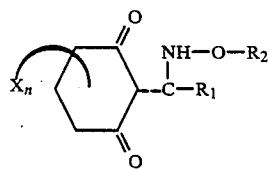

wherein $R_1$, X, and n are as defined above and $R_2$ is alkyl, alkenyl, or alkynyl. Specifically taught herbicidal compounds of this latter group are those where n is 2, X is 5,5-dimethyl, $R_2$ is allyl and $R_1$ is phenyl, 4-chlorophenyl or 4-methoxyphenyl.

The precursor intermediates for these three specifically taught compounds have no or almost no herbicidal activity.

DESCRIPTION OF THE INVENTION

Embodiment A of this invention relates to certain novel 2-(2-substituted benzoyl)-cyclohexane-1,3-diones as herbicides. The compounds of this embodiment have the following structural formula

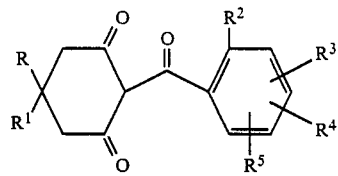

wherein
R and $R^1$ are hydrogen, $C_1$–$C_4$ alkyl, preferably methyl or isopropyl, $R^aOC(O)$—, where $R^a$ is $C_1$–$C_4$ alkyl; most preferably R and $R^1$ are hydrogen;

$R^2$ is chlorine, bromine, iodine or $C_1$–$C_4$ alkoxy, preferably methoxy; most preferably $R_2$ is chlorine, bromine or methoxy;

$R^3$, $R^4$ and $R^5$ independently are hydrogen or an aliphatic group, preferably: (1) hydrogen; (2) halogen, preferably chlorine or bromine; (3) $C_1$–$C_4$ alkyl, preferably methyl; (4) $C_1$–$C_4$ alkoxy, preferably methoxy; (5) trifluoromethoxy; (6) cyano; (7) nitro; (8) $C_1$–$C_4$ haloalkyl, more preferably trifluoromethyl; (9) $R^bSO_n$— wherein $R^b$ is $C_1$–$C_4$ alkyl, preferably methyl, $C_1$–$C_4$ haloalkyl, phenyl, benzyl, —$NR^dR^e$ wherein $R^d$ and $R^e$ independently are hydrogen or $C_1$–$C_4$ alkyl; and n is the integer 0, 1 or 2, preferably 2;

 (10)

$R^cCNR^j$— wherein $R^c$ is $C_1$–$C_4$ alkyl and $R^j$ is hydrogen or $C_1$–$C_4$ alkyl, preferably methyl; (11) $R^fC(O)$ wherein $R^f$ is hydrogen, $C_1$–$C_4$ alkyl, $C_1$–$C_4$ haloalkyl, $C_1$–$C_4$ alkoxy; (12) —$NR^gR^h$ wherein $R^g$ and $R^h$ independently are hydrogen or $C_1$–$C_4$ alkyl; or less preferably (13) $R^3$ and $R^4$ together can form a ring structure with two adjacent carbon atoms of the phenyl ring.

$R^3$ and $R^4$ can also be (14) $C_3$–$C_5$ alkenyloxy (thio) optionally substituted, preferably with halogen or (15) $C_3$–$C_5$ alkynyloxy (thio), optionally substituted, preferably with halogen.

Most preferably, $R^3$ is chlorine, hydrogen, dimethylamino or methoxy. Preferably, $R^4$ is hydrogen, chlorine, nitro, $SO_2CH_3$, $SO_2N(CH_3)_2$ or trifluoromethyl. Preferably, $R^5$ is hydrogen.

Embodiment A' of this invention is an herbicidal composition comprising an herbicidally active 2-benzoyl-1,3-cyclohexanedione and an inert carrier threfor. Preferably, the 2-position of the benzoyl moiety is substituted with chlorine, bromine, iodine or $C_1$–$C_4$ alkoxy; more preferably chlorine, bromine or methoxy; most preferably chlorine. The 5-position of the 1,3-cyclohexanedione moiety can be substituted with one or two $C_1$–$C_4$ alkyl groups, preferably methyl, although such a substitution is not preferred.

The compounds of Embodiment A of this invention can have the following four structural formulae because of tautomerism:

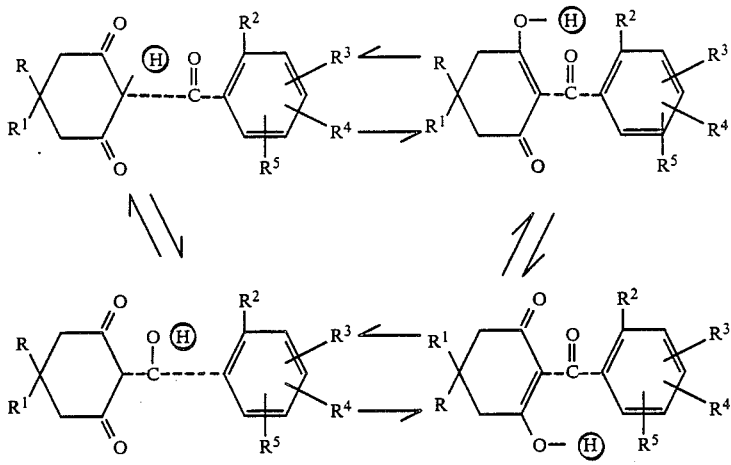

wherein R, $R^1$, $R^2$, $R^3$, $R^4$ and $R^5$ are as defined above.

The circled proton on each of the four tautomers is reasonably labile. These protons are acidic and can be removed by any base to give a salt having an anion of the following four resonance forms:

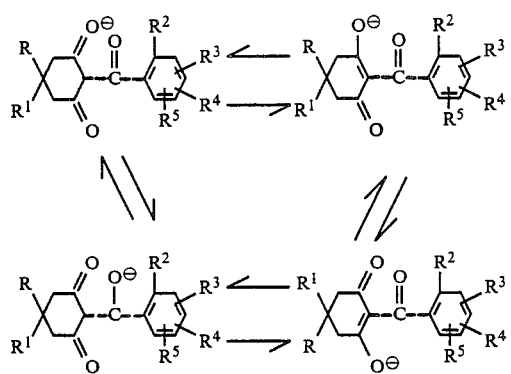

wherein R, $R^1$, $R^2$, $R^3$, $R^4$ and $R^5$ are as defined above.

Examples of cations of these bases are inorganic cations such as alkali metals, e.g. lithium, sodium, and potassium, alkaline earth metals, e.g. barium, magnesium, calcium and strontium or organic cations such as substituted ammonium, sulfonium or phosphonium wherein the substituent is an aliphatic or aromatic group.

In the above description of the compounds of this invention, alkyl and alkoxy include both straight and branched configurations; for example, methyl, ethyl, n-propyl, isopropyl, n-butyl, sec-butyl, isobutyl, and tert-butyl.

Embodiment B of this invention relates to certain novel 2-(2-substituted benzoyl)-cyclohexane-1,3-diones as herbicides. The compounds of this embodiment have the following structural formula

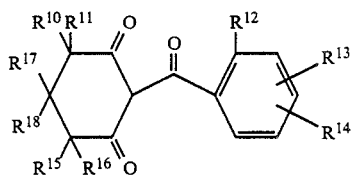

wherein $R^{10}$ is $C_1$-$C_6$ alkyl, preferably $C_1$-$C_4$, more preferably methyl;

$R^{11}$ is hydrogen or $C_1$-$C_6$ alkyl, preferably $C_1$-$C_4$, more preferably methyl or

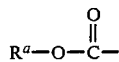

wherein $R^a$ is $C_1$-$C_4$ alkyl or $R^{10}$ and $R^{11}$ together are alkylene having 3 to 6 carbon atoms, most preferably $R^{11}$ is hydrogen or methyl;

$R^{12}$ is chlorine, bromine, iodine, fluorine or $C_1$-$C_4$ alkoxy, preferably methoxy; most preferably $R^{12}$ is chlorine, bromine or methoxy;

$R^{13}$ and $R^{14}$ independently are (1) hydrogen or an aliphatic group, preferably hydrogen; (2) halogen, preferably, fluorine, chlorine or bromine; (3) $C_1$-$C_4$ alkyl, preferably methyl; (4) $C_1$-$C_4$ aliphatic alkoxy, preferably methoxy; (5) trifluoromethoxy; (6) cyano; (7) nitro; (8) $C_1$-$C_4$ haloalkyl, more preferably trifluoromethyl; (9) $R^bSO_n$— wherein $R^b$ is $C_1$-$C_4$ alkyl, preferably methyl, $C_1$-$C_4$ haloalkyl, phenyl, benzyl, —$NR^dR^e$ wherein $R^d$ and $R^e$ independently are hydrogen or $C_1$-$C_4$ alkyl; and n is the integer 0, 1 or 2, preferably 2;

wherein $R^c$ is $C_1$-$C_4$ alkyl and $R^j$ is hydrogen or $C_1$-$C_4$ alkyl, preferably methyl; (11) $R^fC(O)$ wherein $R^f$ is hydrogen, $C_1$-$C_4$ alkyl, $C_1$-$C_4$ haloalkyl, $C_1$-$C_4$ alkoxy; (12) —$NR^gR^h$ wherein $R^g$ and $R^h$ independently are hydrogen or $C_1$-$C_4$ alkyl; (13) $C_1$-$C_4$ alkylthio or less preferably (14) $R^{13}$ and $R^{14}$ together can form a ring structure with two adjacent carbon atoms of the phenyl ring to which they are attached or less preferably (15) $R^{13}$ and $R^{14}$ are the groups phenoxy or substituted phenoxy wherein the substituent is halogen or halomethyl or both;

$R^{15}$, $R^{16}$, $R^{17}$ and $R^{18}$ are independently the same or different and are selected from the group consisting of hydrogen, $C_1$-$C_6$ alkyl, preferably $C_1$-$C_4$ alkyl, more preferably methyl, most preferably hydrogen or methyl, and their salts;

provided, however, that $R^{15}$ and $R^{16}$ together may form a substituted or unsubstituted alkylene ring of 2-5 carbon atoms, the preferred substituent being 1 or 2 methyl groups.

More preferably, $R^{13}$ is chlorine, hydrogen, methyl, alkylthio or methoxy. Preferably $R^{14}$ is hydrogen, chlorine, nitro, trifluoromethyl, or $R^bSO_n$ wherein $R^b$ is $C_1$-$C_4$ alkyl, preferably methyl and n is the integer 0, 1 or 2, preferably 2.

The compounds of Embodiment B of this invention can have the following four structural formulae because of tautomerism:

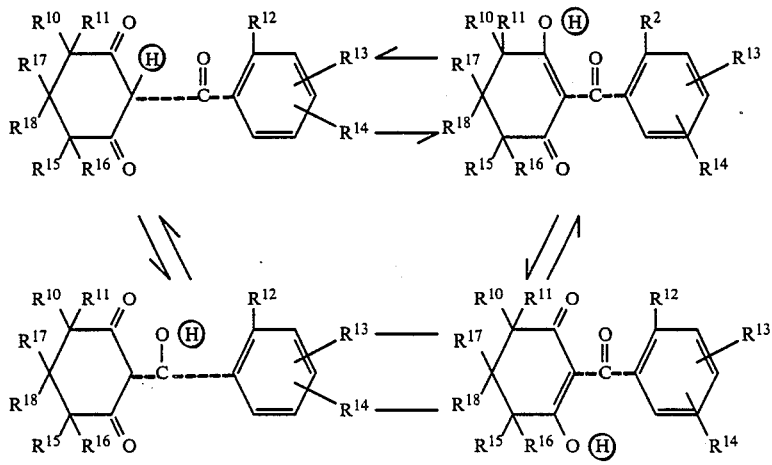

wherein $R^{10}$, $R^{11}$, $R^{12}$, $R^{13}$, $R^{14}$, $R^{15}$, $R^{16}$, $R^{17}$ and $R^{18}$ are as defined above.

The circled proton on each of the four tautomers is reasonably labile. These protons are acidic and can be removed by any base to give a salt having an anion of the following four resonance forms:

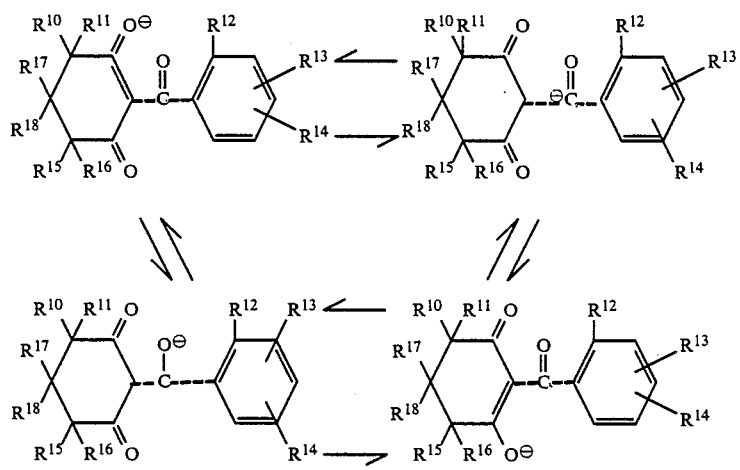

wherein $R^{10}$, $R^{11}$, $R^{12}$, $R^{13}$, $R^{14}$, $R^{15}$, $R^{16}$, $R^{17}$ and $R^{18}$ are as defined above.

Examples of cations of these bases are inorganic cations such as alkali metals e.g. lithium, sodium, and potassium, alkaline earth metals, e.g. barium, magnesium, calcium and strontium, or organic cations such as substituted ammonium, sulfonium or phosphonium wherein the substitutent is an aliphatic or aromatic group.

The term "aliphatic group" is used form Embodiments A and B herein in a broad sense to cover a large class of organic groups characterized by being derived from (1) an acylic (open-chain structure) of the paraffin, olefin and acetylene hydrocarbon series and their derivatives or (2) alicyclic compounds. The aliphatic group can have from 1 to 10 carbon atoms.

The term "aromatic group" is used for Embodiments A and B herein in a broad sense to distinguish from the aliphatic group and includes a group derived from (1) compounds having 6 to 20 carbon atoms and characterized by the presence of at least one benzene ring, including monocyclic, bicyclic and polycyclic hydrocarbons and their derivatives and (2) heterocyclic compounds having 5 to 19 carbon atoms which are similar in structure and are characterized by having an unsaturated ring structure containing at least one atom other than carbon such as nitrogen, sulfur and oxygen and derivatives of these heterocyclic compounds.

In the above description of the compounds of this invention alkyl and alkoxy include both straight and branched configurations; for example, methyl, ethyl, n-propyl, isopropyl, n-butyl, sec-butyl, isobutyl, and tert-butyl.

Embodiment C of this invention relates to certain novel 2-(2'-cyanobenzoyl)cyclohexane-1,3-diones as herbicides. The compounds of of this embodiment have the following structural formula

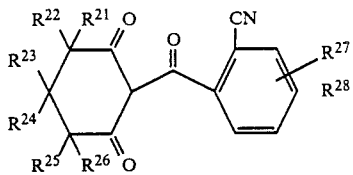

wherein
R$^{21}$ is hydrogen or C$_1$-C$_4$ alkyl, preferably C$_1$-C$_2$ alkyl, more preferably methyl, most preferably R$^{21}$ is hydrogen or methyl;
R$^{22}$ is hydrogen; C$_1$-C$_4$ alkyl, preferably C$_1$-C$_2$ alkyl, more preferably methyl or

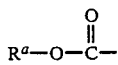

wherein R$^a$ is C$_1$-C$_4$ alkyl, most preferably R$^{22}$ is hydrogen or methyl; or R$^{21}$ and R$^{22}$ together are alkylene having 3 to 6 carbon atoms;
R$^{23}$ is hydrogen or C$_1$-C$_4$ alkyl, preferably C$_1$-C$_2$ alkyl, more preferably methyl; most preferably R$^{23}$ is hydrogen or methyl;
R$^{24}$ is hydrogen or C$_1$-C$_4$ alkyl, preferably C$_1$-C$_2$ alkyl, more preferably methyl; most preferably R$^{24}$ is hydrogen or methyl;
R$^{25}$ is hydrogen or C$_1$-C$_4$ alkyl, preferably C$_1$-C$_2$ alkyl, more preferably methyl; most preferably R$^{25}$ is hydrogen or methyl;
R$^{26}$ is hydrogen or C$_1$-C$_4$ alkyl, preferably C$_1$-C$_2$ alkyl, more preferably methyl; most preferably R$^{26}$ is hydrogen;

R$^{27}$ and R$^{28}$ independently are (1) hydrogen; (2) halogen, preferably chlorine, fluorine or bromine; (3) C$_1$-C$_4$ alkyl, preferably methyl;
(4) C$_1$-C$_4$ alkoxy, preferably methoxy; (5) trifluoromethoxy; (6) cyano; (7) nitro; (8) C$_1$-C$_4$ haloalkyl, more preferably trifluoromethyl; (9) R$^b$SO$_n$— wherein n is the integer 0, 1 or 2, preferably 2; and
R$^b$ is
  (a) C$_1$-C$_4$ alkyl, preferably methyl;
  (b) C$_1$-C$_4$ alkyl substituted with halogen or cyano, preferably chloromethyl, trifluoromethyl or cyanomethyl;
  (c) phenyl; or
  (d) benzyl;
(10) —NR$^c$R$^d$ wherein R$^c$ and R$^d$ independently are hydrogen or C$_1$-C$_4$ alkyl;
(11) R$^e$C(O)— wherein R$^e$ is C$_1$-C$_4$ alkyl or C$_1$-C$_4$ alkoxy; or
(12) —SO$_2$NR$^c$R$^d$ wherein R$^c$ and R$^d$ are as defined, with the proviso that R$^{27}$ is not attached to the 6-position.

Preferably, R$^{27}$ is in the 3-position. Most preferably R$^{27}$ is hydrogen and R$^{28}$ is hydrogen, chlorine, bromine, fluorine, trifluoromethyl, or R$^b$SO$_2$ wherein R$^b$ is C$_1$-C$_4$ alkyl, preferably methyl.

Salts of the above-described compounds (as defined hereinafter) are also the subject of the instant invention.

The compounds of this embodiment can have the following four structural formulae because of tautomerism:

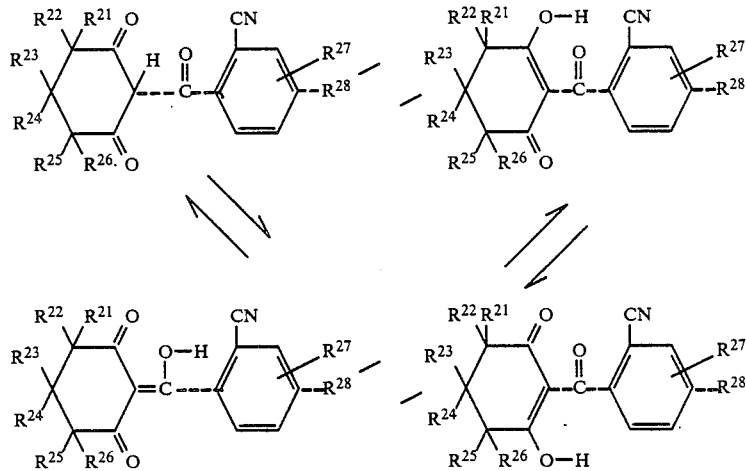

wherein R$^{21}$, R$^{22}$, R$^{23}$, R$^{24}$, R$^{25}$, R$^{26}$, R$^{27}$ and R$^{28}$ are as defined above.

The circled proton on each of the four tautomers is reasonably labile. These protons are acidic and can be removed by any base to give a salt having an anion of the following four resonance forms:

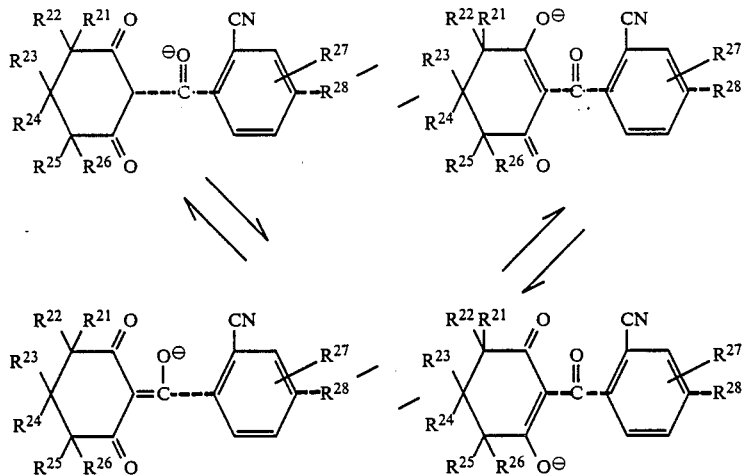

wherein $R^{21}$, $R^{22}$, $R^{23}$, $R^{24}$, $R^{25}$, $R^{26}$, $R^{27}$ and $R^{28}$ are as defined above.

Examples of cations of these bases are inorgaic cations such as alkali metals e.g. lithium, sodium, and potassium organic cations such as substituted ammonium, sulfonium or phosphonium wherein the substitutent is an aliphatic or aromatic group.

Embodiment D of this invention relates to 2-(2-nitrobenzoyl)-1,3-cyclohexanediones and their use as herbicides.

The compounds have a nitro substitution in the 2-position of the phenyl moiety of their compounds. The nitro substitution imparts exceptional herbicidal activity to the compounds of this invention.

Embodiment D' of this invention is an herbicidal composition comprising an herbicidally active 2-(2-nitrobenzoyl)-1,3-cyclohexanedione and an inert carrier therefor. The 4-, 5- and 6-positions of the 1,3-cyclohexanedione moiety can be substituted, preferably with the groups hereinafter recited. More preferably, the 1,3-cyclohexanedione moiety has no substitution or the 4- or 6-positions are substituted with one or two methyl groups. The 3-, 4- and 5-positions of the benzoyl moiety can be substituted, preferably with the groups hereinafter recited.

The novel compounds of Embodiment D have the following structural formula

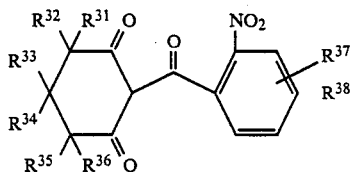

wherein $R^{31}$ is hydrogen or $C_1$–$C_4$ alkyl, preferably $C_1$–$C_2$ alkyl, more preferably methyl, most preferably $R^{31}$ is hydrogen or methyl;

$R^{32}$ is hydrogen; $C_1$–$C_4$ alkyl, preferably $C_1$–$C_2$ alkyl, more preferably methyl or

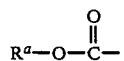

wherein $R^a$ is $C_1$–$C_4$ alkyl, most preferably $R^{32}$ is hydrogen or methyl; or $R^{31}$ and $R^{32}$ together are alkylene having 3 to 6 carbon atoms;

$R^{33}$ is hydrogen or $C_1$–$C_4$ alkyl, preferably $C_1$–$C_2$ alkyl, more preferably methyl; most preferably $R^{33}$ is hydrogen or methyl;

$R^{34}$ is hydrogen or $C_1$–$C_4$ alkyl, preferably $C_1$–$C_2$ alkyl, more preferably methyl; most preferably $R^{34}$ is hydrogen or methyl;

$R^{35}$ is hydrogen or $C_1$–$C_4$ alkyl, preferably $C_1$–$C_2$ alkyl, more preferably methyl; most preferably $R^{35}$ is hydrogen or methyl;

$R^{36}$ is hydrogen or $C_1$–$C_4$ alkyl, preferably $C_1$–$C_2$ alkyl, more preferably methyl, most preferably $R^{36}$ is hydrogen;

$R^{37}$ and $R^{38}$ independently are (1) hydrogen; (2) halogen, preferably chlorine, fluorine or bromine; (3) $C_1$–$C_4$ alkyl, preferably methyl; (4) $C_1$–$C_4$ alkoxy, preferably methoxy; (5) trifluoromethoxy; (6) cyano; (7) nitro; (8) $C_1$–$C_4$ haloalkyl, more preferably trifluoromethyl; (9) $R^b SO_n$— wherein n is the integer 0, 1 or 2, preferably 2; and $R^b$ is (a) $C_1$–$C_4$ alkyl, preferably methyl;

(b) $C_1$–$C_4$ alkyl substituted with halogen or cyano, preferably chloromethyl, trifluoromethyl or cyanomethyl;

(c) phenyl; or (d) benzyl;

(10) —$NR^c R^d$ wherein $R^c$ and $R^d$ independently are hydrogen or $C_1$–$C_4$ alkyl;

(11) $R^e C(O)$— wherein $R^e$ is $C_1$–$C_4$ alkyl or $C_1$–$C_4$ alkoxy; or

(12) —$SO_2 NR^c R^d$ wherein $R^c$ and $R^d$ are as defined, with the proviso that $R^{37}$ is not attached to the 6-position.

Preferably, $R^{37}$ is in the 3-position. Most preferably $R^{37}$ is hydrogen or $C_1$–$C_4$ alkoxy and $R^{38}$ is hydrogen, chlorine, bromine, fluorine, trifluoromethyl, or $R^b SO_2$ wherein $R^b$ is $C_1$–$C_4$ alkyl, preferably methyl.

The term "$C_1$–$C_4$ alkyl" includes methyl, ethyl, n-propyl, isopropyl, n-butyl, sec-butyl, isobutyl and t-butyl. The term "halogen" includes chlorine, bromine, iodine and fluorine. The terms "$C_1$–$C_4$ alkoxy" includes methoxy, ethoxy, n-propoxy, isopropoxy, n-butoxy, sec-butoxy, isobutoxy and t-butoxy. The term "haloalkyl" includes the eight alkyl groups with one or more hydrogens replaced by chlorine, bromine, iodine or fluorine.

Salts of the above-described compounds (as defined hereinafter) are also the subject of the instant invention.

The compounds of this invention can have the following four structural formulae because of tautomerism:

rier therefor. The 4-, 5- and 6-positions of the 1,3-cyclohexanedione moiety can be substituted, preferably with the groups hereinafter recited. More preferably, the 1,3-cyclohexanedione moiety has no substitution or the 4- or 6-positions are substituted with one or two methyl groups. The 3-, 4- and 5-positions of the benzoyl moiety can be substituted, preferably with the groups hereinafter recited.

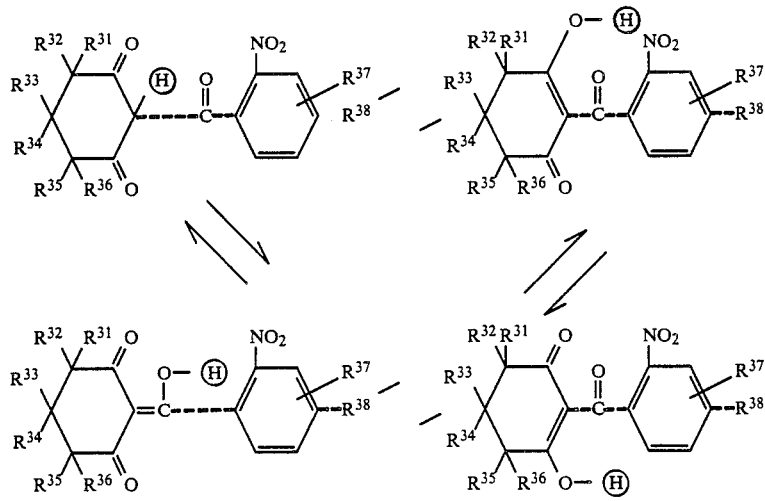

wherein $R^{31}$, $R^{32}$, $R^{33}$, $R^{34}$, $R^{35}$, $R^{36}$, $R^{37}$ and $R^{38}$ are as defined above.

The circled proton on each of the four tautomers is reasonably labile. These protons are acidic and can be removed by any base to give a salt having an anion of the following four resonance forms:

The novel compounds of Embodiment E have the structural formula

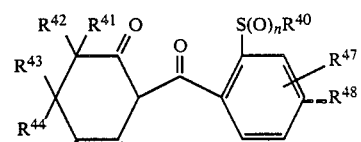

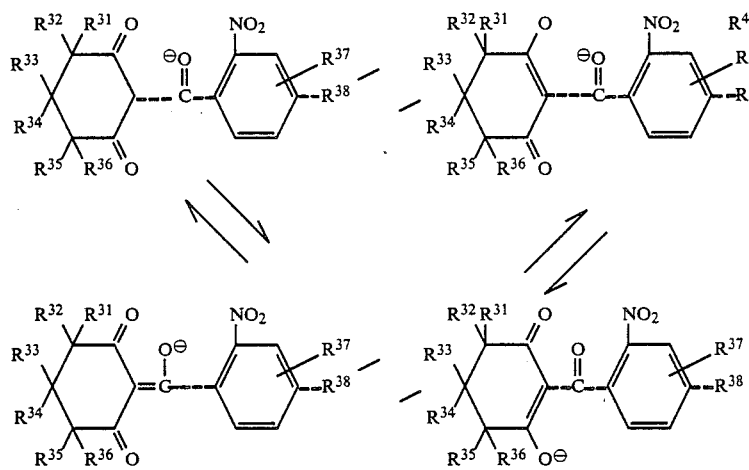

wherein $R^{31}$, $R^{32}$, $R^{33}$, $R^{34}$, $R^{35}$, $R^{36}$, $R^{37}$ and $R^{38}$ are as defined above.

Examples of cations of these bases are inorganic cations such as alkali metals e.g. lithium, sodium, and potassium or organic cations such as substituted ammonium, sulfonium or phosphonium wherein the substitutent is an aliphatic or aromatic group.

Embodiment E of this invention relates to 2-(2-benzoyl)-1,3-cyclohexanediones and their use as herbicides.

Embodiment E' of this invention is an herbicidal composition comprising an herbicidally active 2-(2-$C_1$-$C_4$ alkylthio, $C_1$-$C_4$ alkylsulfinyl or $C_1$-$C_4$ alkylsulfonyl benzoyl)-1,3-cyclohexanedione and an inert carwherein
n is the integer 0, 1 or 2, preferably 2;
$R^{40}$ is $C_1$-$C_4$ alkyl, preferably methyl;
$R^{41}$ is hydrogen or $C_1$-$C_4$ alkyl, preferably $C_1$-$C_2$ alkyl, more preferably methyl, most preferably $R^{41}$ is hydrogen or methyl;

$R^{42}$ is hydrogen; $C_1$–$C_4$ alkyl, preferably $C_1$–$C_2$ alkyl, more preferably methyl or

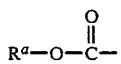

wherein $R^a$ is $C_1$–$C_4$ alkyl, most preferably $R^{42}$ is hydrogen or methyl; or $R^{41}$ and $R^{42}$ together are alkylene having 3 to 6 carbon atoms;

$R^{43}$ is hydrogen or $C_1$–$C_4$ alkyl, preferably $C_1$–$C_2$ alkyl, more preferably methyl; most preferably $R^{43}$ is hydrogen or methyl;

$R^{44}$ is hydrogen or $C_1$–$C_4$ alkyl, preferably $C_1$–$C_2$ alkyl, more preferably methyl; most preferably $R^{44}$ is hydrogen or methyl;

$R^{45}$ is hydrogen or $C_1$–$C_4$ alkyl, preferably $C_1$–$C_2$ alkyl, more preferably methyl; most preferably $R^{45}$ is hydrogen or methyl;

$R^{46}$ is hydrogen or $C_1$–$C_4$ alkyl, preferably $C_1$–$C_2$ alkyl, more preferably methyl, most preferably $R^{46}$ is hydrogen;

$R^{47}$ and $R^{48}$ independently are (1) hydrogen; (2) halogen, preferably chlorine, fluorine or bromine; (3) $C_1$–$C_4$ alkyl, preferably methyl; (4) $C_1$–$C_4$ alkoxy, preferably methoxy; (5) trifluoromethoxy; (6) cyano; (7) nitro; (8) $C_1$–$C_4$ haloalkyl, more preferably trifluoromethyl; (9) $R^bSO_n$— wherein n is the integer 0, 1 or 2, preferably 2; and $R^b$ is (a) $C_1$–$C_4$ alkyl, preferably methyl;

(b) $C_1$–$C_4$ alkyl substituted with halogen or cyano, preferably chloromethyl, trifluoromethyl or cyanomethyl;

(c) phenyl; or (d) benzyl;

(10) —$NR^cR^d$ wherein $R^c$ and $R^d$ independently are hydrogen or $C_1$–$C_4$ alkyl; (11) $R^eC(O)$— wherein $R^e$ is $C_1$–$C_4$ alkyl or $C_1$–$C_4$ alkoxy; or (12) —$SO_2NR^cR^d$ wherein $R^c$ and $R^d$ are as defined, with the proviso that $R^{47}$ is not attached to the 6-position.

Preferably, $R^{47}$ is in the 3-position. Most preferably $R^{47}$ is hydrogen or 3-chlorine and $R^{48}$ is hydrogen, chlorine, bromine, fluorine, trifluoromethyl, or $R^bSO_2$ wherein $R^b$ is $C_1$–$C_4$ alkyl, preferably methyl.

The term "$C_1$–$C_4$" alkyl includes methyl, ethyl, n-propyl, isopropyl, n-butyl, sec-butyl, isobutyl and t-butyl. The term "halogen" includes chlorine, bromine, iodine and fluorine. The term "$C_1$–$C_4$ alkoxy" includes methoxy, ethoxy, n-propoxy, isopropoxy, n-butoxy, sec-butoxy, isobutoxy and t-butoxy. The term "haloalkyl" includes the eight alkyl groups with one or more hydrogens replaced by chloro, bromo, iodo or fluoro.

Salts of the above-described compounds (as defined hereinafter) are also the subject of the instant invention.

The compounds of this invention can have the following four structural formulae because of tautomerism:

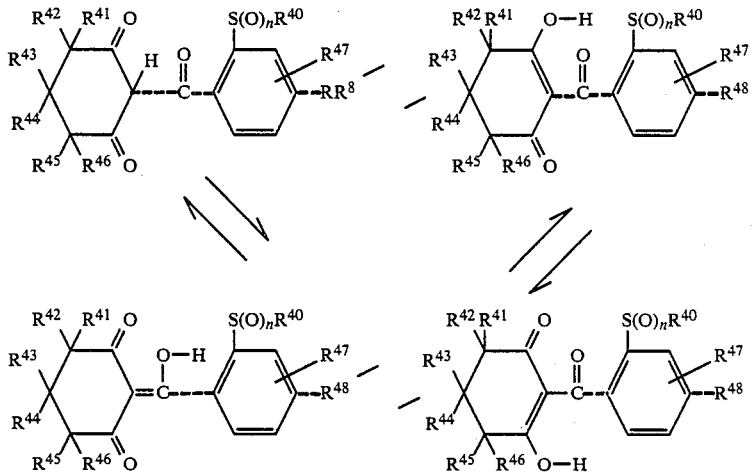

wherein n, $R^{40}$, $R^{41}$, $R^{42}$, $R^{43}$, $R^{44}$, $R^{45}$, $R^{46}$, $R^{47}$ and $R^{48}$ are as defined above.

The circled proton on each of the four tautomers is reasonably labile. These protons are acidic and can be removed by any base to give a salt having an anion of the following four resonance forms:

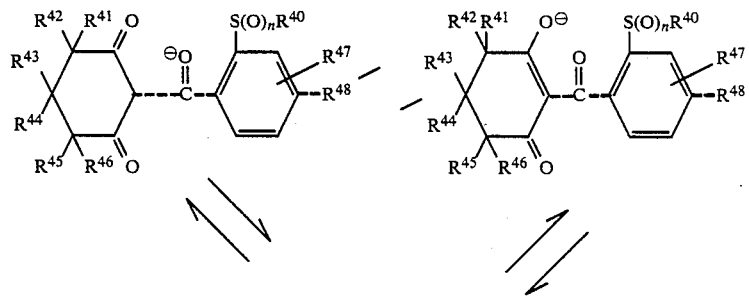

-continued

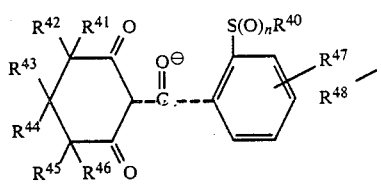 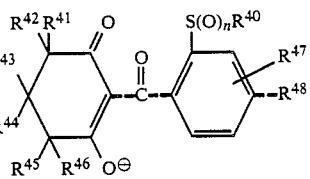

wherein n, $R^{40}$, $R^{41}$, $R^{42}$, $R^{43}$, $R^{44}$, $R^{45}$, $R^{46}$, $R^{47}$ and $R^{48}$ are as defined above.

Examples of cations of these bases are inorganic cations such as alkali metals e.g. lithium, sodium, and potassium, organic cations such as substituted ammonium, sulfonium or phosphonium wherein the substitutent is an aliphatic or aromatic group.

Embodiment F of this invention relates to 2-(2-alkylbenzoyl)-1,3-cyclohexanediones and their use as herbicides.

Embodiment F' of this invention is an herbicidal composition comprising an herbicidally active 2-benzoyl-1,3-cyclohexanedione and an inert carrier therefor wherein the 2-position of the benzoyl moiety is substituted with $C_1$-$C_4$ alkyl, preferably $C_1$-$C_2$ alkyl, optionally substituted with halogen, more preferably methyl or trifluoromethyl and the 4-position preferably is substituted with an electron withdrawing group, such as halogen, cyano, trifluoromethyl or nitro. The 4-, 5- and 6-positions of the 1,3-cyclohexanedione moiety can be substituted, preferably with the groups hereinafter recited. More preferably, the 1,3-cyclohexanedione moiety has no substitution or the 4- or 6-positions are substituted with one or two methyl groups. The 3-, 4- and 5-positions of the benzoyl moiety can be substituted, preferably with the groups hereinafter recited.

The novel compounds of Embodiment F have the following structural formula

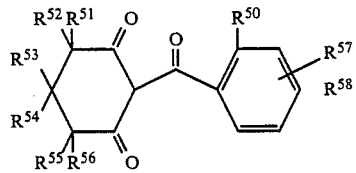

wherein
$R^{50}$ is $C_1$-$C_4$ alkyl, preferably $C_1$-$C_2$ alkyl, optionally substituted with halogen, more preferably methyl and trifluoromethyl;
$R^{51}$ is hydrogen or $C_1$-$C_4$ alkyl, preferably $C_1$-$C_2$ alkyl, more preferably methyl, most preferably $R^{51}$ is hydrogen or methyl;
$R^{52}$ is hydrogen; $C_1$-$C_4$ alkyl, preferably $C_1$-$C_2$ alkyl, more preferably methyl or

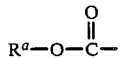

wherein $R^a$ is $C_1$-$C_4$ alkyl, most preferably $R^{52}$ is hydrogen or methyl; or
$R^{51}$ and $R^{52}$ together are alkylene having 3 to 6 carbon atoms;
$R^{53}$ is hydrogen or $C_1$-$C_4$ alkyl, preferably $C_1$-$C_2$ alkyl, more preferably methyl; most preferably $R^{53}$ is hydrogen or methyl;
$R^{54}$ is hydrogen or $C_1$-$C_4$ alkyl, preferably $C_1$-$C_2$ alkyl, more preferably methyl; most preferably $R^{54}$ is hydrogen or methyl;
$R^{55}$ is hydrogen or $C_1$-$C_4$ alkyl, preferably $C_1$-$C_2$ alkyl, more preferably methyl; most preferably $R^{55}$ is hydrogen or methyl;
$R^{56}$ is hydrogen or $C_1$-$C_4$ alkyl, preferably $C_1$-$C_2$ alkyl, more preferably methyl, most preferably $R^{56}$ is hydrogen;
$R^{57}$ and $R^{58}$ independently are (1) hydrogen; (2) halogen; preferably chlorine, fluorine or bromine; (3) $C_1$-$C_4$ alkyl, preferably methyl; (4) $C_1$-$C_4$ alkoxy, preferably methoxy; (5) trifluoromethoxy; (6) cyano; (7) nitro; (8) $C_1$-$C_4$ haloalkyl, more preferably trifluoromethyl; (9) $R^bSO_n$— wherein n is the integer 0, 1 or 2, preferably 2; and
$R^b$ is
(a) $C_1$-$C_4$ alkyl, preferably methyl;
(b) $C_1$-$C_4$ alkyl substituted with halogen or cyano, preferably chloromethyl, trifluoromethyl or cyanomethyl;
(c) phenyl; or
(d) benzyl;
(10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; or (12) —$SO_2NR^cR^d$ wherein $R^c$ and $R^d$ are as defined, with the proviso that $R^{57}$ is not attached to the 6-position.

The term "$C_1$-$C_4$ alkyl" includes methyl, ethyl, n-propyl, isopropyl, n-butyl, sec-butyl, isobutyl and t-butyl. The term "halogen" includes chlorine, bromine, iodine and fluorine. The term "$C_1$-$C_4$ alkoxy" includes methoxy, ethoxy, n-propoxy, isopropoxy, n-butoxy, sec-butoxy, isobutoxy and t-butoxy. The term "haloalkyl" includes the eight alkyl groups with one or more hydrogens replaced by chloro, bromo, iodo or fluoro.

Preferably, $R^{57}$ is in the 3-position. Most preferably $R^{57}$ is hydrogen and $R^{58}$ is hydrogen, chlorine, bromine, fluorine, trifluoromethyl, or $R^bSO_2$ wherein $R^b$ is $C_1$-$C_4$ alkyl, preferably methyl.

Salts of the above-described compounds (as defined hereinafter) are also the subject of the instant invention.

The compounds of this invention can have the following four structural formulae because of tautomerism:

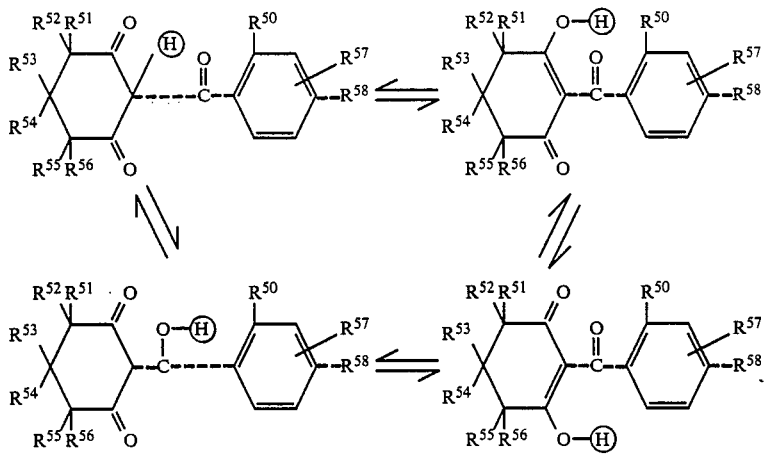

wherein $R^{50}$, $R^{51}$, $R^{52}$, $R^{53}$, $R^{54}$, $R^{55}$, $R^{56}$, $R^{57}$ and $R^{58}$ are as defined above.

The circled proton on each of the four tautomers is reasonably labile. These protons are acidic and can be removed by any base to give a salt having an anion of the following four resonance forms:

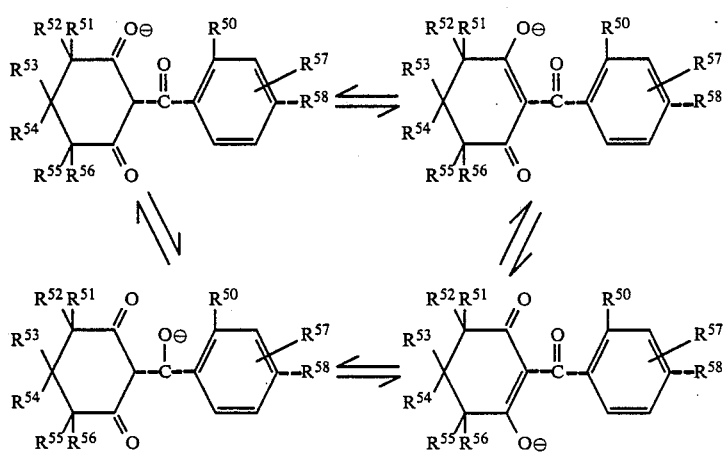

wherein $R^{50}$, $R^{51}$, $R^{52}$, $R^{53}$, $R^{54}$, $R^{55}$, $R^{56}$, $R^{57}$ and $R^{58}$ are as defined above.

Examples of cations of these bases are inorganic cations such as alkali metals e.g. lithium, sodium, and potassium organic cations such as substituted ammonium, sulfonium or phosphonium wherein the substituent is an aliphatic or aromatic group.

Embodiment G of this invention relates to 2-benzoyl-1,3,5-cyclohexanetriones and their use as herbicides.

Embodiment G' of this invention is an herbicidal composition comprising an herbicidally active 2-benzoyl-substituted-1,3,5-cyclohexanetrione and an inert carrier therefor. The 4- and 6-positions of the 1,3,5-cyclohexanetrione moiety are preferably substituted with groups hereinafter defined, most preferably with all methyl groups. The benzoyl moiety can be substituted, preferably with the groups hereinafter recited.

The novel compounds of Embodiment G have the following structural formula wherein $R^{60}$ is hydrogen; halogen; $C_1$-$C_2$ alkyl, preferably methyl; $C_1$-$C_2$ alkoxy, preferably methoxy; nitro; cyano; $C_1$-$C_2$ haloalkyl, preferably trifluoromethyl; $R^aSO_n$— wherein n is 0 or 2, preferably 2 and $R^a$ is $C_1$-$C_2$ alkyl, preferably methyl, trifluoromethyl or difluoromethyl; or trifluoromethoxy or difluoromethoxy. Preferably, $R^{60}$ is chlorine, bromine, $C_1$-$C_2$ alkyl, $C_1$-$C_2$ alkoxy, trifluoromethyl, cyano, nitro, $C_1$-$C_2$ alkylthio or $C_1$-$C_2$ alkylsulfonyl; more preferably chlorine, nitro, methyl, trifluoromethyl or methylsulfonyl; and $R^{61}$ is hydrogen or $C_1$-$C_4$ alkyl, preferably methyl;
$R^{62}$ is hydrogen or $C_1$-$C_4$ alkyl, preferably methyl; or
$R^{61}$ and $R^{62}$ together are $C_2$-$C_5$ alkylene;
$R^{63}$ is $C_1$-$C_4$ alkyl, preferably methyl;
$R^{64}$ is $C_1$-$C_4$ alkyl, preferably methyl; or
$R^{63}$ and $R^{64}$ together are $C_2$-$C_5$ alkylene;
$R^{65}$ and $R^{66}$ independently are (1) hydrogen; (2) halogen, preferably chlorine, fluorine or bromine; (3) $C_1$-$C_4$ alkyl, preferably methyl; (4) $C_1$-$C_4$ alkoxy, preferably methoxy; (5) trifluoromethoxy; (6) cyano; (7) nitro; (8) $C_1$–$C_4$ haloalkyl, more preferably trifluoromethyl; (9) $R^bSO_n$— wherein n is the integer 0, 1 or 2, preferably 2; and $R^b$ is
(a) $C_1$–$C_4$ alkyl, preferably methyl;
(b) $C_1$–$C_4$ alkyl substituted with halogen or cyano, preferably chloromethyl, trifluoromethyl or cyanomethyl;
(c) phenyl; or
(d) benzyl;
(10) —$NR^cR^d$ wherein $R^c$ and $R^d$ independently are hydrogen or $C_1$–$C_4$ alkyl; (11) $R^eC(O)$— wherein $R^e$ is $C_1$–$C_4$ alkyl or $C_1$–$C_4$ alkoxy; (12) —$SO_2NR^cR^d$ wherein $R^c$ and $R^d$ are as defined; or (13) —$N(R^c)$-C(O)$R^d$ wherein $R^c$ and $R^d$ are as defined.

Preferably $R^{65}$ is in the 3-position. More preferably $R^{65}$ is hydrogen, chlorine, fluorine, trifluoromethyl, cyano, $C_1$–$C_4$ alkoxy or $C_1$–$C_4$ thioalkyl. Most preferably, $R^{65}$ is hydrogen. Preferably $R^{66}$ is in the 4-position. Most preferably $R^{66}$ is halogen, cyano, trifluoromethyl, or $R^bSO_2$ wherein $R^b$ is $C_1$–$C_4$ alkyl, preferably methyl or $C_1$–$C_4$ haloalkyl, preferably chloromethyl, difluoromethyl or trifluoromethyl.

The term "$C_1$–$C_4$ alkyl" includes methyl, ethyl, n-propyl, isopropyl, n-butyl, sec-butyl, isobutyl and t-butyl. The term "halogen" includes chlorine, bromine, iodine and fluorine. The terms "$C_1$–$C_4$ alkoxy" includes methoxy, ethoxy, n-propoxy, n-butoxy, sec-butoxy, isobutoxy and t-butoxy. The term "$C_1$–$C_4$ haloalkyl" includes the alkyl groups defined above under $C_1$–$C_4$ alkyl in which one or more hydrogens is replaced by chlorine, bromine, iodine or fluorine.

Salts of the above-described compounds (as defined hereinafter) are included within the scope of the instant invention.

The compounds of this invention can have the following four structural formulae because of tautomerism:

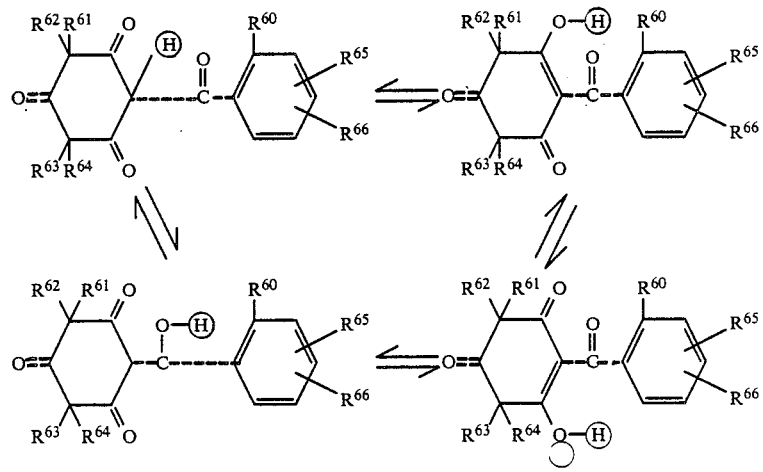

wherein $R^{60}$, $R^{61}$, $R^{62}$, $R^{63}$, $R^{64}$, $R^{65}$ and $R^{66}$ are as defined above.

The circled proton on each of the four tautomers is reasonably labile. These protons are acidic and can be removed by reaction with a base to form a salt having an anion of the following four resonance forms:

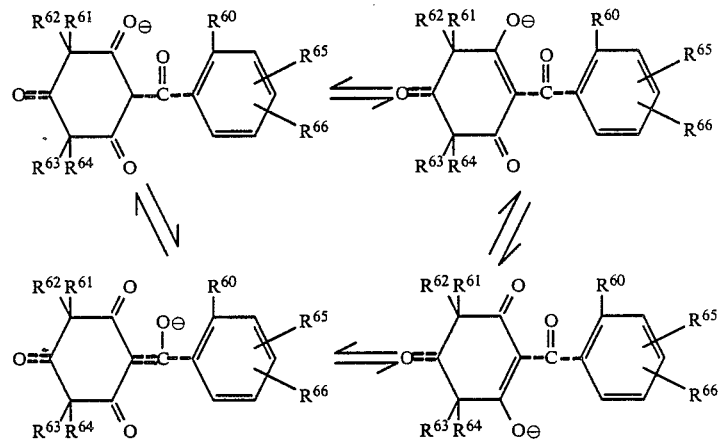

wherein $R^{60}$, $R^{61}$, $R^{62}$, $R^{63}$, $R^{64}$, $R^{65}$ and $R^{66}$ are as defined above.

Examples of cations of these bases are inorganic cations such as alkali metals, e.g., lithium, sodium and potassium; the alkaline earth metals, e.g. calcium and magnesium or ammonium or organic cations such as substituted ammonium, sulfonium, sulfoxonium or phosphonium wherein the substituents are aliphatic or aromatic groups.

Those skilled in the art will recognize in considering the salts of this invention that varying degress os association between the anion and cation will exist depending upon the nature of the cation. In some instances with a suitable cation, such as copper, the salt can exist in a chelated form.

The compounds of this invention and their salts are active herbicides of a general type. That is, they are herbicidally effective against a wide range of plant species. The method of controlling undesirable vegetation of the present invention comprises applying an herbicidally effective amount of the above-described compounds to the area where control is desired.

The compounds of Embodiments A and A' of the present invention can be prepared by the following general method.

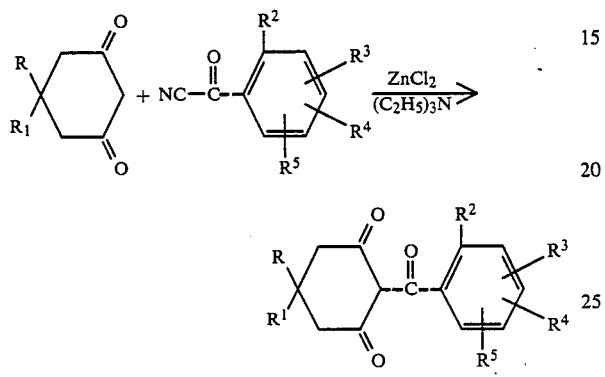

Generally, mole amounts of the dione and substituted benzoyl cyanide are used, along with a slight mole excess of zinc chloride. The two reactants and the zinc chloride are combined in a solvent such as methylene chloride. A slight mole excess of triethylamine is slowly added to the reaction mixture with cooling. The mixture is stirred at room temperature for 5 hours.

The reaction product is worked up by conventional techniques.

The above-described substituted benzoyl cyanide can be prepared according to the teaching of T. S. Oakwood and C. A. Weisgerber, *Organic Synthesis Collected*, Vol. III, pp. 122 (1955).

The following example teaches the synthesis of a representative compound of Embodiments A and A' of this invention.

EXAMPLE 1-A, A'

2-(2,4-Dichlorobenzoyl)-cyclohexane-1,3-dione

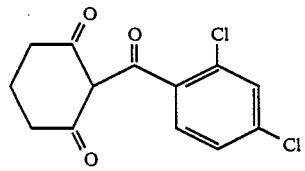

1,3-Cyclohexanedione [11.2 grams (g), 0.1 mole], 20.0 g (0.1 mole), 2,4-dichlorobenzoyl cyanide and 13.6 g (0.11 mole) anhydrous, powdered zinc chloride were combined in 100 milliliters (ml) methylene chloride. Triethylamine (10.1 g, 0.12 mole) was slowly added with cooling. The reaction mixture was stirred at room temperature for 5 hours and then poured into 2N hydrochloric acid. The aqueous phase was discarded and the organic phase was washed with 150 ml 5% $Na_2CO_3$ four times. The aqueous washings were combined and acidified with HCl, extracted with methylene chloride, dried and concentrated to yield 25.3 g of crude product.

The crude product was dissolved in ether and stirred with 250 ml of 5% copper (II) acetate. The resulting copper salt was filtered, washed with ether and stirred with 6N hydrochloric acid to destroy the salt. The extract was washed with ether to yield 22.15 grams of the desired product m.p. 138°-140° C. (77.7% yield). The structure was confirmed by instrumental analysis.

The compounds of Embodiment B of the present invention can be prepared by the following general method.

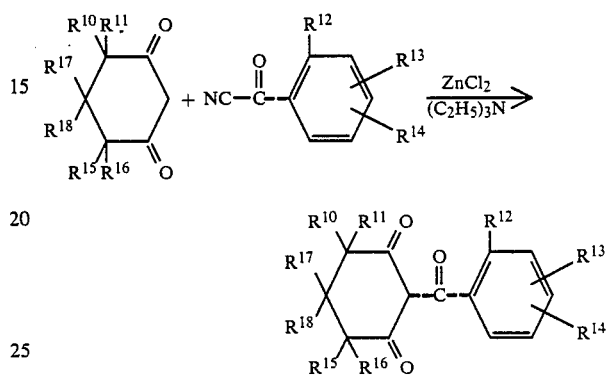

Generally, mole amounts of the dione and substituted benzoyl cyanide are used, along with a slight mole excess of zinc chloride. The two reactants and the zinc chloride are combined in a solvent such as methylene chloride. A slight mole excess of triethylamine is slowly added to the reaction mixture with cooling. The mixture is stirred at room temperature for 5 hours.

The reaction product is worked up by conventional techniques.

The above-described substituted benzoyl cyanide can be prepared according to the teaching of T. S. Oakwood and C. A. Weisgerber, *Organic Synthesis Collected*, Vol. III, pp. 122 (1955).

The following example teaches the synthesis of a representative compound of Embodiment B of this invention.

EXAMPLE 1-B 4,4-Dimethyl-2-(2,4-dichlorobenzoyl)-cyclohexane-1,3-dione

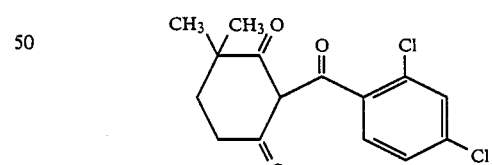

4,4-Dimethyl-1,3-cyclohexanedione [14.0 grams (g), 0.1 mole], 20.0 g (0.1 mole) 2,4-dichlorobenzoyl cyanide and 13.6 g (0.11 mole) anhydrous, powdered zinc chloride were combined in 100 milliliters (ml) methylene chloride. Triethylamine (10.1 g, 0.12 mole) was slowly added with cooling. The reaction mixture was stirred at room temperature for 5 hours and then poured into 2N hydrochloric acid. The aqueous phase was discarded and the organic phase was washed with 150 ml 5% $Na_2CO_3$ four times. The aqueous washings were combined and acidified with HCl, extracted with methylene chloride, dried and concentrated to yield 25.3 g of crude product. The crude product was chromatographed (2% AcOH/CH₂Cl₂) in 5 g aliquots then reduced on rotavap under reduced pressure at 50° C. for 30 minutes to remove AcOH. This yielded an oil (40% yield). The structure was confirmed by instrumental analysis.

The compounds of Embodiment C of the present invention can be prepared by the following general method.

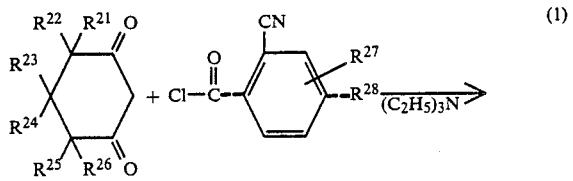 (1)

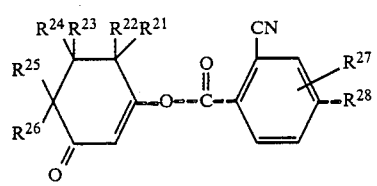

Generally, in step (1) mole amounts of the dione and substituted benzoyl chloride are used, along with a slight mole excess of triethylamine. The two reactants are combined in a solvent such as methylene chloride. The triethylamine is slowly added to the reaction mixture with cooling. The mixture is stirred at room temperature for several hours.

The reaction product is worked up by conventional techniques.

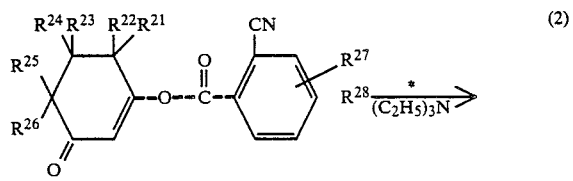 (2)

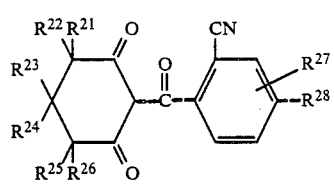

* = acetone cyanohydrin or KCN

Generally, in step (2) a mole of the enol ester intermediate is reacted with 1 to 4 moles of the triethylamine, preferably 2 moles of the triethylamine and up to 0.5 mole, preferably 0.1 mole of a cyanide source (e.g., potassium cyanide or acetone cyanohydrin). The mixture is stirred in a reaction pot for about one hour at room temperature and the desired product is recovered by conventional techniques.

The above described substituted benzoyl chlorides can be prepared from the corresponding substituted benzoic acids according to the teaching of *Reagents for Organic Synthesis*, Vol. I, L. F. Fieser and M. Fieser, pp. 767–769 (1967).

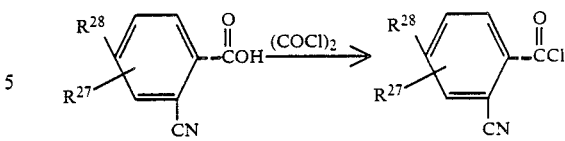

wherein $R^{27}$ and $R^{28}$ are as previously defined.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C. A. Buehler and D. F. Pearson, J. Wiley and Sons, (1970).

The following are two representative examples of the methods described therein.

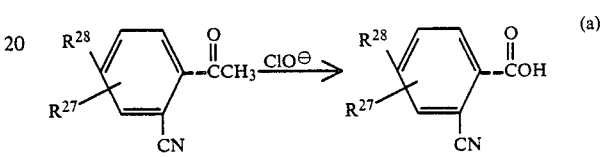 (a)

wherein $R^{27}$ and $R^{28}$ are as previously defined.

In reaction (a) the substituted acetophenone is heated to reflux for several hours in an aqueous hypochlorite solution. The mixture is cooled and the reaction product is isolated by conventional techniques.

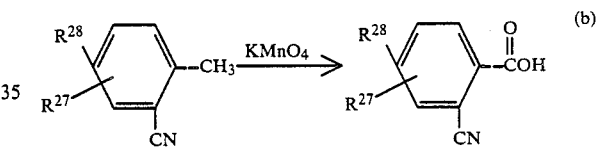 (b)

wherein $R^{27}$ and $R^{28}$ are as previously defined.

In reaction (b) the substituted toluene is heated to reflux in an aqueous solution of potassium permanganate for several hours. The solution is then filtered and the reaction product is isolated by conventional techniques.

The following example teaches the synthesis of a representative compound of Embodiment C of this invention.

EXAMPLE 1-C 2-(2′-Cyanobenzoyl)-4,4-dimethyl-1,3-cyclohexanedione

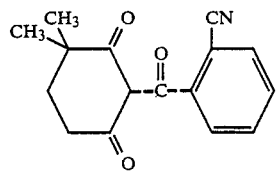

2-Cyanobenzoyl chloride (3.9 g, 24 mmol) and 4,4-dimethyl-1,3-cyclohexanedione (3.3 g, 24 mmol) were dissolved in 75 ml methylene chloride. Triethylamine (5.0 ml, 36 mmol) was added dropwise and the resulting solution stirred for one and one-half hours at room temperature. The solution was washed with water, 2 normal hydrochloric acid (2N HCl), 5% potassium carbonate solution (5% K₂CO₃) and saturated sodium chloride solution (brine), dried over anhydrous magnesium sulfate (MgSO$_4$) and concentrated under vacuum. The residue was dissolved in 20 ml acetonitrile. Triethylamine (4.4 ml, 32 mmol) and acetone cyanohydrin (5 drops) were added and the solution stirred for two hours. After dilution with ether, the solution was washed with 2N HCl and extracted with 5% K$_2$CO$_3$. The aqueous extract was acidified with concentrated hydrochloric acid and extracted with ether. The ether was washed with water and brine, dried (MgSO$_4$) and concentrated under vacuum. The residue was purified by silica gel chromatography, yielding 1.2 g of a viscous oil which was identified as the desired compound by nuclear magnetic resonance spectroscopy, infrared spectroscopy and mass spectroscopy.

The compounds of Embodiments D and D' of the present invention can be prepared by the following two-step general method.

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

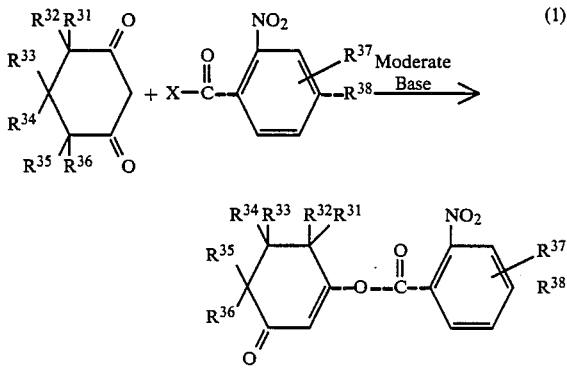

wherein R$^{31}$ through R$^{38}$ and moderate base are as defined and X is halogen, preferably chlorine, C$_1$-C$_4$ alkyl—C(O)—O—, C$_1$-C$_4$ alkoxy—C(O)—O— or

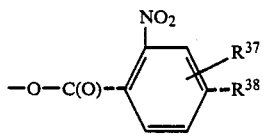

wherein R$^{37}$ and R$^{38}$ in this portion of the molecule are identical with those in the reactant shown above and the moderate base is as defined, preferably tri-C$_1$-C$_6$ alkylamine, alkali metal carbonate or alkali metal phosphate.

Generally, in step (1) mole amounts of the dione and substituted benzoyl reactant are used, along with a mole amount or excess of the base. The two reactants are combined in an organic solvent such as methylene chloride, toluene, ethyl acetate or dimethylformamide. The base or benzoyl reactant preferably are added to the reaction mixture with cooling. The mixture is stirred at 0° C.-50° C. until the reaction is substantially complete.

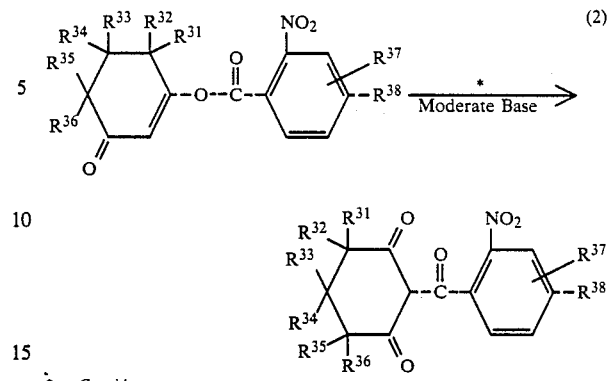

* = Cyanide source.

wherein the moderate base and R$^{31}$ through R$^{38}$ are as defined above.

Generally, in step (2) a mole of the enol ester intermediate is reacted with 1 to 4 moles of the base, preferably about 2 moles of moderate base and from 0.01 mole to about 0.5 mole or higher, preferably around 0.1 mole of the cyanide source (e.g., potassium cyanide or acetone cyanohydrin). The mixture is stirred in a reaction pot until the rearrangement is substantially complete at a temperature below 50° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of C$_2$-C$_5$ aliphatic aldehydes such as acetaldehyde, propionaldehyde, etc., cyanohydrins; zinc cyanide; tri(-lower alkyl)silyl cyanides, notably trimethyl silyl cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1-10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases such as tertiary amines and inorganic bases such as alkali metal carbonates and phosphates. Suitable tertiary amines include trialkylamines such as triethylamine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents may be usable in this process, depending on the nature of the acid chloride or the acylated product. A preferred solvent for this reaction is 1,2-dichloroethane. Other solvents which may be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

The above described substituted benzoyl chlorides can be prepared from the corresponding substituted benzoic acids according to the teaching of *Reagents for Organic Synthesis, Vol. I*, L. F. Fieser and M. Fieser, po. 767-769 (1967).

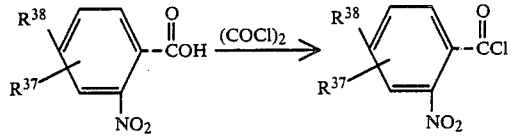

wherein $R^{37}$ and $R^{38}$ are as previously defined.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C. A. Buehler and D. F. Pearson, J. Wiley and Sons, (1970).

The following are three representative examples of the methods described therein.

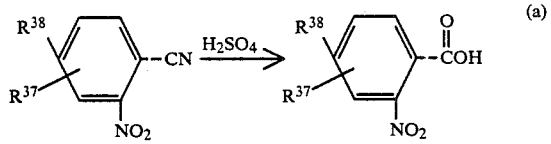

wherein $R^{37}$ and $R^{38}$ are as previously defined.

In reaction (a) the substituted benzonitrile is heated to reflux in aqueous sulfuric acid for several hours. The mixture is cooled and the reaction product is isolated by conventional techniques.

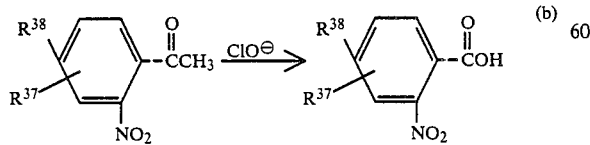

wherein $R^{37}$ and $R^{38}$ are as previously defined.

In reaction (b) the substituted acetophenone is heated to reflux for several hours in an aqueous hypochlorite solution. The mixture is cooled and the reaction product is isolated by conventional techniques.

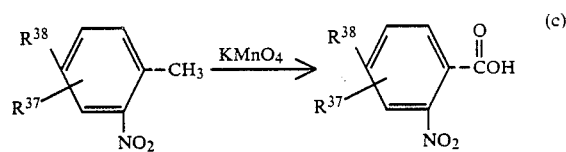

wherein $R^{37}$ and $R^{38}$ are as previously defined.

In reaction (c) the substituted toluene is heated to reflux in an aqueous solution of potassium permanganate for several hours. The solution is then filtered and the reaction product is isolated by conventional techniques.

The following examples teach the synthesis of representative compounds of Embodiment D and D' of this invention.

EXAMPLE 1-D,D'

2-(2'-Nitrobenzoyl)-1,3-cyclohexanedione

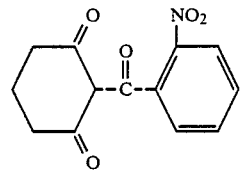

2-Nitrobenzoyl chloride (5.0 g, 27 mmol) and cyclohexanedione (3.0 g, 27 mmol) were dissolved in methylene chloride. Triethylamine (4.9 ml, 35 mmol) was added dropwise and the resulting solution stirred for one hour. The solution was washed with 2 normal hydrochloric acid (2N HCl), water, 5% potassium carbonate solution and saturated sodium chloride solution, dried over anhydrous magnesium sulfate (MgSO4) and concentrated under vacuum. The residue was dissolved in 20 ml acetonitrile. Triethylamine (1 equivalent) and potassium cyanide (40 mol %) were added and the solution stirred for one hour at room temperature. After dilution with ether, the solution was washed with 2N HCl and extracted with 5% potassium carbonate solution. The aqueous extract was acidified and ether was added. Filtration of the resulting mixture yielded 3.2 g of the desired compound (m.p. 132°-135° C.) which was identified by nuclear magnetic resonance spectroscopy, infrared spectroscopy and mass spectroscopy.

EXAMPLE 2-D,D'

2-(2'-Nitrobenzoyl)-5,5-dimethyl-1,3-cyclohexanedione

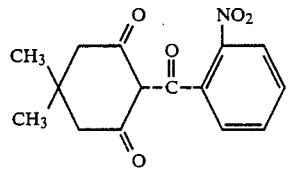

Triethylamine (3.4 ml, 25 mmol) was added dropwise to a methylene chloride solution of 2-nitrobenzoyl chloride (3.5 g, 19 mmol) and 5,5-dimethylcyclohexanedione (2.4 g, 19 mmol). After stirring for one hour at room temperature an additional 3 equivalents of triethylamine and 0.4 ml acetone cyanohydrin were added. The solution was stirred for 2.5 hours, then washed with 2N HCl and extracted with 5% potassium carbonate solution. The basic extracts were acidified with 2N HCl and extracted with ether. The ether portion was washed with saturated sodium chloride solution, dried over anhydrous magnesium sulfate and concentrated under vacuum. The residue was recrytallized from ethyl acetate yielding 2.0 g of the desired compound (m.p. 130°–133° C.) which was identified as such by nuclear magnetic resonance spectroscopy, infrared spectroscopy and mass spectroscopy.

The compounds of Embodiments E and E′ of the present invention can be prepared by the following two or three step general method.

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

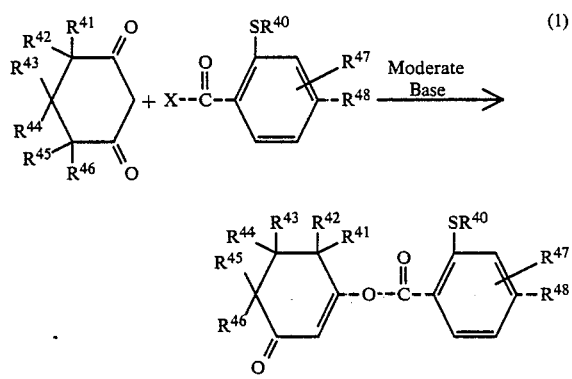

wherein moderate base, and $R^{40}$ through $R^{48}$ are defined herein, and X is halogen, preferably chlorine, $C_1$–$C_4$ alkyl—C(O)—O—, $C_1$–$C_4$ alkoxy—C(O)—O— or

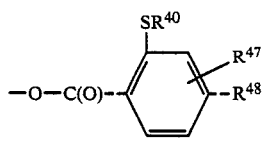

wherein $R^{40}$, $R^{47}$ and $R^{48}$ in this portion of the moledule are identical with those in the reactant shown above, and the moderate base is as defined, preferably tri-$C_1$–$C_6$ alkylamine, alkali metal carbonate or alkali metal phosphate.

Generally, in step (1) mole amounts of the dione and substituted benzoyl reactant are used, along with a mole amount or excess of the base. The two reactants are combined in an organic solvent such as methylene chloride, toluene, ethyl acetate or dimethylformamide. The base or benzoyl reactant preferably are added to the reaction mixture with cooling. The mixture is stirred at 0° C.–50° C. until the reaction is substantially complete.

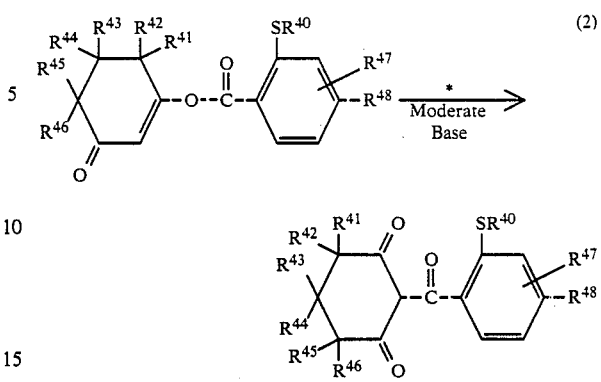

\* = Cyanide source as defined herein.
Moderate Base = As defined herein.

Generally, in step (2) a mole of the enol ester intermediate is reacted with 1 to 4 moles of the base, preferably about 2 moles of moderate base and from 0.01 mole to about 0.5 mole or higher, preferably around 0.1 mole of the cyanide source (e.g., potassium cyanide or acetonecyanohydrin). The mixture is stirred in a reaction pot until the rearrangement is substantially complete at a temperature below 50° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; cyanohydrins of benzaldehyde or of $C_2$–$C_5$ aliphatic aldehydes such as acetaldehyde, propionaldehyde, etc., cyanohydrins; zinc cyanide; tri(-lower alkyl)silyl cyanides, notably trimethyl silyl cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1–10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases such as tertiary amines and inorganic bases such as alkali metal carbonates and phosphates. Suitable tertiary amines include trialkylamines such as triethylamine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents may be usable in this process, depending on the nature of the acid chloride or the acylated product. A preferred solvent for this reaction is 1,2-dichloroethane. Other solvents which may be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

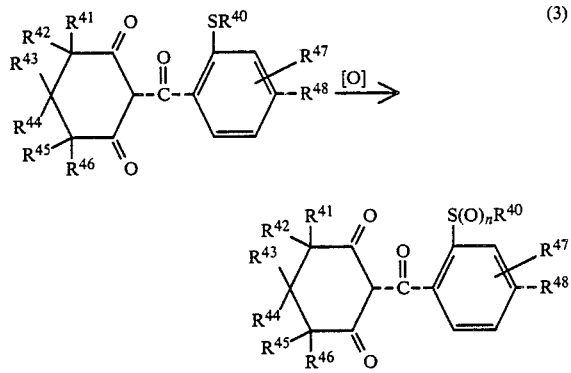
(3)

wherein n is 1 or 2.

Generally in step (3), a mole of the reaction product of step (2) is reacted with a slight mole or two mole excess of of an oxidizing agent such as m-chloroperbenzoic acid after being dissolved in a solvent such as methylene chloride. After completion of the reaction, the resulting mixture is stripped under vacuum. The residue is purified by silica gel chromatography to yield the desired product.

The above described substituted benzoyl chlorides can be prepared from the corresponding substituted benzoic acids according to the teaching of *Reagents for Organic Synthesis*, Vol. I, L. F. Fieser and M. Fieser, pp. 767–769 (1967).

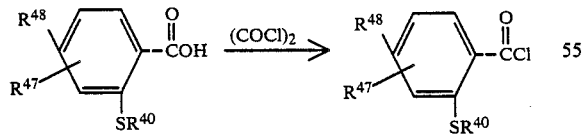

wherein $R^{40}$, $R^{47}$ and $R^{48}$ are as previously defined.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C. A. Buehler and D. F. Pearson, J. Wiley and Sons, (1970).

The following are three representative examples of the methods described therein.

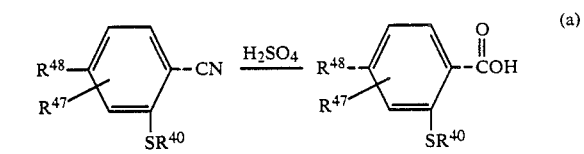
(a)

wherein $R^{40}$, $R^{47}$ and $R^{48}$ are as previously defined.

In reaction (a) the substituted benzonitrile is heated to reflux in aqueous sulfuric acid for several hours. The mixture is cooled and the reaction product is isolated by conventional techniques.

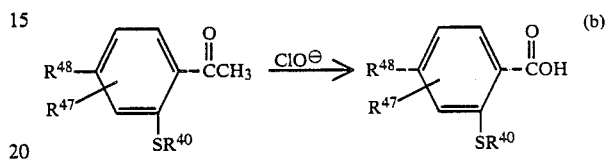
(b)

wherein $R^{40}$, $R^{47}$ and $R^{48}$ are as previously defined.

In reaction (b) the substituted acetophenone is heated to reflux for several hours in an aqueous hypochlorite solution. The mixture is cooled and the reaction product is isolated by conventional techniques.

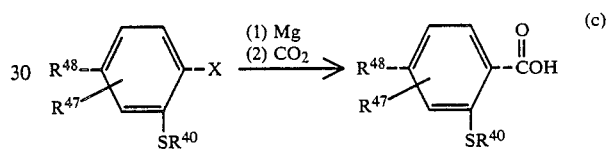
(c)

wherein $R^{40}$, $R^{47}$ and $R^{48}$ are as defined and X is chlorine, bromine or iodine.

In reaction (c) the substituted aromatic halide is allowed to react with magnesium in a solvent such as ether. The solution is then poured over crushed dry ice and the benzoic acid is isolated by conventional techniques.

The following examples teach the synthesis representative compounds of Embodiments E and E' of this invention.

EXAMPLE 1-E,E'

2-(2'-Methylthiobenzoyl)-4,4,6-trimethyl-1,3-cyclohexanedione

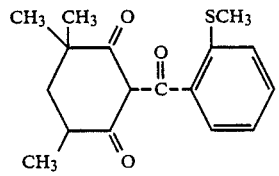

2-Methylthiobenzoyl chloride (7.2 g, 39 mmol) and 4,4,6-trimethylcyclohexanedione (5.0 g, 39 mmol) were dissolved in methylene chloride. Triethylamine (7.0 ml, 50 mmol) was added dropwise and the resulting solution stirred for one hour at room temperature. The solution was washed with 2 normal hydrochloric acid (2N HCl), 5% potassium carbonate solution (5% $K_2CO_3$) and saturated sodium chloride solution (brine), dried over anhydrous magnesium sulfate ($MgSO_4$) and concentrated under vacuum. The residue was dissolved in 20 ml acetonitrile. Triethylamine (2.5 equivalents)

and acetone cyanohydrin (0.4 ml) were added and the solution stirred for 45 minutes at room temperature. After dilution with ether, the solution was washed with 2N HCl and extracted with 5% $K_2CO_3$. The aqueous extract was acidified with hydrochloric acid and extracted with ether. The ether was washed with brine, dried ($MgSO_4$) and concentrated under vacuum. The residue was purified by trituration with ether, yielding 5.0 g of a viscous oil which was identified as the desired compound by nuclear magnetic resonance spectroscopy (nmr), infrared spectroscopy (ir) and mass spectroscopy (ms).

EXAMPLE 2-E,E'
2-(2'-Methanesulfonylbenzoyl)-4,4,6-trimethyl-1,3-cyclohexanedione

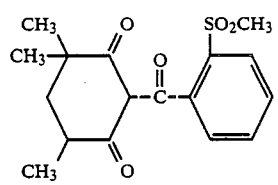

The benzoyl cyclohexanedione prepared in Example 1 (2.5 g, 7.9 mmol) was dissolved in 40 ml methylene chloride. m-Chloroperbenzoic acid (3.5 g, 16 mmol) was added and the resulting solution was stirred for 45 minutes. The solution was concentrated under vacuum. Purification of the residue by silica gel chromatography yielded 1.7 g of a viscous oil which was identified as the desired compound by nmr, ir and ms.

EXAMPLE 3-E,E'
2-(4'-Trifluoromethyl-2'-methanesulfinylbenzoyl)-4,4-dimethyl-1,3-cyclohexanedione

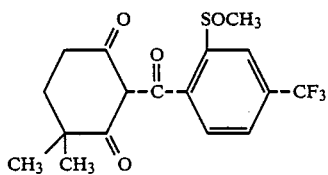

2-(4'-Trifluoromethyl-2'-methylthiobenzoyl)-4,4-dimethyl-1,3-cyclohexanedione (5.0 g, 14 mmol) (which was prepared according to the method of Example 1) was dissolved in 50 ml methylene chloride. A solution of m-chloroperbenzoic acid (2.4 g—80%, 14 mmol) in 50 ml methylene chloride was added dropwise and the resulting solution was stirred for three hours at room temperature. After concentration under vacuum, the residue was dissolved in ether and washed with 1% hydrochloric acid. A 5% copper(II) acetate solution was added to the ether fraction, followed by hexane. The liquid phase was decanted and the remaining gummy solid stirred with 6N HCl and ether. The ether layer was dried ($MgSO_4$) and concentrated to give 4.7 of a thick yellow solid. Purification on a centrifugally accelerated thin layer chromatograph (4 mm silica gel, 50:50:1 hexane:ethyl acetate:acetic acid-eluent) yielded 2.4 g of a viscous oil which was identified as the desired compound by nmr, ir and ms.

The compounds of Embodiments F and F' of the present invention can be prepared by the following two-step general method.

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

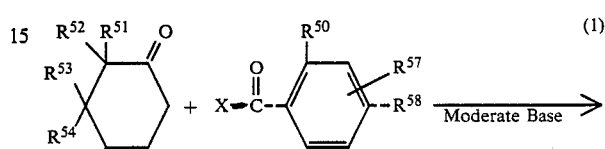 (1)

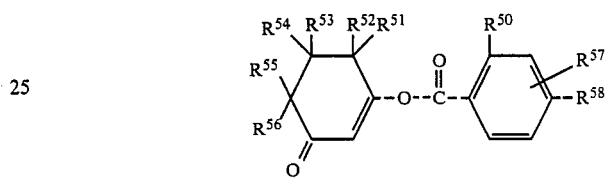

wherein $R^{50}$ through $R^{58}$ are as defined and X is halogen, preferably chlorine, $C_1$-$C_4$ alkyl—C(O)—O—, $C_1$-$C_4$ alkoxy—C(O)—O— or

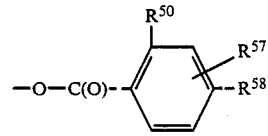

wherein $R^{50}$, $R^{57}$ and $R^{58}$ in this portion of the molecule are identical with those in the reactant shown above and the moderate base is as defined, preferably tri-$C_1$-$C_6$ alkylamine, alkali metal carbonate or alkali metal phosphate.

Generally, in step (1) mole amounts of the dione and substituted benzoyl reactant are used, along with a mole amount or excess of the base. The two reactants are combined in an organic solvent such as methylene chloride, toluene, ethyl acetate or dimethylformamide. The base or benzoyl reactant preferably are added to the reaction mixture with cooling. The mixture is stirred at 0° C.-50° C. until the reaction is substantially complete.

The reaction product is worked up by conventional techniques.

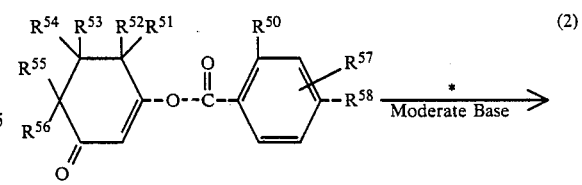 (2)

-continued

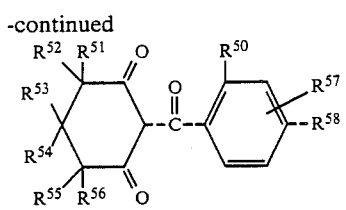

\* = Cyanide source.
Moderate base = as defined herein.

wherein $R^{50}$ through $R^{58}$ are as defined.

Generally, in step (2) a mole of the enol ester intermediate is reacted with 1 to 4 moles of the base, preferably about 2 moles of moderate base and from 0.01 mole to about 0.5 mole or higher, preferably around 0.1 mole of the cyanide source (e.g., potassium cyanide or acetone cyanohydrin). The mixture is stirred in a reaction pot until the rearrangement is substantially complete at a temperature below 80° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; cyanohydrins of benzaldehyde or of $C_2$–$C_5$ aliphatic aldehydes such as acetaldehyde, propionaldehyde, etc., cyanohydrins; zinc cyanide; tri(-lower alkyl) silyl cyanides, notably trimethyl silyl cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1–10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases such as tertiary amines and inorganic bases such as alkali metal carbonates and phosphates. Suitable tertiary amines include trialkylamines such as triethylamine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents may be usable in this process, depending on the nature of the acid chloride or the acylated product. A preferred solvent for this reaction is 1,2-dichloroethane. Other solvents which may be employed, depending on the reactants or products include toluene, acetonitrile, methylene chloride, ethyl acetate, dimethyl formamide, and methyl isobutyl ketone (MIBK).

In general, depending on the nature of the reactants and the cyanide source, the rearrangement may be conducted at temperatures up to about 50° C.

The above described substituted benzoyl chlorides can be prepared from the corresponding substituted benzoic acids according to the teaching of *Reagents for Organic Synthesis,* Vol. I, L. F. Fieser and M. Fieser, pp. 767–769 (1967).

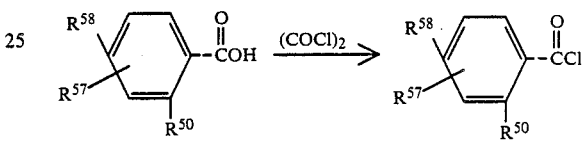

wherein $R^{50}$, $R^{57}$ and $R^{58}$ are as previously defined.

The substituted benzoic acids can be prepared by a wide variety of general methods according to the teaching of *The Chemistry of Carboxylic Acids and Esters,* S. Patai, editor, J. Wiley and Sons, New York, N.Y. (1969) and *Survey of Organic Synthesis,* C. A. Buehler and D. F. Pearson, J. Wiley and Sons, (1970).

The following are four representative examples of the methods described therein.

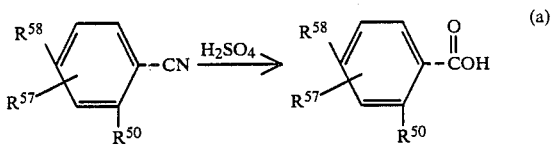

wherein $R^{50}$, $R^{57}$ and $R^{58}$ are as previously defined.

In reaction (a) the substituted benzonitrile is heated to reflux in aqueous sulfuric acid for several hours. The mixture is cooled and the reaction product is isolated by conventional techniques.

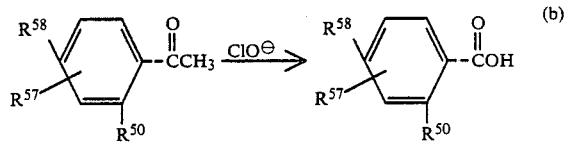

wherein $R^{50}$, $R^{57}$ and $R^{58}$ are as previously defined.

In reaction (b) the substituted acetophenone is heated to reflux for several hours in an aqueous hypochlorite solution. The mixture is cooled and the reaction is isolated by conventional techniques.

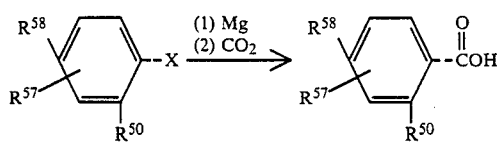

(c)

wherein $R^{50}$, $R^{57}$ and $R^{58}$ are as defined and X is chlorine, bromine or iodine.

The substituted aromatic halide is allowed to react with magnesium in a solvent such as ether. The solution is then poured over crushed dry ice and the benzoic acid is isolated by conventional techniques.

The following example teachs the synthesis of a representative compound of Embodiments F and F' of this invention.

EXAMPLE 1-F,F'

2-(4'-Bromo-2'-trifluoromethylbenzoyl)-4,4,6-trimethyl-1,3-cyclohexanedione

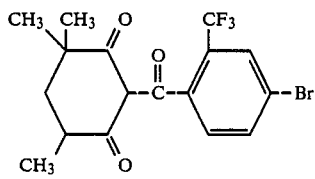

4-Bromo-2-trifluoromethylbenzoyl chloride (4.3 g, 15 mmol) and 4,4,6-trimethyl-1,3-cyclohexanedione (2.3 g, 15 mmol) were dissolved in 100 ml methylene chloride. The solution was cooled with an ice bath and triethylamine (2.1 ml, 15 mmol) in 10 ml methylene chloride was added dropwise. The ice bath was then removed and the resulting solution stirred for 30 minutes at room temperature. The solution was washed with 2N hydrochloric acid (2N HCl), 5% potassium carbonate solution (5% $K_2CO_3$) and saturated sodium chloride solution (brine), dried over anhydrous magnesium sulfate ($MgSO_4$) and concentrated under vacuum. The residue (5.1 g) was dissolved in 20 ml acetonitrile. Triethylamine (3.5 ml, 25 mmol) and 0.4 ml acetone cyanohydrin were added and the solution stirred for two hours at room temperature while protected by a drying tube (calcium sulfate). After dilution with ether, the solution was washed with 2N HCl and extracted with 5% $K_2CO_3$. The aqueous extract was acidified with concentrated hydrochloric acid and extracted with ether. The ether was washed with brine, dried ($MgSO_4$) and concentrated under vacuum. The resulting oil was purified on a silica gel column (80:20:1 hexane:ethyl acetate:acetic acid-eluent), yielding 1.5 g of a viscous oil which was identified as the desired compound by nuclear magnetic resonance spectroscopy, infrared spectroscopy and mass spectroscopy.

The compounds of Embodiment G and G' of the present invention can be prepared by the following two-step general method.

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

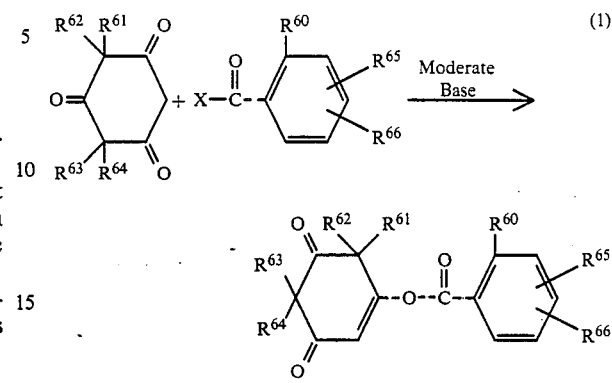

(1)

wherein $R^{60}$ through $R^{66}$ and moderate base are as defined and X is halogen, preferably chlorine, $C_1$–$C_4$ alkyl-C(O)—O—, $C_1$–$C_4$ alkoxy-C(O)—O— or

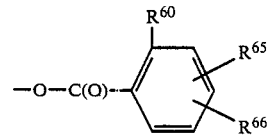

wherein $R^{60}$, $R^{65}$ and $R^{66}$ in this portion of the molecule are identical with those in the reactant shown above and the moderate base is as defined, preferably tri-$C_1$–$C_6$ alkylamine, alkali metal carbonate or alkali metal phosphate.

Generally, in step (1) mole amounts of the trione and substituted benzoyl reactant are used, along with a mole amount or excess of the base. The two reactants are combined in an organic solvent such as methylene chloride, toluene, ethyl acetate or dimethylformamide. The base or benzoyl reactant preferably is added to the reaction mixture with cooling. The mixture is stirred at 0° C.–50° C. until the reaction is substantially complete.

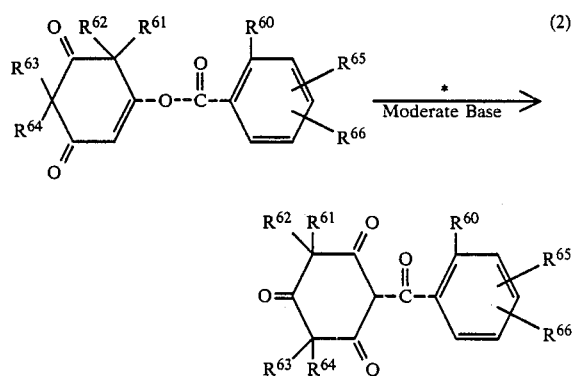

(2)

\* = Cyanide source.

wherein the moderate base and $R^{60}$ through $R^{66}$ are as defined above.

Generally, in step (2) a mole of the enol ester intermediate is reacted with 1 to 4 moles of the moderate base, preferably about 2 moles of moderate base and from 0.01 mole to about 0.5 mole or higher, preferably about 0.1 mole of the cyanide source (e.g., potassium cyanide or acetone cyanohydrin). The mixture is stirred in a reaction pot until the rearrangement is substantially complete at a temperature below 50° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of $C_2$-$C_5$ aliphatic aldehydes such as acetaldehyde, propionaldehyde, etc., cyanohydrins; zinc cyanide; tri(-lower alkyl) silyl cyanides, notably trimethyl silyl cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1-10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases, e.g., trialkylamines such as triethylamine and inorganic bases such as alkali metal carbonates and phosphates. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the crown ethers.

A number of different solvents are useful in this process, depending on the nature of the acid halide or the acylated product. A preferred solvent for this reaction is 1,2-dichloroethane. Other solvents which may be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

The above described substituted benzoyl chlorides can be prepared from the corresponding substituted benzoic acids according to the teaching of *Reagents for Organic Synthesis, Vol. I*, L. F. Fieser and M. Fieser, pp. 767-769 (1967).

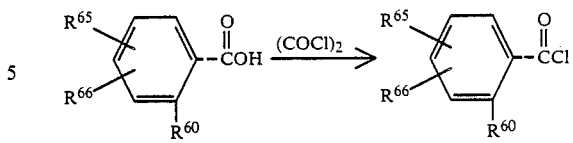

wherein $R^{60}$, $R^{65}$ and $R^{66}$ are as previously defined.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C. A. Buehler and D. F. Pearson, J. Wiley and Sons, (1970).

The following are three representative examples of the methods described therein.

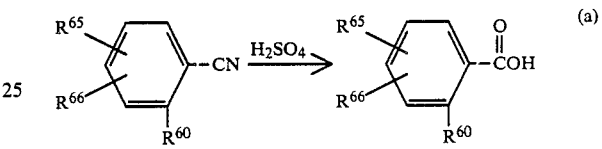

wherein $R^{60}$, $R^{65}$ and $R^{66}$ are as previously defined.

In reaction (a) the substituted benzonitrile is heated to reflux in aqueous sulfuric acid for several hours. The mixture is cooled and the reaction product is isolated by conventional techniques.

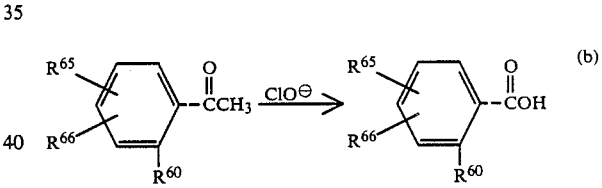

wherein $R^{60}$, $R^{65}$ and $R^{66}$ are as previously defined.

In reaction (b) the substituted acetophenone is heated to reflux for several hours in an aqueous hypochlorite solution. The mixture is cooled and the reaction product is isolated by conventional techniques.

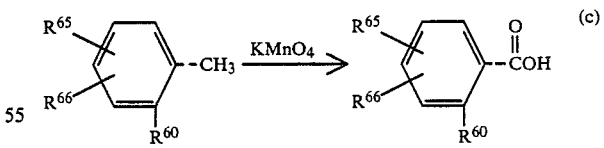

wherein $R^{60}$, $R^{65}$ and $R^{66}$ are as previously defined.

In reaction (c) the substituted toluene is heated to reflux in an aqueous solution of potassium permanganate for several hours. The solution is then filtered and the reaction product is isolated by conventional techniques.

The following example teaches the synthesis of a representative compound of Embodiment G and G' of this invention.

EXAMPLE 1-G,G'

2-(2'-Nitro-4'-chlorobenzoyl)-4,4,6,6-tetramethyl-1,3,5-cyclohexanetrione

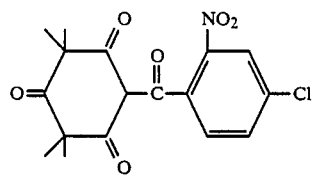

2-Nitro-4-chlorobenzoyl chloride (2.2 g, 10 mmol) and 4,4,6,6-tetramethyl-1,3,5-cyclohexanetrione (1.8 g, 10 mmol) were dissolved in methylene chloride. Triethylamine was added and the resulting solution stirred at room temperature for 30 minutes. The solution was washed with 1 normal hydrochloric acid (1N HCl), and saturated sodium chloride (brine), dried over anhydrous magnesium sulfate ($MgSO_4$) and concentrated under vacuum. The residue was dissolved in 20 ml acetonitrile. Triethylamine (5 ml, 3.5 equivalents) and acetone cyanohydrin (0.5 g, 0.6 equivalent) were added and the mixture stirred at room temperature for 4 hours. After dilution with ether, the solution was washed with 1N HCl and extracted with 5% $K_2CO_3$. The basic extract was acidified with HCl and extracted with ether. The ether extract was washed with brine, dried over $MgSO_4$ and concentrated under vacuum, yielding 2.2 g of crude product. This was recrystallized from benzene to remove syncarpic acid still present. Concentration of the mother liquor under vacuum gave 1.7 g of the desired product as an oil, which solidified on standing (m.p. 76°–82° C.). It was identified as such by nuclear magnetic resonance spectroscopy, infrared spectroscopy and mass spectroscopy.

The following are tables of certain selected compounds of Embodiments A–G' that are preparable according to the procedures described herein. Compound numbers are assigned to each compound and are used throughout the remainder of the application.

TABLE I-A

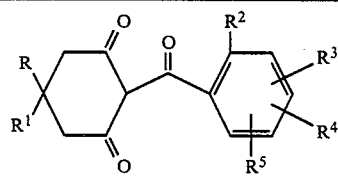

| Cmpd. No. | R | $R^1$ | $R^2$ | $R^3$ | $R^4$ | $R^5$ | $n_D^{30}$ or m.p. °C. |
|---|---|---|---|---|---|---|---|
| 1A | $CH_3$ | $CH_3$ | Cl | H | H | H | 1.5613 |
| 2A | $CH_3$ | $CH_3$ | Cl | H | 4-Cl | H | 1.5655 |
| 3A | $CH_3$ | $CH_3$ | Cl | H | H | 6-Cl | 103–108 |
| 4A* | H | H | Cl | H | 4-Cl | H | 138–140 |
| 5A | $CH_3$ | $CH_3$ | Br | H | H | H | |
| 6A | $CH_3$ | $CH_3$ | Cl | H | H | 5-Cl | 74–77 |
| 7A | H | H | Cl | H | H | 5-Cl | 104–107 |
| 8A | H | H | Br | H | H | H | 93–96 |
| 9A | H | H | Cl | H | H | H | 79–87 |
| 10A | H | H | I | H | H | H | 66–70 |
| 11A | H | H | Cl | H | 4-$NO_2$ | H | 118–122 |
| 12A | H | H | Cl | H | H | 6-Cl | 143–148 |
| 13A | H | H | Cl | H | H | 5-Br | 109–115 |
| 14A | H | H | I | 3-I | H | 5-I | 164–167 |
| 15A | H | H | Cl | H | H | 5-$CH_3$ | 60–65 |
| 16A | H | H | Cl | H | 4-$CH_3$ | H | 79–86 |
| 17A | H | H | Cl | H | 4-$CH_3O$ | H | 60–63 |
| 18A | H | H | Cl | 3-Cl | H | 6-Cl | |
| 19A | H | H | Cl | H | H | H | 77–80 |
| 20A | H | H | Cl | 3-Cl | H | H | 80–90 |
| 21A | H | H | Cl | H | H | 5-$CF_3$ | 74–75 |
| 22A | H | H | Cl | H | H | 5-$NO_2$ | 140–143 |
| 23A | H | H | Cl | 3-Cl | 4-Cl | H | 152–154 |
| 24A | H | H | Cl | 3-Cl | 4-$CH_3O$ | H | 169–170 |
| 25A | H | H | Cl | H | 4-Br | H | 104–107 |
| 26A | $CH_3$ | $CH_3$ | $CH_3O$ | H | H | H | 104–108 |
| 27A | H | H | Cl | H | 4-$CH_3$C(O)—NH | H | |
| 28A | H | H | Br | H | H | (a) | |
| 29A | H | H | $CH_3O$ | 3-$CH_3O$ | H | H | 75–79 |
| 30A | H | H | $CH_3O$ | H | H | 5-$CH_3O$ | 89–92 |
| 31A | H | H | Br | H | 4-$CH_3O$ | 5-$CH_3O$ | 92–96 |
| 32A | H | H | Br | H | (4)—$OCH_2O$—(5) | | 63–68 |
| 33A | $CH_3$ | $CH_3$ | Cl | 3-Cl | 4-Cl | H | 86–89 |
| 34A | H | H | Cl | 3-Cl | H | 5-Cl | |
| 35A | $CH_3$ | $CH_3$ | Cl | 3-Cl | H | 5-Cl | 105–109 |
| 36A | $CH_3$ | $CH_3$ | Cl | 3-Cl | 4-Cl | 5-Cl | 137–139 |
| 37A | H | H | Cl | 3-Cl | 4-Cl | 5-Cl | 106–110 |
| 38A | H | H | Cl | H | 4-Cl | 5-Cl | 108–111 |

TABLE I-A-continued

Structure: cyclohexane-1,3-dione with R and R¹ substituents at the 5-position, and at the 2-position a carbonyl group connected to a phenyl ring bearing R² (ortho), R³, R⁴, R⁵.

| Cmpd. No. | R | R¹ | R² | R³ | R⁴ | R⁵ | $n_D^{30}$ or m.p. °C. |
|---|---|---|---|---|---|---|---|
| 39A | CH(CH₃)₂O—C(=O)— | H | Cl | H | 4-Cl | H | |
| 40A | CH₃O—C(=O)— | H | Cl | H | 4-Cl | H | |
| 41A | CH(CH₃)₂ | H | Cl | H | 4-Cl | H | |
| 42A | CH(CH₃)₂ | H | Cl | 3-Cl | 4-Cl | H | |
| 43A | H | H | Cl | H | 4-F | H | |
| 44A | sodium salt of Compound No. 23 | | | | | | 85–94 |
| 45A | isopropylamine salt of Compound No. 23 | | | | | | 160–165 |
| 46A | triethylamine salt of Compound No. 23 | | | | | | 82–85 |
| 47A | potassium salt of Compound No. 23 | | | | | | 107–106 |
| 48A | triethanolammonium salt of Compound No. 39 | | | | | | |
| 49A | sodium salt of Compound No. 43 | | | | | | 60–63 |
| 50A | CH(CH₃)₂ | H | Cl | 3-CH₃O | 4-Br | H | |
| 51A | H | H | Cl | H | 4-CH₃SO₂— | H | 140–141 |
| 52A | H | CH₃ | Cl | H | 4-Cl | H | |
| 53A | i-C₄H₉ | H | Cl | H | 4-Cl | H | |
| 54A | i-C₃H₇ | H | Cl | 3-CH₃O | H | 4-CH₃SO₂— | H |
| 55A | CH₃ | CH₃ | Cl | H | 4-CH₃SO₂— | H | |
| 56A | CH₃ | CH₃ | Cl | 3-CH₃ | 4-Cl | H | |
| 57A | H | H | Cl | 3-CH₃ | 4-Cl | H | 56–64 |
| 58A | H | H | Cl | H | 4-C₂H₅SO₂— | H | 98–102 |
| 59A | H | H | Cl | 3-Cl | 4-C₂H₅SO₂— | H | 98–109 |
| 60A | H | H | Cl | H | 4-C₃H₇SO₂— | H | semi-solid |
| 61A | H | H | Cl | 3-CH₃O | 4-CH₃SO₂— | H | 48–59 |
| 62A | CH₃ | CH₃ | Cl | H | 4-n-C₃H₇SO₂— | H | semi-solid |
| 63A | H | H | Cl | 3-Cl | 4-n-C₃H₇SO₂— | H | 145–148.5 |
| 64A | H | H | Cl | 3-C₂H₅S | 4-C₂H₅SO₂— | H | oil |
| 65A | CH₃ | CH₃ | Cl | H | 4-C₂H₅SO₂— | H | 103–108 |
| 66A | CH₃ | CH₃ | Cl | 3-Cl | 4-C₂H₅SO₂— | H | 108–114 |
| 67A | i-C₃H₇ | H | Cl | H | 4-C₂H₅SO₂— | H | brown gum |
| 68A | H | H | Cl | 3-Cl | 4-CH₃SO₂— | H | 145–154 |
| 69A | i-C₃H₇ | H | Cl | 3-Cl | 4-CH₃SO₂— | H | brown gum |
| 70A | H | H | Br | H | 4-CH₃SO₂ | H | |
| 71A | H | H | Cl | H | 4-i-C₃H₇SO₂— | H | semi-solid |
| 72A | H | H | Cl | H | 4-CH₃S— | H | 74–77 |
| 73A | H | H | Cl | 3-Cl | 4-CH₃S— | H | |
| 74A | CH₃ | CH₃ | Cl | 3-Cl | 4-n-C₃H₇SO₂— | H | 120–123 |
| 75A | H | H | Cl | H | 4-n-C₄H₉SO₂— | H | semi-solid |
| 76A | CH₃ | CH₃ | Cl | H | 4-n-C₄H₉SO₂— | H | |
| 77A | H | H | Cl | 3-C₂H₅O | 4-CH₃SO₂— | H | semi-solid |
| 78A | H | H | Cl | 3-CH₃O | 4-n-C₃H₇SO₂— | H | golden gum |
| 79A | CH₃ | CH₃ | Cl | H | 4-i-C₃H₇SO₂— | H | 125–128 |
| 80A | CH(CH₃)₂— | H | CH₃O | 3-Cl | 5-Cl | H | |
| 81A | HB | H | Cl | 3-CH₃O | 4-Br | H | 101–111 |
| 82A | H | H | Cl | 3-CH₃ | 4-Cl | H | 56–64 |
| 83A | H | H | Cl | H | 4-Cl | 5-CH₃O | softens >70 |
| 84A | CH(CH₃)₂ | H | Cl | 3-n-C₃H₇O | 4-Br | H | |
| 85A | H | H | Cl | 3-C₂H₅O | 4-Br | H | 101–104 |
| 86A | H | H | Cl | H | 4-i-C₄H₉SO₂ | H | 136–140 |
| 87A | CH₃ | CH₃ | Cl | H | 4-i-C₃H₇SO₂ | H | |
| 88A | H | H | Cl | 3-Cl | 4-i-C₃H₇SO₂ | H | 173–176 |
| 89A | H | H | Cl | 3-Cl | 4-n-C₄H₉SO₂ | H | 135–138 |
| 90A | H | H | Cl | 3-C₂H₅O | 4-C₂H₅SO₂ | H | gum |
| 91A | H | H | Cl | 3-CH₃O | 4-C₂H₅SO₂ | H | gum |
| 92A | H | H | Cl | 3-Cl | 4-C₂H₅S | H | 91–94 |
| 93A | H | H | Cl | 3-C₂H₅S | 4-n-C₃H₇SO₂ | H | oil |
| 94A | H | H | Cl | 3-C₂H₅S | 4-C₂H₅S | H | oil |
| 95A | H | H | Cl | H | 4-(CH₃)₂NSO₂ | H | |
| 96A | H | H | Cl | 3-C₂H₅O | 4-n-C₃H₇SO₂ | H | |
| 97A | H | H | Cl | 3-n-C₃H₇O | 4-C₂H₅SO₂ | H | oil |
| 98A | CH₃ | CH₃ | Cl | H | 4-(CH₃)₂NSO₂ | H | oil |
| 99A | H | H | Cl | H | 4-(C₂H₅)₂NSO₂ | H | 90–92 |
| 100A | CH₃ | CH₃ | Cl | H | 4-(C₂H₅)₂NSO₂ | H | |
| 101A | H | H | Cl | H | 4-C₂H₅S | H | |
| 102A | H | H | Cl | H | 4-n-C₃H₇S | H | |
| 103A | H | H | Cl | H | 4-i-C₃H₇S | H | |

TABLE I-A-continued

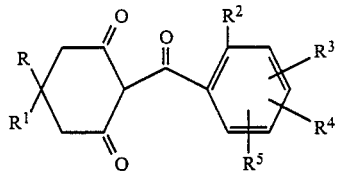

| Cmpd. No. | R | R¹ | R² | R³ | R⁴ | R⁵ | $n_D^{30}$ or m.p. °C. |
|---|---|---|---|---|---|---|---|
| 104A | H | H | Cl | H | 4-C₂H₅SO | H | |
| 105A | H | H | CH₃O | H | 4-NO₂ | H | semi-solid |
| 106A | H | H | Cl | 3-n-C₃H₇O | 4-Br | H | |
| 107A | H | H | Cl | 3-n-C₃H₇O | 4-CH₃SO₂ | H | 96–100 |
| 108A | H | H | Cl | 3-allyloxy | 4-CH₃SO₂ | H | semi-solid |
| 109A | H | H | Cl | 3-CH₃C(O)NH | 4-Cl | H | 155–160 |
| 110A | H | H | Cl | 3-Cl | 4-n-C₃H₇S | H | |
| 111A | H | H | Cl | 3-CH₃O | 4-NO₂ | H | 150–153 |
| 112A | H | H | Cl | 3-allyloxy | 4-C₂H₅SO₂ | H | |
| 113A | H | H | Cl | 3-CH₂BrCHBrCH₂O | 4-C₂H₅SO₂ | H | |
| 114A | H | H | Cl | 3-n-C₄H₉O | 4-C₂H₅SO₂ | H | gum |
| 115A | H | H | Cl | 3-i-C₄H₉O | 4-C₂H₅SO₂ | H | |
| 116A | H | H | Cl | H | 4-allylthio | H | |
| 117A | CH₃ | CH₃ | Cl | H | 4-NO₂ | H | |
| 118A | H | H | Cl | 3-CH₃C(O)N(CH₃) | 4-Cl | H | |
| 119A | H | H | Cl | 3-i-C₃H₇O | 4-C₂H₅SO₂ | H | |
| 120A | H | H | Cl | 3-CH₂ClCH₂CH₂O | 4-C₂H₅SO₂ | H | gum |
| 121A | H | H | Cl | H | 4-t-C₄H₉S | H | |
| 122A | H | H | Cl | 3-CH₃O | 4-C₂H₅S | H | |
| 123A | H | H | Cl | H | 4-CF₃ | H | |
| 124A | H | H | Cl | H | 4-Cl | 6-Cl | |
| 124A | H | H | Cl | 3-CH₃C(O)N(CH₃) | H | H | 131–135 |
| 126A | H | H | Cl | 3-CH₃C(O)NH | H | H | |
| 127A | H | H | Cl | 3-(CH₃)₂N | 4-Cl | H | |
| 128A | CH₃ | H | Cl | 3-CH₃O | 4-CH₃SO₂ | H | 117–122 |
| 129A | H | H | Cl | H | 4-C₂H₅SO₂ | H | |
| 130A | H | H | Br | H | H | H | |
| 131A | H | H | Br | H | 4-C₂H₅OC(O) | H | |
| 132A | H | H | Cl | H | 4-CN | H | 183–184 |
| 133A | H | H | Cl | 3-CH₃C(O)NH | H | 6-NO₂ | |
| 134A | H | H | Cl | 3-(CH₃)₂N | H | H | |
| 135A | H | H | Cl | 3-Cl | 4-ClCH₂CH₂SO₂ | H | |

* = prepared in Example 1-A.

(a) = 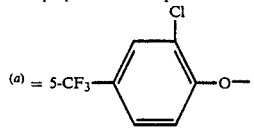

TABLE I-B

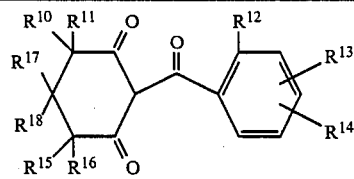

| Compound Number | R¹⁰ | R¹¹ | R¹² | R¹³ | R¹⁴ | R¹⁵ | R¹⁶ | R¹⁷ | R¹⁸ |
|---|---|---|---|---|---|---|---|---|---|
| 1B | C₂H₅—O—C(O)— | H | Cl | H | 4-Cl | H | H | H | H |
| 2B | C₂H₅—O—C(O)— | CH₃ | Cl | H | 4-Cl | H | H | H | H |
| 3B | triethanolammonium salt of Compound No. 2 | | | | | | | | |
| 4B | triethanolammonium salt of Compound No. 7 | | | | | | | | |
| 5B | C₂H₅—O—C(O)— | CH₃ | Cl | 3-Cl | 4-Cl | H | H | H | H |
| 6B | triethanolammonium salt of Compound No. 5 | | | | | | | | |

TABLE I-B-continued

| Compound Number | R10 | R11 | R12 | R13 | R14 | R15 | R16 | R17 | R18 |
|---|---|---|---|---|---|---|---|---|---|
| 7B[a] | CH3 | CH3 | Cl | H | 4-Cl | H | H | H | H |
| 8B | CH3 | CH3 | Cl | H | 4-Cl | CH3 | H | H | H |
| 9B | CH3 | n-C3H7 | Cl | H | 4-Cl | H | H | H | H |
| 10B | CH3 | H | Cl | H | 4-Cl | H | H | H | H |
| 11B | CH3 | H | Cl | H | 4-Cl | CH3 | H | H | H |
| 12B | —C5H10— | | Cl | H | 4-Cl | H | H | H | H |
| 13B | CH3 | CH3 | Cl | 3-Cl | 4-Cl | H | H | H | H |
| 14B | CH3 | CH3 | Cl | 3-Cl | 4-Cl | CH3 | H | H | H |
| 15B | i-C3H7 | H | Cl | 3-Cl | 4-Cl | H | H | H | H |
| 16B | CH3 | CH3 | Cl | H | 4-CH3SO2 | H | H | H | H |
| 17B | CH3 | CH3 | Cl | H | 4-CH3SO2 | CH3 | H | H | H |
| 18B | CH3 | H | Cl | H | 4-CH3SO2 | H | H | H | H |
| 19B | CH3 | CH3 | Cl | 3-Cl | 4-CH3SO2 | H | H | H | H |
| 20B | CH3 | CH3 | Cl | 3-Cl | 4-C2H5SO2 | H | H | H | H |
| 21B | CH3 | CH3 | Cl | H | 4-C2H5SO2 | H | H | H | H |
| 22B | CH3 | CH3 | Cl | H | 4-C2H5SO2 | CH3 | H | H | H |
| 23B | CH3 | CH3 | Cl | 3-OCH3 | 4-C2H5SO2 | H | H | H | H |
| 24B | CH3 | CH3 | Cl | 3-OCH3 | 4-CH3SO2 | H | H | H | H |
| 25B | CH3 | CH3 | Cl | 3-CH3 | 4-Cl | H | H | H | H |
| 26B | CH3 | CH3 | Cl | 3-OCH3 | 4-Cl | H | H | H | H |
| 27B | CH3 | C2H5 | Cl | H | 4-Cl | H | H | H | H |
| 28B | CH3 | CH3 | Cl | H | H | H | H | H | H |
| 29B | CH3 | CH3 | Cl | 3-OCH3 | 4-Br | H | H | H | H |
| 30B | CH3 | CH3 | Cl | H | 4-Br | H | H | H | H |
| 31B | CH3 | C2H5 | Cl | 3-Cl | 4-Cl | H | H | H | H |
| 32B | n-C3H7 | H | Cl | H | 4-Cl | H | H | H | H |
| 33B | C2H5OC(O)— | n-C3H7 | Cl | H | 4-Cl | H | H | H | H |
| 34B | CH3 | CH3 | Cl | H | 4-i-C3H7SO2 | H | H | H | H |
| 35B | CH3 | CH3 | Cl | 3-i-C3H7O | 4-Br | H | H | H | H |
| 36B | CH3 | CH3 | Cl | H | 6-F | H | H | H | H |
| 37B | i-C3H7 | H | Cl | 3-Cl | 4-Cl | H | H | H | H |
| 38B | CH3 | CH3 | Cl | 3-OC2H5 | 4-Br | CH3 | H | H | H |
| 39B | i-C3H7OC(O) | H | Cl | H | 4-Cl | H | H | H | H |
| 40B | C2H5OC(O)— | n-C3H7 | Cl | H | 4-Cl | H | H | H | H |
| 41B | —C5H10— | | Cl | H | 4-Cl | H | H | H | H |
| 42B | CH3 | CH3 | Cl | H | 4-Cl | H | H | CH3 | H |
| 43B | CH3 | CH3 | Cl | H | 4-n-C3H7SO2 | H | H | H | H |
| 44B | CH3 | CH3 | Cl | 3-Cl | 4-n-C3H7SO2 | H | H | H | H |
| 45B | CH3 | CH3 | CH3O | 3-CH3O | H | H | H | H | H |
| 46B | CH3 | CH3 | CH3O | H | 4-Cl | H | H | H | H |
| 47B | CH3 | CH3 | Cl | H | 4-Br | CH3 | H | H | H |
| 48B | CH3 | CH3 | Br | H | H | H | H | H | H |
| 49B | CH3 | CH3 | I | H | H | H | H | H | H |
| 50B | CH3 | CH3 | F | H | H | H | H | H | H |
| 51B | CH3 | CH3 | CH3O | H | H | H | H | H | H |
| 52B | CH3 | CH3 | Cl | 3-allyloxy | 4-Br | H | H | H | H |
| 53B | CH3 | CH3 | Cl | H | 4-CH3SO2 | H | H | CH3 | H |
| 54B | CH3 | CH3 | Cl | 3-CH3O | 4-Br | CH3 | H | H | H |
| 55B | CH3 | CH3 | Br | H | 4-CN | H | H | H | H |
| 56B | CH3 | CH3 | Cl | H | 4N(CH3)SO2CF3 | H | H | H | H |
| 57B | CH3 | CH3 | Cl | 3-NO2 | H | H | H | H | H |
| 58B | CH3 | CH3 | C2H5O | H | 4-Cl | H | H | H | H |
| 59B | CH3 | CH3 | Cl | H | 4-i-C4H9SO2 | H | H | H | H |
| 60B | CH3 | CH3 | Cl | 3-C2H5O | 4-CH3SO2 | H | H | H | H |
| 61B | CH3 | CH3 | Cl | 3-CH3O | 4-C2H5SO2 | H | H | H | H |
| 62B | CH3 | CH3 | Cl | H | 4-n-C4H9SO2 | H | H | H | H |
| 63B | CH3 | CH3 | Cl | 3-Cl | 4-n-C4H9SO2 | CH3 | H | H | H |
| 64B | CH3 | CH3 | Cl | 3-Cl | 4-C2H5SO2 | CH3 | H | H | H |
| 65B | CH3 | CH3 | Cl | H | 4-F | H | H | H | H |
| 66B | CH3 | H | Cl | 3-CH3O | 4-Br | H | H | H | H |
| 67B | CH3 | CH3 | Cl | 3-CH3O | H | H | H | H | H |
| 68B | CH3 | CH3 | Cl | 3-C2H5S | 4-n-C3H7SO2 | H | H | H | H |
| 69B | CH3 | CH3 | Cl | 3-C2H5S | 4-C2H5S | H | H | H | H |
| 70B | CH3 | CH3 | Cl | 3-C2H5S | 4-C2H5SO2 | H | H | H | H |
| 71B | CH3 | CH3 | Cl | 3-C2H5S | 4-CH3SO2 | H | H | H | H |
| 72B | CH3 | CH3 | Cl | Cl | 4-i-C3H7SO2 | H | H | H | H |
| 73B | CH3 | CH3 | Cl | 3-Cl | 4-n-C4H9SO2 | H | H | H | H |

TABLE I-B-continued

![structure with R10, R11 on one carbon, R17, R18, R15, R16 on cyclohexane-1,3-dione ring; carbonyl linking to phenyl ring with R12, R13, R14 substituents]

| Compound Number | R¹⁰ | R¹¹ | R¹² | R¹³ | R¹⁴ | R¹⁵ | R¹⁶ | R¹⁷ | R¹⁸ |
|---|---|---|---|---|---|---|---|---|---|
| 74B | CH₃ | CH₃ | Cl | 3-C₂H₅O | 4-C₂H₅SO₂ | H | H | H | H |
| 75B | CH₃ | CH₃ | Cl | 3-C₂H₅O | 4-Br | H | H | H | H |
| 76B | CH₃ | CH₃ | Cl | 3-C₂H₅O | 4-n-C₃H₇SO₂ | H | H | H | H |
| 77B | CH₃ | CH₃ | Cl | 3-n-C₃H₇O | 4-C₂H₅SO₂ | H | H | H | H |
| 78B | CH₃ | CH₃ | Cl | H | 4-(CH₃)₂NHO₂ | H | H | H | H |
| 79B | CH₃ | CH₃ | Cl | 3-CH₃S | 4-C₂H₅SO₂ | H | H | H | H |
| 80B | CH₃ | CH₃ | Cl | 3-Cl | 4-C₂H₅S | H | H | H | H |
| 81B | CH₃ | CH₃ | Cl | H | 4-C₂H₅S | H | H | H | H |
| 82B | CH₃ | CH₃ | Cl | H | 4-(C₂H₅)₂NSO₂ | H | H | H | H |
| 83B | CH₃ | CH₃ | Cl | H | 4-n-C₃H₇SO₂ | H | H | H | H |
| 84B | CH₃ | CH₃ | Cl | H | 4-n-C₃H₇S | CH₃ | H | H | H |
| 85B | CH₃ | CH₃ | Cl | H | 4-C₂H₅S(O) | H | H | H | H |
| 86B | CH₃ | CH₃ | Cl | H | 4-i-C₃H₇S | H | H | H | H |
| 87B | CH₃ | CH₃ | Cl | 3-Cl | 4-n-C₃H₇S | H | H | H | H |
| 88B | CH₃ | CH₃ | Cl | H | 4-t-C₄H₉SO₂ | H | H | H | H |
| 89B | CH₃ | CH₃ | Cl | H | 4-i-C₃H₇S | CH₃ | H | H | H |
| 90B | CH₃ | CH₃ | Cl | H | 4-n-C₃H₇SO₂ | CH₃ | H | H | H |
| 91B | CH₃ | CH₃ | Cl | * | 4-Cl | H | H | H | H |
| 92B | CH₃ | CH₃ | Cl | H | 4-CH₂=CH—CH₂S | H | H | H | H |
| 93B | CH₃ | CH₃ | Cl | 3-C₂H₅O | 4-C₂H₅S | H | H | H | H |
| 94B | CH₃ | CH₃ | Cl | 3-Cl | 4-CH₃S | CH₃ | H | H | H |
| 95B | CH₃ | CH₃ | Cl | H | 4-CH₃S | H | H | H | H |
| 96B | CH₃ | CH₃ | Cl | 3-i-C₃H₇O | 4-C₂H₅SO₂ | H | H | H | H |
| 97B | CH₃ | CH₃ | Cl | 3-CH₃O | 4-C₂H₅S | H | H | H | H |
| 98B | CH₃ | CH₃ | Cl | ** | 4-Cl | H | H | H | H |
| 99B | CH₃ | CH₃ | Cl | ** | H | H | H | H | H |
| 100B | CH₃ | CH₃ | Cl | 3-Cl | 4-CH₃S | H | H | H | H |
| 101B | CH₃ | CH₃ | CH₃O | H | 4-NO₂ | H | H | H | H |
| 102B | CH₃ | CH₃ | CH₃O | H | 4-CF₃ | H | H | H | H |
| 103B | CH₃ | CH₃ | Cl | H | 4-n-C₃H₇SO | H | H | H | H |
| 104B | CH₃ | CH₃ | Cl | H | 4-n-C₃H₇SO | CH₃ | H | H | H |

The following additional compounds can be prepared by the general method hereinbefore taught.

| R¹⁰ | R¹¹ | R¹² | R¹³ | R¹⁴ | R¹⁵ | R¹⁶ | R¹⁷ | R¹⁸ |
|---|---|---|---|---|---|---|---|---|
| CH₃ | n-C₃H₇ | Cl | H | 4-Cl | CH₃ | H | H | H |
| CH₃ | n-C₄H₉ | Cl | H | 4-Cl | H | H | H | H |
| CH₃ | n-C₄H₉ | Cl | H | 4-Cl | CH₃ | H | H | H |
| C₂H₅ | H | Cl | H | 4-Cl | H | H | H | H |
| C₂H₅ | H | Cl | H | 4-Cl | CH₃ | H | H | H |
| n-C₄H₉ | H | Cl | H | 4-Cl | H | H | H | H |
| n-C₄H₉ | H | Cl | H | 4-Cl | CH₃ | H | H | H |
| i-C₃H₇ | H | Cl | H | 4-Cl | H | H | H | H |
| i-C₃H₇ | H | Cl | H | 4-Cl | CH₃ | H | H | H |
| —C₅H₁₀— | | Cl | H | 4-Cl | CH₃ | H | H | H |
| CH₃ | n-C₃H₇ | Cl | 3-Cl | 4-Cl | H | H | H | H |
| CH₃ | n-C₃H₇ | Cl | 3-Cl | 4-Cl | CH₃ | H | H | H |
| CH₃ | n-C₄H₉ | Cl | 3-Cl | 4-Cl | H | H | H | H |
| CH₃ | n-C₄H₉ | Cl | 3-Cl | 4-Cl | CH₃ | H | H | H |
| CH₃ | H | Cl | 3-Cl | 4-Cl | H | H | H | H |
| CH₃ | H | Cl | 3-Cl | 4-Cl | CH₃ | H | H | H |
| C₂H₅ | H | Cl | 3-Cl | 4-Cl | H | H | H | H |
| C₂H₅ | H | Cl | 3-Cl | 4-Cl | CH₃ | H | H | H |
| n-C₄H₉ | H | Cl | 4-Cl | H | H | H | H | |
| n-C₄H₉ | H | Cl | 3-Cl | 4-Cl | CH₃ | H | H | H |
| —C₅H₁₀— | | Cl | 3-Cl | 4-Cl | H | H | H | |
| —C₅H₁₀— | | Cl | 3-Cl | 4-Cl | CH₃ | H | H | H |
| CH₃ | n-C₃H₇ | Cl | H | 4-CH₃SO₂ | H | H | H | |
| CH₃ | n-C₃H₇ | Cl | H | 4-CH₃SO₂ | CH₃ | H | H | H |
| CH₃ | n-C₄H₉ | Cl | H | 4-CH₃SO₂ | H | H | H | H |
| CH₃ | n-C₄H₉ | Cl | H | 4-CH₃SO₂ | CH₃ | H | H | H |
| CH₃ | H | Cl | H | 4-CH₃SO₂ | CH₃ | H | H | H |
| C₂H₅ | H | Cl | H | 4-CH₃SO₂ | H | H | H | H |
| C₂H₅ | H | Cl | H | 4-CH₃SO₂ | CH₃ | H | H | H |
| n-C₄H₉ | H | Cl | H | 4-CH₃SO₂ | H | H | H | H |
| n-C₄H₉ | H | Cl | H | 4-CH₃SO₂ | CH₃ | H | H | H |
| i-C₃H₇ | H | Cl | H | 4-CH₃SO₂ | H | H | H | |
| i-C₃H₇ | H | Cl | H | 4-CH₃SO₂ | CH₃ | H | H | |
| —C₅H₁₀— | | Cl | H | 4-CH₃SO₂ | H | H | H | H |
| —C₅H₁₀— | | Cl | H | 4-CH₃SO₂ | CH₃ | H | H | H |
| CH₃ | n-C₃H₇ | Cl | 3-Cl | 4-CH₃SO₂ | H | H | H | H |
| CH₃ | n-C₃H₇ | Cl | 3-Cl | 4-CH₃SO₂ | CH₃ | H | H | H |

TABLE I-B-continued

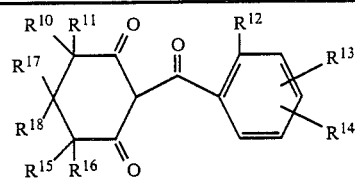

| Compound Number | R10 | R11 | R12 | R13 | R14 | R15 | R16 | R17 | R18 |
|---|---|---|---|---|---|---|---|---|---|
| | CH$_3$ | n-C$_4$H$_9$ | Cl | 3-Cl | 4-CH$_3$SO$_2$ | H | H | H | H |
| | CH$_3$ | n-C$_4$H$_9$ | Cl | 3-Cl | 4-CH$_3$SO$_2$ | CH$_3$ | H | H | H |
| | CH$_3$ | H | Cl | 3-Cl | 4-CH$_3$SO$_2$ | H | H | H | H |
| | CH$_3$ | H | Cl | 3-Cl | 4-CH$_3$SO$_2$ | CH$_3$ | H | H | H |
| | C$_2$H$_5$ | H | Cl | 3-Cl | 4-CH$_3$SO$_2$ | H | H | H | H |
| | C$_2$H$_5$ | H | Cl | 3-Cl | 4-CH$_3$SO$_2$ | CH$_3$ | H | H | H |
| | n-C$_4$H$_9$ | H | Cl | 3-Cl | 4-CH$_3$SO$_2$ | H | H | H | H |
| | n-C$_4$H$_9$ | H | Cl | 3-Cl | 4-CH$_3$SO$_2$ | CH$_3$ | H | H | H |
| | i-C$_3$H$_7$ | H | Cl | 3-Cl | 4-CH$_3$SO$_2$ | H | H | H | H |
| | i-C$_3$H$_7$ | H | Cl | 3-Cl | 4-CH$_3$SO$_2$ | CH$_3$ | H | H | H |
| | —C$_5$H$_{10}$— | | Cl | 3-Cl | 4-CH$_3$SO$_2$ | H | H | H | H |
| | —C$_5$H$_{10}$— | | Cl | 3-Cl | 4-CH$_3$SO$_2$ | CH$_3$ | H | H | H |
| | CH$_3$ | n-C$_3$H$_7$ | Cl | 3-Cl | 4-C$_2$H$_5$SO$_2$ | H | H | H | H |
| | CH$_3$ | n-C$_3$H$_7$ | Cl | 3-Cl | 4-C$_2$H$_5$SO$_2$ | CH$_3$ | H | H | H |
| | CH$_3$ | n-C$_4$H$_9$ | Cl | 3-Cl | 4-C$_2$H$_5$SO$_2$ | H | H | H | H |
| | CH$_3$ | n-C$_4$H$_9$ | Cl | 3-Cl | 4-C$_2$H$_5$SO$_2$ | CH$_3$ | H | H | H |
| | CH$_3$ | H | Cl | 3-Cl | 4-C$_2$H$_5$SO$_2$ | H | H | H | H |
| | CH$_3$ | H | Cl | 3-Cl | 4-C$_2$H$_5$SO$_2$ | CH$_3$ | H | H | H |
| | C$_2$H$_5$ | H | Cl | 3-Cl | 4-C$_2$H$_5$SO$_2$ | H | H | H | H |
| | C$_2$H$_5$ | H | Cl | 3-Cl | 4-C$_2$H$_5$SO$_2$ | CH$_3$ | H | H | H |
| | n-C$_4$H$_9$ | H | Cl | 3-Cl | 4-C$_2$H$_5$SO$_2$ | H | H | H | H |
| | n-C$_4$H$_9$ | H | Cl | 3-Cl | 4-C$_2$H$_5$SO$_2$ | CH$_3$ | H | H | H |
| | i-C$_3$H$_7$ | H | Cl | 3-Cl | 4-C$_2$H$_5$SO$_2$ | H | H | H | H |
| | i-C$_3$H$_7$ | H | Cl | 3-Cl | 4-C$_2$H$_5$SO$_2$ | CH$_3$ | H | H | H |
| | —C$_5$H$_{10}$— | | Cl | 3-Cl | 4-C$_2$H$_5$SO$_2$ | H | H | H | H |
| | —C$_5$H$_{10}$— | | Cl | 3-Cl | 4-C$_2$H$_5$SO$_2$ | CH$_3$ | H | H | H |
| | CH$_3$ | n-C$_3$H$_7$ | Cl | H | 4-C$_2$H$_5$SO$_2$ | H | H | H | H |
| | CH$_3$ | n-C$_3$H$_7$ | Cl | H | 4-C$_2$H$_5$SO$_2$ | CH$_3$ | H | H | H |
| | CH$_3$ | n-C$_4$H$_9$ | Cl | H | 4-C$_2$H$_5$SO$_2$ | H | H | H | H |
| | CH$_3$ | n-C$_4$H$_9$ | Cl | H | 4-C$_2$H$_5$SO$_2$ | CH$_3$ | H | H | H |
| | CH$_3$ | H | Cl | H | 4-C$_2$H$_5$SO$_2$ | H | H | H | H |
| | CH$_3$ | H | Cl | H | 4-C$_2$H$_5$SO$_2$ | CH$_3$ | H | H | H |
| | C$_2$H$_5$ | H | Cl | H | 4-C$_2$H$_5$SO$_2$ | H | H | H | H |
| | C$_2$H$_5$ | H | Cl | H | 4-C$_2$H$_5$SO$_2$ | CH$_3$ | H | H | H |
| | n-C$_4$H$_9$ | H | Cl | H | 4-C$_2$H$_5$SO$_2$ | H | H | H | H |
| | n-C$_4$H$_9$ | H | Cl | H | 4-C$_2$H$_5$SO$_2$ | CH$_3$ | H | H | H |
| | i-C$_3$H$_7$ | H | Cl | H | 4-C$_2$H$_5$SO$_2$ | H | H | H | H |
| | i-C$_3$H$_7$ | H | Cl | H | 4-C$_2$H$_5$SO$_2$ | CH$_3$ | H | H | H |
| | —C$_5$H$_{10}$— | | Cl | H | 4-C$_2$H$_5$SO$_2$ | H | H | H | H |
| | —C$_5$H$_{10}$— | | Cl | H | 4-C$_2$H$_5$SO$_2$ | CH$_3$ | H | H | H |
| | CH$_3$ | CH$_3$ | Cl | 3-OCH$_3$ | 4-C$_2$H$_5$SO$_2$ | CH$_3$ | H | H | H |
| | CH$_3$ | n-C$_3$H$_7$ | Cl | 3-OCH$_3$ | 4-C$_2$H$_5$SO$_2$ | H | H | H | H |
| | CH$_3$ | n-C$_3$H$_7$ | Cl | 3-OCH$_3$ | 4-C$_2$H$_5$SO$_2$ | CH$_3$ | H | H | H |
| | CH$_3$ | n-C$_4$H$_9$ | Cl | 3-OCH$_3$ | 4-C$_2$H$_5$SO$_2$ | H | H | H | H |
| | CH$_3$ | n-C$_4$H$_9$ | Cl | 3-OCH$_3$ | 4-C$_2$H$_5$SO$_2$ | CH$_3$ | H | H | H |
| | CH$_3$ | H | Cl | 3-OCH$_3$ | 4-C$_2$H$_5$SO$_2$ | H | H | H | H |
| | CH$_3$ | H | Cl | 3-OCH$_3$ | 4-C$_2$H$_5$SO$_2$ | CH$_3$ | H | H | H |
| | C$_2$H$_5$ | H | Cl | 3-OCH$_3$ | 4-C$_2$H$_5$SO$_2$ | H | H | H | H |
| | C$_2$H$_5$ | H | Cl | 3-OCH$_3$ | 4-C$_2$H$_5$SO$_2$ | CH$_3$ | H | H | H |
| | n-C$_4$H$_9$ | H | Cl | 3-OCH$_3$ | 4-C$_2$H$_5$SO$_2$ | H | H | H | H |
| | n-C$_4$H$_9$ | H | Cl | 3-OCH$_3$ | 4-C$_2$H$_5$SO$_2$ | CH$_3$ | H | H | H |
| | i-C$_3$H$_7$ | H | Cl | 3-OCH$_3$ | 4-C$_2$H$_5$SO$_2$ | H | H | H | H |
| | i-C$_3$H$_7$ | H | Cl | 3-OCH$_3$ | 4-C$_2$H$_5$SO$_2$ | CH$_3$ | H | H | H |
| | —C$_5$H$_{10}$— | | Cl | 3-OCH$_3$ | 4-C$_2$H$_5$SO$_2$ | H | H | H | H |
| | —C$_5$H$_{10}$— | | Cl | 3-OCH$_3$ | 4-C$_2$H$_5$SO$_2$ | CH$_3$ | H | H | H |
| | CH$_3$ | CH$_3$ | Cl | 3-CH$_3$ | 4-C$_2$H$_5$SO$_2$ | H | H | H | H |
| | CH$_3$ | CH$_3$ | Cl | 3-CH$_3$ | 4-C$_2$H$_5$SO$_2$ | CH$_3$ | H | H | H |
| | CH$_3$ | n-C$_3$H$_7$ | Cl | 3-CH$_3$ | 4-C$_2$H$_5$SO$_2$ | H | H | H | H |
| | CH$_3$ | n-C$_3$H$_7$ | Cl | 3-CH$_3$ | 4-C$_2$H$_5$SO$_2$ | CH$_3$ | H | H | H |
| | CH$_3$ | n-C$_4$H$_9$ | Cl | 3-CH$_3$ | 4-C$_2$H$_5$SO$_2$ | H | H | H | H |
| | CH$_3$ | n-C$_4$H$_9$ | Cl | 3-CH$_3$ | 4-C$_2$H$_5$SO$_2$ | CH$_3$ | H | H | H |
| | CH$_3$ | H | Cl | 3-CH$_3$ | 4-C$_2$H$_5$SO$_2$ | H | H | H | H |
| | CH$_3$ | H | Cl | 3-CH$_3$ | 4-C$_2$H$_5$SO$_2$ | CH$_3$ | H | H | H |
| | C$_2$H$_5$ | H | Cl | 3-CH$_3$ | 4-C$_2$H$_5$SO$_2$ | H | H | H | H |
| | C$_2$H$_5$ | H | Cl | 3-CH$_3$ | 4-C$_2$H$_5$SO$_2$ | CH$_3$ | H | H | H |
| | n-C$_4$H$_9$ | H | Cl | 3-CH$_3$ | 4-C$_2$H$_5$SO$_2$ | H | H | H | H |
| | n-C$_4$H$_9$ | H | Cl | 3-CH$_3$ | 4-C$_2$H$_5$SO$_2$ | CH$_3$ | H | H | H |
| | i-C$_3$H$_7$ | H | Cl | 3-CH$_3$ | 4-C$_2$H$_5$SO$_2$ | H | H | H | H |
| | i-C$_3$H$_7$ | H | Cl | 3-CH$_3$ | 4-C$_2$H$_5$SO$_2$ | CH$_3$ | H | H | H |
| | —C$_5$H$_{10}$— | | Cl | 3-CH$_3$ | 4-C$_2$H$_5$SO$_2$ | H | H | H | H |
| | —C$_5$H$_{10}$— | | Cl | 3-CH$_3$ | 4-C$_2$H$_5$SO$_2$ | CH$_3$ | H | H | H |

TABLE I-B-continued

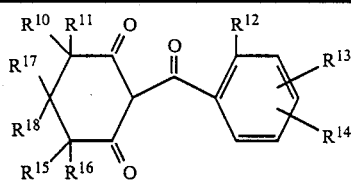

| Compound Number | R10 | R11 | R12 | R13 | R14 | R15 | R16 | R17 | R18 |
|---|---|---|---|---|---|---|---|---|---|
| | CH3 | CH3 | Cl | 3-OCH3 | 4-CH3SO2 | CH3 | H | H | H |
| | CH3 | n-C3H7 | Cl | 3-OCH3 | 4-CH3SO2 | H | H | H | H |
| | CH3 | n-C3H7 | Cl | 3-OCH3 | 4-CH3SO2 | CH3 | H | H | H |
| | CH3 | n-C4H9 | Cl | 3-OCH3 | 4-CH3SO2 | H | H | H | H |
| | CH3 | n-C4H9 | Cl | 3-OCH3 | 4-CH3SO2 | CH3 | H | H | H |
| | CH3 | H | Cl | 3-OCH3 | 4-CH3SO2 | H | H | H | H |
| | CH3 | H | Cl | 3-OCH3 | 4-CH3SO2 | CH3 | H | H | H |
| | C2H5 | H | Cl | 3-OCH3 | 4-CH3SO2 | H | H | H | H |
| | C2H5 | H | Cl | 3-OCH3 | 4-CH3SO2 | CH3 | H | H | H |
| | n-C4H9 | H | Cl | 3-OCH3 | 4-CH3SO2 | H | H | H | H |
| | n-C4H9 | H | Cl | 3-OCH3 | 4-CH3SO2 | CH3 | H | H | H |
| | i-C3H7 | H | Cl | 3-OCH3 | 4-CH3SO2 | H | H | H | H |
| | i-C3H7 | H | Cl | 3-OCH3 | 4-CH3SO2 | CH3 | H | H | H |
| | —C5H10— | | Cl | 3-OCH3 | 4-CH3SO2 | H | H | H | H |
| | —C5H10— | | Cl | 3-OCH3 | 4-CH3SO2 | CH3 | H | H | H |
| | CH3 | CH3 | Cl | 3-CH3 | 4-CH3SO2 | H | H | H | H |
| | CH3 | CH3 | Cl | 3-CH3 | 4-CH3SO2 | CH3 | H | H | H |
| | CH3 | n-C3H7 | Cl | 3-CH3 | 4-CH3SO2 | H | H | H | H |
| | CH3 | n-C3H7 | Cl | 3-CH3 | 4-CH3SO2 | CH3 | H | H | H |
| | CH3 | n-C4H9 | Cl | 3-CH3 | 4-CH3SO2 | H | H | H | H |
| | CH3 | n-C4H9 | Cl | 3-CH3 | 4-CH3SO2 | CH3 | H | H | H |
| | CH3 | H | Cl | 3-CH3 | 4-CH3SO2 | H | H | H | H |
| | CH3 | H | Cl | 3-CH3 | 4-CH3SO2 | CH3 | H | H | H |
| | C2H5 | H | Cl | 3-CH3 | 4-CH3SO2 | H | H | H | H |
| | C2H5 | H | Cl | 3-CH3 | 4-CH3SO2 | CH3 | H | H | H |
| | n-C4H9 | H | Cl | 3-CH3 | 4-CH3SO2 | H | H | H | H |
| | n-C4H9 | H | Cl | 3-CH3 | 4-CH3SO2 | CH3 | H | H | H |
| | i-C3H7 | H | Cl | 3-CH3 | 4-CH3SO2 | H | H | H | H |
| | i-C3H7 | H | Cl | 3-CH3 | 4-CH3SO2 | CH3 | H | H | H |
| | —C5H10— | | Cl | 3-CH3 | 4-CH3SO2 | H | H | H | H |
| | —C5H10— | | Cl | 3-CH3 | 4-CH3SO2 | CH3 | H | H | H |
| | CH3 | CH3 | Cl | 3-CH3 | 4-Cl | CH3 | H | H | H |
| | CH3 | n-C3H7 | Cl | 3-CH3 | 4-Cl | H | H | H | H |
| | CH3 | n-C3H7 | Cl | 3-CH3 | 4-Cl | CH3 | H | H | H |
| | CH3 | n-C4H9 | Cl | 3-CH3 | 4-Cl | H | H | H | H |
| | CH3 | n-C4H9 | Cl | 3-CH3 | 4-Cl | CH3 | H | H | H |
| | CH3 | H | Cl | 3-CH3 | 4-Cl | H | H | H | H |
| | CH3 | H | Cl | 3-CH3 | 4-Cl | CH3 | H | H | H |
| | C2H5 | H | Cl | 3-CH3 | 4-Cl | H | H | H | H |
| | C2H5 | H | Cl | 3-CH3 | 4-Cl | CH3 | H | H | H |
| | n-C4H9 | H | Cl | 3-CH3 | 4-Cl | H | H | H | H |
| | n-C4H9 | H | Cl | 3-CH3 | 4-Cl | CH3 | H | H | H |
| | i-C3H7 | H | Cl | 3-CH3 | 4-Cl | H | H | H | H |
| | i-C3H7 | H | Cl | 3-CH3 | 4-Cl | CH3 | H | H | H |
| | —C5H10— | | Cl | 3-CH3 | 4-Cl | H | H | H | H |
| | —C5H10— | | Cl | 3-CH3 | 4-Cl | CH3 | H | H | H |
| | CH3 | CH3 | Cl | 3-OCH3 | 4-Cl | CH3 | H | H | H |
| | CH3 | n-C3H7 | Cl | 3-OCH3 | 4-Cl | H | H | H | H |
| | CH3 | n-C3H7 | Cl | 3-OCH3 | 4-Cl | CH3 | H | H | H |
| | CH3 | n-C4H9 | Cl | 3-OCH3 | 4-Cl | H | H | H | H |
| | CH3 | n-C4H9 | Cl | 3-OCH3 | 4-Cl | CH3 | H | H | H |
| | CH3 | H | Cl | 3-OCH3 | 4-Cl | H | H | H | H |
| | CH3 | H | Cl | 3-OCH3 | 4-Cl | CH3 | H | H | H |
| | C2H5 | H | Cl | 3-OCH3 | 4-Cl | H | H | H | H |
| | C2H5 | H | Cl | 3-OCH3 | 4-Cl | CH3 | H | H | H |
| | n-C4H9 | H | Cl | 3-OCH3 | 4-Cl | H | H | H | H |
| | n-C4H9 | H | Cl | 3-OCH3 | 4-Cl | CH3 | H | H | H |
| | i-C3H7 | H | Cl | 3-OCH3 | 4-Cl | H | H | H | H |
| | i-C3H7 | H | Cl | 3-OCH3 | 4-Cl | CH3 | H | H | H |
| | —C5H10— | | Cl | 3-OCH3 | 4-Cl | H | H | H | H |
| | —C5H10— | | Cl | 3-OCH3 | 4-Cl | CH3 | H | H | H |
| | CH3 | CH3 | Cl | 3-n-C3H7O | 4-Br | H | H | H | H |
| | CH3 | CH3 | Cl | H | 4-C2H5SO2 | CH3 | H | H | H |
| | CH3 | CH3 | Cl | H | 4-NO2 | H | H | H | H |
| | CH3 | CH3 | Cl | 3-C2H5O | 4-CH3S | H | H | H | H |
| | CH3 | CH3 | Cl | H | 4-CN | H | H | H | H |

TABLE I-B-continued

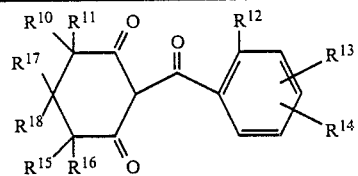

| Compound Number | R10 | R11 | R12 | R13 | R14 | R15 | R16 | R17 | R18 |
|---|---|---|---|---|---|---|---|---|---|
|  | CH$_3$ | CH$_3$ | Cl | 3-(CH$_3$)$_2$N | 4-Cl | H | H | H | H |

[a] Prepared in Example I-B.
* = 3-CH$_3$C(O)NH
** = 3-CH$_3$C(O)N(CH$_3$)

TABLE I-C

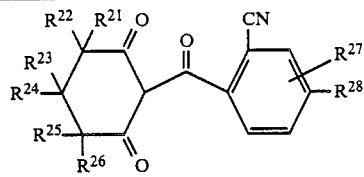

| Comp. No. | R21 | R22 | R23 | R24 | R25 | R26 | R27 | R28 | $n_D^{30}$ or m.p. |
|---|---|---|---|---|---|---|---|---|---|
| 1C[a] | CH$_3$ | CH$_3$ | H | H | H | H | H | H | oil |

TABLE I-C-continued

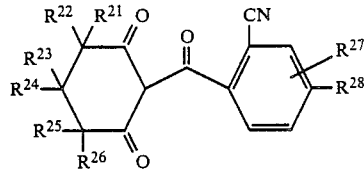

| Comp. No. | R21 | R22 | R23 | R24 | R25 | R26 | R27 | R28 | $n_D^{30}$ or m.p. |
|---|---|---|---|---|---|---|---|---|---|
| 2C | H | H | H | H | H | H | H | CN | 124–140° C. |

[a] Prepared in Example I-C.

TABLE I-D

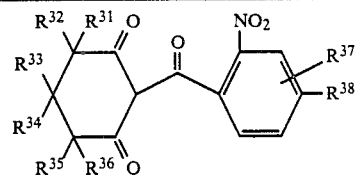

| Comp. No. | R31 | R32 | R33 | R34 | R35 | R36 | R37 | R38 | $n_D^{30}$ or m.p. |
|---|---|---|---|---|---|---|---|---|---|
| 1D | CH$_3$ | H | H | H | H | H | H | H | viscous oil |
| 2D | CH$_3$ | CH$_3$ | H | H | CH$_3$ | H | H | H | viscous oil |
| 3D[a] | H | H | H | H | H | H | H | H | 132–135 |
| 4D | CH$_3$ | CH$_3$ | H | H | H | H | H | H | viscous oil |
| 5D[b] | H | H | CH$_3$ | CH$_3$ | H | H | H | H | 130–133 |
| 6D | CH$_3$ | H | H | H | CH$_3$ | H | H | H | viscous oil |
| 7D | CH$_3$ | CH$_3$ | H | H | H | H | H | CF$_3$ | 52–61 |
| 8D | H | H | H | H | H | H | H | CF$_3$ | 88–94 |
| 9D | H | H | CH$_3$ | CH$_3$ | H | H | H | CF$_3$ | 89–97 |
| 10D | CH$_3$ | CH$_3$ | H | H | H | H | 3-CH$_3$ | H | 119–122 |
| 11D | CH$_3$ | CH$_3$ | H | H | H | H | 3-Cl | H | 72–79 |
| 12D | CH$_3$ | CH$_3$ | H | H | H | H | H | Cl | 118–121 |
| 13D | CH$_3$ | CH$_3$ | H | H | H | H | 5-Cl | H | 118–120 |
| 14D | CH$_3$ | CH$_3$ | H | H | H | H | 5-F | H | 130–133 |
| 15D | CH$_3$ | CH$_3$ | H | H | H | H | 3-CH$_3$O | H | 139–142 |
| 16D | CH$_3$ | CH$_3$ | CH$_3$ | H | H | H | H | CF$_3$ | viscous oil |
| 17D | CH$_3$ | CH$_3$ | H | H | H | H | H | NO$_2$ | viscous oil |
| 18D | CH$_3$ | CH$_3$ | H | H | H | H | H | Br | viscous oil |
| 19D | CH$_3$ | CH$_3$ | H | H | CH$_3$ | 5-CH$_3$ | H | viscous oil |
| 20D | CH$_3$ | CH$_3$ | H | H | H | 5-CH$_3$ | H | viscous oil |
| 21D | H | H | H | H | H | H | H | F | 123–128 |
| 22D | CH$_3$ | CH$_3$ | H | H | H | H | H | F | viscous oil |
| 23D | H | H | H | H | H | H | H | Cl | viscous oil |
| 24D | CH$_3$ | CH$_3$ | H | H | H | H | H | SO$_2$CH$_3$ | 130–133 |
| 25D | CH$_3$ | CH$_3$ | H | H | H | H | H | SO$_2$—n-C$_3$H$_7$ | viscous oil |
| 26D | H | H | H | H | H | H | H | SO$_2$CH$_3$ | 157–159 |
| 27D | H | H | H | H | H | H | H | SO$_2$—n-C$_3$H$_7$ | 120–123 |
| 28D | CH$_3$ | CH$_3$ | H | H | H | H | 5-F | H | 165–195 |
| 29D | CH$_3$ | CH$_3$ | H | H | H | H | H | SO$_2$—C$_2$H$_5$ | oil |
| 30D | CH$_3$ | CH$_3$ | H | H | CH$_3$ | H | H | SO$_2$—CH$_3$ | gum |
| 31D | CH$_3$ | n-C$_4$H$_9$ | H | H | H | H | H | H | viscous oil |
| 32D | H | H | i-C$_4$H$_9$ | H | H | H | H | H | viscous oil |
| 33D | H | H | H | H | H | H | H | SO$_2$—C$_2$H$_5$ | viscous oil |
| 34D | H | H | H | H | H | H | H | CN | viscous oil |

TABLE I-D-continued

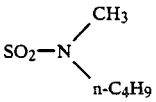

| Comp. No. | R³¹ | R³² | R³³ | R³⁴ | R³⁵ | R³⁶ | R³⁷ | R³⁸ | $n_D^{30}$ or m.p. |
|---|---|---|---|---|---|---|---|---|---|
| 35D | H | H | H | H | H | H | H | SO₂N(CH₃)₂ | 158–159 |
| 36D | CH₃ | CH₃ | H | H | H | H | H | SO₂N(CH₃)₂ | 120–130 |
| 37D | H | H | H | H | H | H | H | SO₂N(C₂H₅)₂ | 158–163 |
| 38D | CH₃ | CH₃ | H | H | H | H | H | SO₂N(C₂H₅)₂ | oil |
| 39D | CH₃ | CH₃ | H | H | H | H | H | SO₂—N(CH₃)(n-C₄H₉) | oil |
| 40D | H | H | CH₃ | CH₃ | H | H | H | SO₂—N(C₂H₅)₂ | oil |
| 41D | H | H | H | H | H | H | H | SC₂H₅ | oil |
| 42D | H | H | H | H | H | H | H | S(O)—n-C₃H₇ | oil |
| 43D | H | H | H | H | H | H | H | S—n-C₃H₇ | oil |
| 44D | CH₃ | CH₃ | H | H | CH₃ | H | H | S—n-C₃H₇ | oil |
| 45D | CH₃ | CH₃ | H | H | H | H | H | S—n-C₃H₇ | oil |
| 46D | CH₃ | CH₃ | H | H | CH₃ | H | H | S—C₂H₅ | oil |
| 47D | CH₃ | CH₃ | H | H | H | H | H | S—C₂H₅ | oil |
| 47D | CH₃ | CH₃ | H | H | H | H | H | S—C₂H₅ | oil |
| 48D | H | H | H | H | H | H | H | S—CH₃ | 94–97 |
| 49D | CH₃ | CH₃ | H | H | CH₃ | H | H | CF₃ | oil |
| 50D | CH₃ | CH₃ | H | H | H | H | H | S—CH₃ | oil |
| 51D | (c) | H | i-C₃H₇ | H | H | H | H | H | 145–148 |
| 52D | CH₃ | CH₃ | H | H | H | H | 5-CH₃O | Br | oil |
| 53D | H | H | CH₃ | CH₃ | H | H | H | Cl | oil |
| 54D | H | H | H | H | H | H | 3-CH₃O | Cl | oil |
| 55D | CH₃ | CH₃ | H | H | H | H | 3-CH₃O | Cl | oil |
| 56D | CH₃ | CH₃ | H | H | CH₃ | H | H | CH₃S | oil |
| 57D | H | H | H | H | H | H | H | SO₂N(H)(n-C₃H₇) | 120–125 |
| 58D | H | H | CH₃ | CH₃ | H | H | H | CN | 175–177 |
| 59D | CH₃ | CH₃ | H | H | H | H | H | CN | 151–153 |
| 60D | CH₃ | CH₃ | H | H | CH₃ | H | H | CN | oil |
| 61D | (c) | H | H | H | H | H | H | H | oil |
| 62D | (d) | H | H | H | H | H | H | H | oil |
| 63D | H | H | CH₃ | H | H | H | H | Cl | 110–115 |
| 64D | H | H | CH₃ | H | H | H | H | SO₂—n-C₃H₇ | oil |
| 65D | (d) | CH₃ | H | H | H | H | H | Cl | oil |
| 66D | H | H | H | H | H | H | H | SO₂CHCl₂ | oil |
| 67D | CH₃ | CH₃ | H | H | H | H | H | SO₂CHCl₂ | oil |
| 68D | H | H | H | H | H | H | (c) | Br | oil |
| 69D | H | H | H | H | H | H | H | SO₂CH₂Cl | oil |
| 70D | CH₃ | CH₃ | H | H | H | H | H | SO₂CH₂Cl | wax |
| 71D | (d) | CH₃ | H | H | H | H | H | H | oil |
| 72D | H | H | H | H | H | H | C₂H₅O | Cl | oil |
| 73D | CH₃ | CH₃ | H | H | CH₃ | H | CH₃O | CF₃ | oil |

(a) Prepared in Example 1-D,D'.
(b) Prepared in Example 2-D,D'.
(c) = C₂H₅OC(O)—
(d) = i-C₃H₇OC(O)—

TABLE I-E

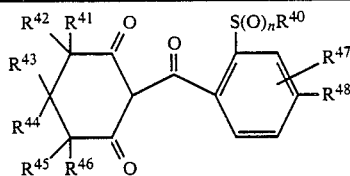

| Comp. No. | n | R⁴⁰ | R⁴¹ | R⁴² | R⁴³ | R⁴⁴ | R⁴⁵ | R⁴⁶ | R⁴⁷ | R⁴⁸ | m.p. |
|---|---|---|---|---|---|---|---|---|---|---|---|
| 1E | 0 | CH₃ | H | H | H | H | H | H | H | H | 79–81° C. |
| 2E | 0 | CH₃ | CH₃ | CH₃ | H | H | H | H | H | H | oil |
| 3E[a] | 0 | CH₃ | CH₃ | CH₃ | H | H | CH₃ | H | H | H | oil |
| 4E[b] | 2 | CH₃ | CH₃ | CH₃ | H | H | CH₃ | H | H | H | oil |
| 5E | 0 | C₂H₅ | CH₃ | CH₃ | H | H | H | H | H | H | oil |
| 6E | 2 | C₂H₅ | CH₃ | CH₃ | H | H | H | H | H | H | oil |
| 7E | 0 | CH₃ | H | H | H | H | H | H | 3-Cl | Cl | 59–64° C. |
| 8E | 2 | CH₃ | H | H | H | H | H | H | 3-Cl | Cl | 116–119° C. |
| 9E | 0 | CH₃ | H | H | H | H | H | H | H | CF₃ | 102–106° C. |
| 10E | 2 | CH₃ | H | H | H | H | H | H | H | CF₃ | oil |
| 11E | 0 | CH₃ | CH₃ | CH₃ | H | H | H | H | H | CF₃ | 49–53° C. |
| 12E | 2 | CH₃ | CH₃ | CH₃ | H | H | H | H | H | CF₃ | oil |
| 13E[c] | 1 | CH₃ | CH₃ | CH₃ | H | H | H | H | H | CF₃ | oil |
| 14E | 0 | CH₃ | H | H | H | H | H | H | 3-Cl | —SCH₃ | 105–107° C. |
| 15E | 1 | CH₃ | H | H | H | H | H | H | 3-Cl | —S(O)CH₃ | oil |
| 16E | 0 | CH₃ | H | H | H | H | H | H | H | —SO₂n-C₃H₇ | oil |
| 17E | 0 | CH₃ | H | H | H | H | H | H | H | —SCH₃ | 101–103° C. |
| 18E | 2 | CH₃ | H | H | H | H | H | H | H | —SO₂n-C₃H₇ | oil |
| 19E | 2 | CH₃ | H | H | H | H | H | H | H | —SO₂CH₃ | 194–196° C. |
| 20E | 0 | CH₃ | H | H | H | H | H | H | 3-CH₃ | H | 40–42° C. |
| 21E | 2 | CH₃ | H | H | H | H | H | H | 3-CH₃ | H | 80–86° C. |

[a]Prepared in Example 1-E,E'.
[b]Prepared in Example 2-E,E'.
[c]Prepared in Example 3-E,E'.

TABLE I-F

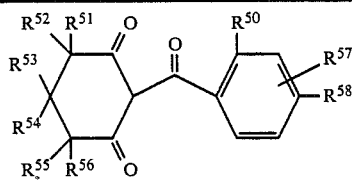

| Comp. No. | R⁵⁰ | R⁵¹ | R⁵² | R⁵³ | R⁵⁴ | R⁵⁵ | R⁵⁶ | R⁵⁷ | R⁵⁸ | $n_D^{30}$ or m.p. |
|---|---|---|---|---|---|---|---|---|---|---|
| 1F | CH₃ | H | H | H | H | H | H | H | H | 35–42° C. |
| 2F | CH₃ | CH₃ | CH₃ | H | H | H | H | H | H | 47–53° C. |
| 3F | CH₃ | CH₃ | CH₃ | H | H | H | H | H | Br | oil |
| 4F | CH₃ | CH₃ | CH₃ | H | H | H | H | H | CN | oil |
| 5F | CH₃ | CH₃ | CH₃ | H | H | H | H | 3-NO₂ | H | oil |
| 6F | CH₃ | CH₃ | CH₃ | H | H | H | H | 5-Cl | H | oil |
| 7F | CH₃ | CH₃ | CH₃ | H | H | H | H | H | CH₃SO₂— | oil |
| 8F | CH₃ | CH₃ | CH₃ | H | H | CH₃ | H | H | CH₃SO₂— | oil |
| 9F | CH₃ | CH₃ | CH₃ | H | H | H | H | 3-Cl | H | oil |
| 10F | CH₃ | CH₃ | CH₃ | H | H | CH₃ | H | H | C₂H₅SO₂— | oil |
| 11F | CH₃ | CH₃ | CH₃ | H | H | H | H | H | C₂H₅SO₂— | oil |
| 12F | CH₃ | CH₃ | CH₃ | H | H | H | H | H | n-C₃H₇SO₂— | oil |
| 13F | CH₃ | H | H | H | H | H | H | H | CH₃SO₂— | oil |
| 14F | CH₃ | H | H | H | H | H | H | H | n-C₃H₇SO₂— | oil |
| 15F | CH₃ | CH₃ | CH₃ | H | H | H | H | H | CH₃S— | oil |
| 16F | C₂H₅ | CH₃ | CH₃ | H | H | H | H | H | Br | oil |
| 17F | CH₃ | H | H | H | H | H | H | H | CN | oil |
| 18F | CH₃ | CH₃ | CH₃ | H | H | H | H | H | F | oil |
| 19F | CH₃ | H | H | H | H | H | H | H | C₂H₅—SO₂— | oil |
| 20F | CH₃ | H | H | H | H | H | H | 3-Cl | H | 65–67° C. |
| 21F | CH₃ | H | H | H | H | H | H | 3-I | H | oil |
| 22F | CH₃ | H | H | H | H | H | H | 3-NO₂ | H | oil |
| 23F | CH₃ | H | H | H | H | H | H | 3-CN | H | 96–101° C. |
| 24F | CF₃ | CH₃ | CH₃ | H | H | H | H | H | H | oil |
| 25F | CF₃ | H | H | H | H | H | H | H | H | oil |
| 26F | CF₃ | CH₃ | CH₃ | H | H | H | H | H | Br | oil |
| 27F | CF₃ | H | H | H | H | H | H | H | Cl | 82–88° C. |
| 28F | CF₃ | CH₃ | CH₃ | H | H | H | H | H | Cl | oil |
| 29F | CF₃ | H | H | H | H | H | H | H | C₂H₅S— | oil |
| 30F | CF₃ | CH₃ | CH₃ | H | H | H | H | H | C₂H₅SO₂— | oil |
| 31F | CF₃ | H | H | H | H | H | H | H | CN | oil |

TABLE I-F-continued

| Comp. No. | R⁵⁰ | R⁵¹ | R⁵² | R⁵³ | R⁵⁴ | R⁵⁵ | R⁵⁶ | R⁵⁷ | R⁵⁸ | $n_D^{30}$ or m.p. |
|---|---|---|---|---|---|---|---|---|---|---|
| 32F | CF₃ | CH₃ | CH₃ | H | H | H | H | H | CN | oil |
| 33F[a] | CF₃ | CH₃ | CH₃ | H | H | CH₃ | H | H | Br | oil |
| 34F | CH₃ | H | H | H | H | H | H | H | CH₃ | |
| 35F | CH₃ | CH₃ | CH₃ | H | H | H | H | 3-Cl | C₂H₅SO₂ | 115–117° C. |
| 36F | CH₃ | H | H | H | H | H | H | 3-Cl | C₂H₅SO₂ | oil |
| 37F | CH₃ | b | b | H | H | H | H | 3-CF₃ | H | oil |
| 38F | CH₃ | c | H | i-C₃H₇ | H | H | H | 3-NO₂ | H | 88–108° C. |
| 39F | CF₃ | CH₃ | CH₃ | H | H | CH₃ | H | H | CH₃S | oil |
| 40F | CF₃ | CH₃ | CH₃ | H | H | H | H | H | CH₃S | oil |
| 41F | CF₃ | CH₃ | CH₃ | H | H | CH₃ | H | H | CH₃SO₂— | oil |
| 42F | CH₃ | CH₃ | CH₃ | H | H | H | H | H | CF₃ | oil |
| 43F | CH₃ | H | H | H | H | H | H | H | CF₃ | 114–120° C. |
| 44F | CH₃ | H | H | H | H | H | H | 3-Cl | Cl | oil |
| 45F | CH₃ | CH₃ | CH₃ | H | H | H | H | 3-Cl | Cl | oil |
| 46F | CH₃ | CH₃ | CH₃ | H | H | H | H | 3-CF₃ | H | oil |
| 47F | CF₃ | H | H | H | H | H | H | H | CH₃S | oil |
| 48F | CF₃ | CH₃ | CH₃ | H | H | CH₃ | H | H | CF₃ | oil |
| 49F | CF₃ | H | H | H | H | H | H | H | CF₃ | oil |
| 50F | CF₃ | CH₃ | CH₃ | H | H | H | H | H | CF₃ | oil |
| 51F | CH₃ | H | H | CH₃ | H | H | H | H | CH₃SO₂ | oil |
| 52F | CF₃ | CH₃ | CH₃ | H | H | CH₃ | H | H | C₂H₅SO₂ | oil |
| 53F | CH₃ | H | H | H | H | H | H | H | Br | 94–98° C. |
| 54F | CH₃ | H | H | H | H | H | H | d | H | oil |

[a] Prepared in Example 1-F,F'.
[b] —(CH₂)₅
[c] C₂H₅OC(O)—
[d] 3-N(CH₃)COCH₃

TABLE I-G

| Comp. No. | R⁶⁰ | R⁶¹ | R⁶² | R⁶³ | R⁶⁴ | R⁶⁵ | R⁶⁶ | m.p. °C. |
|---|---|---|---|---|---|---|---|---|
| 1G | NO₂ | CH₃ | CH₃ | CH₃ | CH₃ | H | H | 112–117 |
| 2G[a] | NO₂ | CH₃ | CH₃ | CH₃ | CH₃ | H | 4-Cl | 76–82 |
| 3G | Cl | CH₃ | CH₃ | CH₃ | CH₃ | H | 4-SO₂CH₃ | 176–179° |
| 4G | CH₃ | CH₃ | CH₃ | CH₃ | CH₃ | H | 4-SO₂C₂H₅ | gum |
| 5G | CF₃ | CH₃ | CH₃ | CH₃ | CH₃ | H | 4-CF₃ | viscous oil |
| 6G | NO₂ | CH₃ | CH₃ | CH₃ | CH₃ | H | 4-SO₂CH₂Cl | oil |
| 7G | Cl | CH₃ | CH₃ | CH₃ | CH₃ | H | 4-F | gum |
| 8G | Cl | CH₃ | CH₃ | CH₃ | CH₃ | 3-OC₂H₅ | 4-SO₂C₂H₅ | gum |
| 9G | NO₂ | CH₃ | CH₃ | CH₃ | CH₃ | H | 4-SO₂CH₃ | gum |
| 10G | Cl | CH₃ | CH₃ | CH₃ | CH₃ | H | 4-SCH₃ | gum |
| 11G | CH₃ | CH₃ | CH₃ | CH₃ | CH₃ | 3-NO₂ | H | gum |
| 12G | I | CH₃ | CH₃ | CH₃ | CH₃ | H | H | gum |
| 13G | OCH₃ | CH₃ | CH₃ | CH₃ | CH₃ | H | 4-Cl | gum |
| 14G | Cl | CH₃ | CH₃ | CH₃ | CH₃ | 3-OCH₃ | 4-Br | gum |
| 15G | NO₂ | CH₃ | CH₃ | CH₃ | CH₃ | H | 4-SO₂nC₃H₇ | gum |
| 16G | NO₂ | CH₃ | CH₃ | CH₃ | CH₃ | H | 4-SO₂N(CH₃)₂ | gum |
| 17G | NO₂ | CH₃ | CH₃ | CH₃ | CH₃ | H | 4-CN | 148–150° |
| 18G | SO₂CH₃ | CH₃ | CH₃ | CH₃ | CH₃ | H | H | gum |
| 19G | NO₂ | CH₃ | CH₃ | CH₃ | CH₃ | H | 4-CF₃ | gum |
| 20G | H | CH₃ | CH₃ | CH₃ | CH₃ | H | 4-Cl | gum |
| 21G | H | CH₃ | CH₃ | CH₃ | CH₃ | H | 4-SCF₃ | gum |
| 22G | H | CH₃ | CH₃ | CH₃ | CH₃ | H | 4-OCF₃ | gum |
| 23G | Cl | CH₃ | CH₃ | CH₃ | CH₃ | 3-Cl | 4-SO₂C₂H₅ | gum |
| 24G | H | CH₃ | CH₃ | CH₃ | CH₃ | H | 4-C(O)CH₃ | gum |
| 25G | H | CH₃ | CH₃ | CH₃ | CH₃ | H | 4-SO₂—CH₃ | 129–131 |
| 26G | H | CH₃ | CH₃ | CH₃ | CH₃ | H | 4-SCH₃ | 89–92 |
| 27G | H | CH₃ | CH₃ | CH₃ | CH₃ | H | 4-CF₃ | 115–125 |

TABLE I-G-continued

| Comp. No. | R$^{60}$ | R$^{61}$ | R$^{62}$ | R$^{63}$ | R$^{64}$ | R$^{65}$ | R$^{66}$ | m.p. °C. |
|---|---|---|---|---|---|---|---|---|
| 28G | H | CH$_3$ | CH$_3$ | CH$_3$ | CH$_3$ | H | 4-CN | 87–95 |

$^a$prepared in Example 1-G,G'.

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence herbicide test

On the day preceding treatment, seeds of eight different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), redroot pigweed (PW) (*Amaranthus retroflexus*) or curly dock (CD) (*Rumex crispus*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Tables:

TABLE II-A

Pre-Emergence Herbicidal Activity
Application Rate - 4.48 kg/ha

| Cmpd. No. | FT | WG | WO | AMG | VL | MD | PW | CD | YNG |
|---|---|---|---|---|---|---|---|---|---|
| 1A | 100 | 90 | 20 | 40 | 65 | 50 | 35 | | 80 |
| 2A | 80 | 90 | 0 | 30 | 80 | 90 | 20 | | 90 |
| 3A | 0 | 0 | 0 | 40 | 40 | 40 | 0 | | 0 |
| 4A | 100 | 100 | 50 | 35 | 100 | 100 | 90 | | 95 |
| 5A | 100 | 95 | 65 | 35 | 90 | 85 | 50 | | 95 |
| 6A | 50 | 25 | 0 | 25 | 100 | 100 | 35 | | 80 |
| 7A | 80 | 90 | 10 | 60 | 100 | 100 | 100 | | 80 |
| 8A | 95 | 95 | 45 | 40 | 100 | 80 | 95 | | 95 |
| 9A | 95 | 100 | 55 | 30 | 100 | 90 | 100 | | 95 |
| 10A | 100 | 100 | 60 | 20 | 85 | 100 | 100 | | 95 |
| 11A | 85 | 100 | 30 | 40 | 100 | 100 | 100 | | 95 |
| 12A | 85 | 85 | 90 | 75 | 80 | 95 | 90 | | 90 |
| 13A | 85 | 75 | 10 | 10 | 85 | 65 | 95 | | 90 |
| 14A | 40 | 10 | 80 | 0 | 65 | 40 | 65 | | 100 |
| 15A | 40 | 60 | 20 | 30 | 100 | 30 | 75 | | 95 |
| 16A | 80 | 80 | 20 | 55 | 75 | 90 | 40 | | 95 |
| 17A | 20 | — | 10 | 25 | 100 | 95 | 85 | | 90 |
| 18A | 65 | — | 30 | 70 | 100 | 100 | 85 | | 90 |
| 19A | 45 | 60 | 0 | 30 | 40 | 0 | 20 | | 60 |
| 20A | 30 | 85 | 20 | 40 | 95 | 85 | 40 | | 45 |
| 21A | 80 | 100 | 0 | 80 | 100 | 100 | 95 | | 95 |
| 22A | 20 | 10 | 0 | 20 | 75 | 30 | 45 | | 10 |
| 23A | 45 | 95 | 10 | 0 | 100 | 85 | 100 | | 95 |
| 24A | — | 100 | 0 | 25 | 70 | 90 | — | | 100 |
| 25A | — | 100 | 25 | 80 | 100 | 100 | — | | 100 |
| 26A | 40 | 15 | 0 | 0 | 0 | 10 | | 0 | 30 |
| 27A | 40 | 80 | 10 | 20 | 60 | 50 | | 30 | 75 |
| 28A | 65 | 75 | 0 | 65 | 100 | 95 | | 75 | 55 |
| 29A | 100 | 95 | 55 | 10 | 80 | 75 | | 85 | 95 |
| 30A | 20 | 20 | 20 | 10 | 40 | 40 | | 50 | 20 |
| 31A | 75 | 95 | 20 | 20 | 100 | 95 | | 75 | 10 |
| 32A | 90 | 85 | 20 | 0 | 100 | 85 | | 75 | 30 |
| 33A | 80 | 70 | 0 | 40 | 20 | 40 | | 90 | 80 |

TABLE II-A-continued

Pre-Emergence Herbicidal Activity
Application Rate - 4.48 kg/ha

| | | | | | | | | |
|---|---|---|---|---|---|---|---|---|
| 34A | 60 | 40 | 0 | 20 | 95 | 100 | 100 | 60 |
| 35A | 0 | 10 | 0 | 0 | 10 | 20 | 20 | 10 |
| 36A | 0 | 0 | 0 | 20 | 100 | 100 | 100 | 0 |
| 37A | 40 | 0 | 0 | 20 | 100 | 60 | 90 | — |
| 38A | 10 | 40 | 0 | 20 | 90 | 80 | 20 | 20 |
| 39A | 80 | 10 | 0 | 0 | 0 | 0 | 0 | 90 |
| 40A | 60 | 0 | 0 | 0 | 0 | 0 | 0 | 90 |
| 41A | 100 | 100 | 85 | 40 | 95 | 100 | 100 | 100 |
| 42A | 60 | 100 | 25 | 0 | 0 | 0 | 0 | 25 |
| 43A | 100 | 100 | 45 | 40 | 80 | 90 | 90 | 100 |
| 44A | 90 | 100 | 0 | 60 | 100 | 100 | 100 | 95 |
| 45A | 100 | 100 | 0 | 60 | 100 | 100 | 100 | 100 |
| 46A | 20 | 60 | 0 | 100 | 100 | 100 | 100 | 20 |
| 47A | 60 | 70 | 20 | 100 | 100 | 100 | 100 | 60 |
| 48A | 60 | 0 | 0 | 0 | 0 | 0 | 0 | 40 |
| 49A | 100 | 100 | 50 | 10 | 60 | 20 | 90 | 100 |
| 50A | 100 | 100 | 80 | 10 | 60 | 60 | 90 | 100 |
| 51A | 100 | 100 | 90 | 100 | 100 | 100 | 85 | 100 |
| 52A | 100 | 100 | 60 | 10 | 100 | 100 | 60 | 100 |
| 53A | 0 | 20 | 0 | 0 | 20 | 20 | 0 | 10 |
| 54A | 10 | 45 | 10 | 0 | 0 | 0 | 0 | 40 |
| 55A | 90 | 100 | 60 | 100 | 100 | 100 | 90 | 100 |
| 56A | 40 | 70 | 40 | 40 | 40 | 60 | 70 | 50 |
| 57A | 100 | 100 | 90 | 100 | 100 | 100 | 85 | 100 |
| 58A | 90 | 95 | 0 | 20 | 20 | 40 | 40 | 100 |
| 59A | 95 | 100 | 85 | 75 | 100 | 100 | 90 | 98 |
| 60A | 95 | 100 | 50 | 50 | 100 | 100 | 90 | 98 |
| 61A | 100 | 100 | 75 | 100 | 100 | 100 | 95 | 95 |
| 62A | 100 | 100 | 95 | 75 | 100 | 100 | 100 | 80 |
| 63A | 100 | 100 | 40 | 65 | 100 | 100 | 100 | 95 |
| 64A | 100 | 100 | 98 | 100 | 100 | 100 | 100 | 90 |
| 65A | 100 | 100 | 80 | 100 | 100 | 100 | 100 | 90 |
| 66A | 100 | 100 | 75 | 100 | 100 | 100 | 100 | 98 |
| 73A | 100 | 100 | 60 | 80 | 100 | 100 | 75 | 90 |
| 74A | 100 | 100 | 70 | 80 | 100 | 100 | 80 | 100 |
| 75A | 70 | 100 | 0 | 50 | 100 | 100 | 100 | 80 |
| 76A | 40 | 90 | 25 | 10 | 100 | 100 | 100 | 10 |
| 77A | 100 | 100 | 90 | 100 | 100 | 100 | 85 | — |
| 78A | 100 | 100 | 80 | 100 | 100 | 100 | 90 | — |
| 79A | 50 | 100 | 50 | 50 | 95 | 100 | 100 | 60 |
| 80A | 0 | 0 | 0 | 0 | 0 | 0 | 0 | 0 |
| 81A | 100 | 100 | 50 | 15 | 100 | 100 | 90 | 100 |
| 84A | 100 | 100 | 85 | 0 | 0 | 100 | 20 | 100 |
| 88A | 60 | 95 | 35 | 95 | 100 | 100 | 95 | 80 |
| 89A | 75 | 100 | 40 | 100 | 100 | 100 | 95 | 60 |
| 90A | 100 | 100 | 90 | 100 | 100 | 100 | 100 | 85 |
| 105A | 80 | 95 | 25 | 0 | 95 | 50 | 70 | 50 |

| Cmpd. No. | FT | WG | WO | AMG | VL | MD | PW | CD | YNS |
|---|---|---|---|---|---|---|---|---|---|
| 117A | 95 | 100 | 0 | 25 | 100 | 100 | | 50 | 95 |
| 118A | 100 | 100 | 60 | 100 | 100 | 100 | | 100 | 85 |
| 121A | 95 | 100 | 50 | 75 | 100 | 95 | | 100 | 80 |
| 125A | 100 | 100 | 50 | 80 | 100 | 100 | | 100 | 85 |
| 126A | 70 | 100 | 80 | 80 | 100 | 100 | | 100 | 80 |
| 127A | 100 | 100 | 100 | 100 | 100 | 100 | | — | 80 |
| 128A | 100 | 100 | 100 | 100 | 100 | 100 | | — | 80 |
| 129A | 100 | 100 | 95 | 90 | 100 | 100 | | — | 80 |
| 131A | 70 | 85 | 0 | 20 | 95 | 98 | | 95 | 90 |
| 132A | 100 | 100 | 95 | 90 | 100 | 100 | | — | 80 |
| 133A | 100 | 100 | 100 | 100 | 100 | 100 | | — | 80 |
| 135A | 100 | 100 | 100 | 80 | 100 | 100 | | — | 80 |

TABLE II-B

Pre-Emergence Herbicidal Activity
Application Rate - 4.48 kg/ha

| Cmpd. No. | FT | WG | WO | AMG | VL | MD | CD | YNS |
|---|---|---|---|---|---|---|---|---|
| 1B | 0 | 85 | 10 | 75 | 100 | 80 | 80 | 75 |
| 2B | 90 | 100 | 65 | 100 | 100 | 100 | 100 | 100 |
| 4B | 100 | 100 | 80 | 60 | 100 | 80 | 90 | 100 |
| 5B | 80 | 100 | 20 | 40 | 100 | 100 | 80 | 100 |
| 6B | 40 | 100 | 0 | 40 | 100 | 100 | 80 | 100 |
| 7B | 100 | 100 | 100 | 80 | 100 | 100 | 90 | 100 |
| 8B | 100 | 100 | 60 | 45 | 60 | 60 | 80 | 100 |
| 9B | 60 | 100 | 40 | 20 | 60 | 60 | 60 | 100 |
| 10B | 100 | 100 | 40 | 5 | 80 | 60 | 80 | 100 |
| 11B | 100 | 100 | 90 | 10 | 20 | 20 | 40 | 100 |
| 12B | 0 | 20 | 0 | 0 | 10 | 20 | 10 | 0 |
| 13B | 100 | 100 | 90 | 40 | 100 | 100 | 100 | 100 |
| 15B | 90 | 90 | 50 | 20 | — | 100 | 100 | 80 |
| 16B | 100 | 100 | 95 | 100 | 100 | 100 | 90 | 100 |
| 17B | 100 | 100 | 100 | 100 | 100 | 100 | 100 | 97 |
| 18B | 100 | 100 | 85 | 100 | 100 | 100 | 90 | 95 |
| 19B | 100 | 100 | 95 | 100 | 100 | 100 | 100 | 95 |
| 20B | 100 | 100 | 85 | 100 | 100 | 100 | 100 | 90 |
| 21B | 100 | 100 | 100 | 100 | 100 | 100 | 100 | 95 |
| 22B | 100 | 100 | 80 | 100 | 100 | 100 | 100 | 90 |

TABLE II-B-continued

Pre-Emergence Herbicidal Activity
Application Rate - 4.48 kg/ha

| Cmpd. No. | FT | WG | WO | AMG | VL | MD | CD | YNS |
|---|---|---|---|---|---|---|---|---|
| 25B | 100 | 100 | 75 | 80 | 100 | 100 | 100 | 90 |
| 26B | 100 | 100 | 65 | 30 | 100 | 100 | 100 | 90 |
| 27B | 20 | 95 | 60 | 5 | 100 | 100 | 90 | 100 |
| 28B | 100 | 100 | 80 | 20 | 90 | 40 | 80 | 100 |
| 29B | 100 | 100 | 70 | 20 | 100 | 100 | 100 | 100 |
| 30B | 100 | 100 | 80 | 60 | 100 | 100 | 80 | 100 |
| 31B | 80 | 100 | 40 | 10 | 60 | 60 | 80 | 100 |
| 32B | 20 | 40 | 10 | 0 | — | 60 | 100 | 60 |
| 33B | 0 | 10 | 0 | 0 | 10 | 10 | 0 | 0 |
| 34B | 100 | 100 | 90 | 80 | 100 | 100 | 90 | 100 |
| 35B | 100 | 100 | 90 | 40 | 90 | 90 | 90 | 90 |
| 36B | 100 | 100 | 85 | 0 | 95 | 85 | 95 | 90 |
| 37B | 90 | 90 | 50 | 20 | — | 100 | 100 | 80 |
| 39B | 15 | 100 | 0 | 50 | 100 | 80 | 70 | 40 |
| 40B | 0 | 10 | 0 | 0 | 10 | 10 | 0 | 0 |
| 41B | 0 | 20 | 0 | 0 | 10 | 20 | 10 | 0 |
| 42B | 100 | 100 | 90 | 45 | 100 | 100 | 65 | 100 |
| 43B | 100 | 100 | 90 | 100 | 100 | 100 | 90 | 100 |
| 44B | 100 | 100 | 85 | 100 | 100 | 100 | 100 | 95 |
| 45B | 65 | 100 | 0 | 0 | 100 | 20 | 20 | 90 |
| 46B | 100 | 100 | 0 | 20 | 103 | 100 | 98 | 85 |
| 47B | 100 | 100 | 90 | 85 | 100 | 100 | 100 | 95 |
| 48B | 100 | 100 | 85 | 15 | 100 | 100 | 85 | 95 |
| 49B | 100 | 100 | 65 | 0 | 100 | 100 | 50 | 50 |
| 50B | 80 | 80 | 55 | 0 | 98 | 55 | 80 | 65 |
| 51B | 95 | 95 | 10 | 0 | 65 | 0 | 25 | 60 |
| 52B | 100 | 100 | 100 | 100 | 100 | 100 | 100 | 50 |
| 53B | 100 | 100 | 75 | 100 | 100 | 100 | 100 | 50 |
| 54B | 100 | 100 | 60 | 15 | 100 | 100 | 100 | 80 |
| 55B | 100 | 100 | 55 | 15 | 100 | 100 | 90 | 95 |
| 56B | 100 | 100 | 60 | 20 | 95 | 100 | 90 | 10 |
| 57B | 5 | 10 | 0 | 0 | 40 | 20 | 0 | 0 |
| 58B | 10 | 40 | 10 | 10 | 95 | 40 | 100 | 80 |
| 59B | 100 | 100 | 75 | 80 | 100 | 100 | 100 | 75 |
| 60B | 100 | 100 | 90 | 100 | 100 | 100 | 85 | — |
| 61B | 100 | 100 | 80 | 100 | 100 | 100 | 100 | — |
| 62B | 95 | 100 | 50 | 95 | 100 | 100 | 85 | — |
| 63B | 100 | 100 | 70 | 100 | 90 | 100 | 100 | — |
| 64B | 100 | 100 | 75 | 100 | 100 | 100 | 85 | — |
| 65B | 100 | 100 | 55 | 40 | 100 | 100 | 90 | 70 |
| 66B | 100 | 100 | 65 | 35 | 100 | 100 | 100 | 95 |
| 67B | 100 | 100 | 30 | 15 | 100 | 100 | 95 | 90 |
| 71B | 100 | 100 | 80 | 100 | 100 | 100 | 80 | — |
| 72B | 100 | 100 | 40 | 100 | 100 | 100 | 90 | 75 |
| 73B | 90 | 100 | 40 | 100 | 100 | 100 | 95 | 50 |
| 74B | 100 | 100 | 85 | 95 | 100 | 100 | 90 | 80 |
| 75B | 100 | 100 | 100 | 70 | 100 | 100 | 100 | 95 |
| 77B | 100 | 100 | 55 | 40 | 100 | 100 | 90 | 70 |
| 818 | 90 | 95 | 60 | 10 | 25 | 75 | 90 | 0 |
| 82B | 40 | 90 | 20 | 35 | 100 | — | 75 | 20 |
| 91B | 100 | 100 | 85 | 100 | 100 | 100 | 80 | 90 |
| 101B | 85 | 90 | 0 | 0 | 95 | 50 | 50 | 75 |

TABLE II-C

Pre-Emergence Herbicidal Activity
Application Rate - 4.48 kg/ha

| Cmpd. No. | FT | WG | WO | AMG | VL | MD | CD | YNS |
|---|---|---|---|---|---|---|---|---|
| 1C | 65 | 80 | 65 | 55 | 90 | 90 | 35 | 0 |

TABLE II-D

Pre-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1D | 100 | 100 | 85 | 30 | 100 | 100 | 90 | 90 |
| 2D | 100 | 100 | 100 | 50 | 100 | 100 | 95 | 95 |
| 3D | 100 | 100 | 85 | 25 | 100 | 100 | 100 | 95 |
| 4D | 100 | 100 | 100 | 20 | 100 | 85 | 95 | 90 |
| 5D | 100 | 100 | 45 | 25 | 100 | 100 | 90 | 90 |
| 6D | 100 | 100 | 95 | 40 | 100 | 100 | 85 | 90 |
| 9D | 100 | 100 | 90 | 90 | 100 | 100 | 80 | 90 |
| 10D | 100 | 90 | 20 | 10 | 100 | 70 | 100 | 90 |
| 11D | 90 | 100 | 50 | 230 | 100 | 100 | 90 | 90 |
| 12D | 100 | 100 | 95 | 80 | 100 | 100 | 90 | 90 |
| 13D | 40 | 75 | 0 | 10 | 80 | 100 | 100 | 90 |
| 14D | 50 | 0 | 0 | 0 | 100 | 80 | 70 | 90 |
| 15D | 65 | 95 | 20 | 15 | 100 | 80 | 90 | 85 |
| 17D | 100 | 100 | 60 | 30 | 100 | 100 | 90 | 35 |
| 18D | 100 | 100 | 100 | 100 | 100 | 100 | 100 | 95 |
| 19D | 100 | 100 | 0 | 50 | 100 | 100 | 100 | 95 |
| 20D | 75 | 100 | 0 | 25 | 100 | 90 | 65 | 90 |
| 21D | 100 | 100 | 100 | 80 | 100 | 100 | 90 | 95 |
| 22D | 100 | 100 | 100 | 80 | 100 | 100 | 95 | 95 |
| 23D | 100 | 100 | 98 | 95 | 100 | 100 | 100 | 95 |
| 25D | 100 | 100 | 80 | 100 | 100 | 100 | 80 | — |
| 26D | 100 | 100 | 75 | 100 | 100 | 100 | 80 | — |
| 27D | 90 | 100 | 50 | 100 | 100 | 100 | 100 | 90 |
| 28D | 75 | 50 | 50 | 0 | 100 | 100 | 90 | 65 |
| 30D | 100 | 100 | 85 | 100 | 100 | 100 | 95 | 90 |
| 31D | 85 | 75 | 0 | 25 | 100 | 25 | 0 | 35 |
| 32D | 83 | 85 | 35 | 20 | 95 | 100 | 75 | 50 |
| 36D | 100 | 100 | 50 | 100 | 100 | 100 | 100 | 75 |
| 37D | 20 | 75 | 0 | 20 | 100 | 95 | 100 | 75 |
| 38D | 85 | 95 | 40 | 60 | 100 | 100 | 75 | 85 |
| 39D | 85 | 95 | 45 | 75 | 100 | 95 | 70 | 90 |
| 51D | 60 | 60 | 35 | 0 | 25 | 0 | 0 | 30 |
| 52D | 75 | 75 | 0 | 50 | 90 | 75 | 40 | 0 |
| 65D | 100 | 100 | 80 | 100 | 100 | 100 | — | 80 |

A blank (—) indicates that the weed was not tested.

TABLE II-E

Pre-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1E | 0 | 0 | 0 | 0 | 0 | 0 | 0 | 20 |
| 2E | 25 | 30 | 30 | 0 | 70 | 0 | 40 | 30 |
| 3E | 25 | 20 | 0 | 0 | 0 | 0 | 0 | 0 |
| 4E | 100 | 100 | 90 | 60 | 100 | 100 | 100 | 90 |
| 5E | 50 | 60 | 40 | 50 | 50 | 60 | 90 | 50 |
| 6E | 100 | 95 | 50 | 40 | 40 | 60 | 99 | 70 |
| 16E | 80 | 100 | 50 | 60 | 100 | 90 | 90 | 90 |
| 20E | 100 | 100 | 30 | 15 | 100 | 100 | 90 | 85 |
| 21E | 100 | 100 | — | 30 | 100 | 95 | 100 | 80 |

A blank (—) indicates that the weed was not tested.

TABLE II-F

Pre-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1F | 40 | 20 | 0 | 0 | 0 | 0 | 0 | 100 |
| 2F | 60 | 70 | 0 | 0 | 0 | 0 | 90 | 100 |
| 3F | 100 | 100 | 50 | 50 | 100 | 100 | 85 | 90 |
| 4F | 100 | 100 | 90 | 30 | 100 | 85 | 95 | 95 |
| 5F | 100 | 100 | 80 | 10 | 100 | 100 | 100 | 95 |
| 6F | 20 | 35 | 25 | 15 | 90 | 85 | 40 | 85 |
| 7F | 100 | 100 | 90 | 100 | 100 | 100 | 100 | 95 |
| 8F | 100 | 100 | 90 | 100 | 100 | 100 | 100 | 95 |
| 9F | 100 | 100 | 0 | 0 | 100 | 80 | 100 | 90 |
| 10F | 100 | 100 | 100 | 100 | 100 | 100 | 100 | 95 |
| 11F | 100 | 100 | 70 | 100 | 100 | 100 | 97 | 95 |
| 12F | 100 | 100 | 60 | 100 | 100 | 100 | 100 | 95 |
| 13F | 100 | 100 | 60 | 100 | 100 | 100 | 100 | 95 |
| 14F | 80 | 100 | 50 | 80 | 100 | 100 | 90 | 90 |
| 15F | 100 | 100 | 80 | 100 | 100 | 100 | 100 | — |
| 16F | 50 | 75 | 0 | 25 | 100 | 100 | 95 | 60 |
| 17F | 100 | 100 | 40 | 100 | 100 | 100 | 100 | 85 |
| 18F | 100 | 100 | 0 | 20 | 100 | 100 | 80 | 70 |
| 20F | 70 | 75 | 0 | 25 | 100 | 95 | 100 | 60 |
| 21F | 50 | 60 | 0 | 0 | 100 | 80 | 80 | 60 |
| 22F | 100 | 95 | 35 | 25 | 100 | 100 | 90 | 50 |
| 23F | 95 | 100 | 40 | 20 | 100 | 100 | 90 | 50 |

TABLE II-F-continued

Pre-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 24F | 100 | 100 | 90 | 0 | 45 | 85 | 80 | 90 |
| 25F | 100 | 100 | 25 | 60 | 100 | 100 | 100 | 75 |
| 34F | 35 | 40 | 10 | 0 | 60 | 25 | 0 | 70 |
| 37F | 50 | 60 | 0 | 0 | 60 | 0 | 50 | 0 |
| 38F | 35 | 40 | 0 | 0 | 0 | 0 | 0 | 0 |
| 52F | 85 | 100 | 30 | 95 | 100 | 100 | — | 80 |
| 53F | 100 | 100 | 0 | 85 | 100 | 100 | — | 80 |
| 54F | 100 | 100 | 90 | 25 | 100 | 100 | — | 80 |

A blank (—) indicates that the weed was not tested.

TABLE II-G

Pre-Emergence Herbicidal Activity
Application Rate - 4.48 kg/ha

| Cmpd. No. | FT | WG | WO | AMG | VL | MD | YNG |
|---|---|---|---|---|---|---|---|
| 1G | 100 | 100 | 90 | 100 | 100 | 100 | 80 |
| 2G | 100 | 100 | 90 | 100 | 100 | 100 | 80 |
| 3G | 100 | 100 | 90 | 100 | 100 | 100 | 80 |
| 4G | 100 | 100 | 90 | 100 | 100 | 100 | 80 |
| 5G | 100 | 100 | 90 | 100 | 100 | 100 | 80 |
| 6G* | 100 | 100 | 100 | 100 | 100 | — | 20 |
| 7G | 100 | 100 | 80 | 100 | 100 | 100 | 80 |
| 8G | 85 | 100 | 80 | 100 | 100 | 100 | 80 |
| 9G | 100 | 100 | 80 | 100 | 100 | 100 | 80 |
| 10G | 100 | 100 | 80 | 100 | 100 | 100 | 80 |
| 11G | 100 | 100 | 80 | 100 | 100 | 100 | 80 |
| 12G | 100 | 100 | 80 | 90 | 100 | 100 | 0 |
| 13G | 100 | 100 | 70 | 100 | 100 | 100 | 0 |
| 14G | 100 | 100 | 75 | 100 | 100 | 100 | 90 |
| 15G | 100 | 100 | 80 | 100 | 100 | 100 | 90 |
| 16G | 100 | 100 | 90 | 100 | 100 | 100 | 80 |
| 17G | 100 | 100 | 80 | 100 | 100 | 100 | 80 |
| 18G | 100 | 100 | 90 | 85 | 100 | 100 | 80 |
| 19G | 100 | 100 | 100 | 100 | 100 | 100 | 80 |
| 20G | 70 | 95 | 10 | 100 | 100 | 100 | 0 |
| 21G | 100 | 100 | 100 | 100 | 100 | 100 | 80 |
| 22G | 100 | 100 | 90 | 100 | 100 | 100 | 80 |
| 23G | 100 | 100 | 100 | 100 | 100 | 100 | 80 |
| 24G | 0 | 80 | 0 | 25 | 80 | 70 | 0 |
| 25G | 100 | 100 | 80 | 100 | 100 | 100 | 80 |
| 26G | 100 | 100 | 100 | 80 | 100 | 100 | 80 |
| 27G | 100 | 100 | 100 | 100 | 100 | 100 | 80 |
| 28G | 100 | 100 | 90 | 100 | 100 | 100 | 80 |

A blank (—) indicates that the weed was not tested.
* = Tested at 0.56 kg/ha.

Post-Emergence Herbicide Test

This test is conducted in an identical manner to the testing procedure for the pre-emergence herbicide test, except the seeds of the eight different weed species are planted 10–12 days before treatment. Also, watering of the treated flats is confined to the soil surface and not to the foliage of the sprouted plants.

The results of the post-emergence herbicide test are reported in Table III.

TABLE III-A

Post-Emergence Herbicidal Activity
Application Rate - 4.48 kg/ha

| Cmpd. No. | FT | WG | WO | AMG | VL | MD | PW | CD | YNS |
|---|---|---|---|---|---|---|---|---|---|
| 1A | 60 | 70 | 20 | 40 | 60 | 60 | 35 | | 60 |
| 2A | 30 | 70 | 0 | 50 | 90 | 85 | 30 | | 80 |
| 3A | 0 | 30 | 0 | 70 | 100 | 90 | 55 | | 70 |
| 4A | 95 | 98 | 20 | 98 | 100 | 100 | 30 | | 95 |
| 5A | 80 | 80 | 75 | 50 | 60 | 80 | 0 | | 95 |
| 6A | 40 | 40 | 10 | 60 | 100 | 100 | 75 | | 65 |
| 7A | 60 | 75 | 40 | 60 | 100 | 75 | 100 | | 75 |
| 8A | 85 | 80 | 75 | 70 | 95 | 80 | 90 | | 90 |
| 9A | 85 | 80 | 75 | 70 | 95 | 80 | 90 | | 90 |
| 10A | 95 | 85 | 90 | 60 | 95 | 95 | 80 | | 95 |
| 11A | 50 | 80 | 35 | 55 | 100 | 100 | 95 | | 80 |
| 12A | 45 | 75 | 50 | 55 | 75 | 60 | 50 | | 80 |
| 13A | 30 | 60 | 20 | 60 | 80 | 50 | 60 | | 70 |
| 14A | 20 | 10 | 20 | 50 | 45 | 40 | 40 | | 0 |
| 15A | 65 | 95 | 0 | 65 | 95 | 30 | 100 | | 80 |
| 16A | 65 | 80 | 20 | 85 | 85 | 30 | 30 | | 80 |
| 17A | 75 | 80 | 30 | 70 | 100 | 100 | 85 | | 90 |
| 18A | 100 | 95 | 10 | 100 | 100 | 100 | 100 | | 90 |
| 19A | 60 | 80 | 40 | 70 | 100 | 75 | 80 | | 90 |
| 20A | 65 | 80 | 10 | 85 | 95 | 95 | 100 | | 70 |
| 21A | 30 | 55 | 0 | 80 | 100 | 80 | 65 | | 80 |
| 22A | 0 | 30 | 0 | 20 | 45 | 0 | 30 | | 20 |
| 23A | 85 | 90 | 40 | 85 | 100 | 95 | 100 | | 90 |
| 24A | 0 | 80 | 0 | 70 | 90 | 74 | — | | 100 |
| 25A | 100 | 100 | 75 | 90 | 100 | 100 | — | | 100 |
| 26A | 45 | 30 | 0 | 40 | 70 | 65 | | 0 | 45 |
| 27A | 75 | 80 | 30 | 65 | 50 | 45 | | 85 | 85 |
| 28A | 75 | 60 | 60 | 75 | 100 | 70 | | 80 | 25 |
| 29A | 85 | 85 | 85 | 75 | 85 | 65 | | 65 | 85 |
| 30A | 75 | 50 | 20 | 10 | 0 | 0 | | 20 | 40 |
| Cmpd. No. | FT | WG | WO | AMG | VL | MD | PW | CD | YNG |
| 31A | 60 | 60 | 20 | 40 | 40 | 70 | | 100 | 40 |
| 32A | 60 | 25 | 20 | 40 | 90 | 65 | | 20 | 40 |
| 33A | 10 | 0 | 0 | 10 | 10 | 10 | | 100 | 40 |
| 34A | 10 | 10 | 0 | 5 | 50 | 30 | | 80 | 0 |
| 35A | 0 | 0 | 0 | 10 | 60 | 30 | | 40 | 0 |
| 36A | 0 | 0 | 0 | 20 | 20 | 20 | | 0 | 0 |
| 37A | 0 | 0 | 0 | 30 | 40 | 20 | | 80 | 0 |
| 38A | 10 | 10 | 10 | 20 | 10 | 20 | | 20 | 10 |
| 39A | 40 | 40 | 20 | 0 | 0 | 0 | | 5 | 80 |

TABLE III-A-continued

Post-Emergence Herbicidal Activity
Application Rate - 4.48 kg/ha

| | | | | | | | | |
|---|---|---|---|---|---|---|---|---|
| 40A | 90 | 70 | 40 | 20 | 60 | 80 | 20 | 65 |
| 41A | 60 | 85 | 85 | 20 | 40 | 60 | 100 | 100 |
| 42A | 60 | 50 | 40 | 70 | 20 | 40 | 60 | 60 |
| 43A | 100 | 80 | 30 | 60 | 100 | 100 | 80 | 100 |
| 44A | 80 | 85 | 0 | 60 | 90 | 90 | 100 | 80 |
| 45A | 90 | 90 | 10 | 100 | 100 | 100 | 100 | 90 |
| 46A | 80 | 100 | 0 | 60 | 100 | 100 | 100 | 100 |
| 47A | 100 | 100 | 0 | 60 | 100 | 100 | 100 | 100 |
| 48A | 40 | 40 | 20 | 10 | 10 | 10 | 90 | 40 |
| 49A | 40 | 40 | 40 | 80 | 100 | 100 | 60 | 60 |
| 50A | 80 | 60 | 60 | 50 | 50 | 60 | 80 | 70 |
| 51A | 80 | 80 | 80 | 95 | 100 | 100 | 100 | 90 |
| 52A | 60 | 60 | 20 | 20 | 40 | 40 | 90 | 60 |
| 53A | 10 | 20 | 20 | 0 | 0 | 0 | 0 | 20 |
| 54A | 20 | 40 | 20 | 5 | 0 | 0 | 0 | 40 |
| 55A | 40 | 40 | 40 | 60 | 60 | 60 | 80 | 90 |
| 56A | 100 | 100 | 75 | 80 | 100 | 100 | 100 | 90 |
| 57A | 80 | 80 | 80 | 95 | 100 | 100 | 100 | 90 |
| 58A | 60 | 70 | 10 | 70 | 10 | 10 | 20 | 80 |
| 59A | 100 | 100 | 90 | 100 | — | 100 | 100 | 50 |
| 60A | 100 | 100 | 100 | 100 | — | 100 | 100 | 70 |
| 61A | 90 | 85 | 90 | 85 | — | 100 | 100 | 80 |
| 62A | 100 | 85 | 100 | 75 | 100 | 100 | 100 | 35 |
| 63A | 70 | 80 | 20 | 100 | 100 | 100 | 35 | 40 |
| 64A | 75 | 75 | 90 | 70 | 90 | 70 | 40 | 40 |
| 65A | 100 | 70 | 100 | 55 | 90 | 95 | 100 | 40 |
| 66A | 100 | 75 | 100 | 90 | 95 | 95 | 100 | 20 |
| 73A | 100 | 100 | 95 | 100 | 100 | 100 | 55 | 30 |
| 74A | 100 | 95 | 75 | 100 | 100 | 100 | 85 | 40 |
| 75A | 100 | 100 | 30 | 95 | 80 | 100 | 80 | 40 |
| 76A | 80 | 80 | 75 | 75 | 100 | 95 | 95 | 25 |
| 77A | 80 | 80 | 80 | 90 | 90 | 80 | 90 | 80 |
| 78A | 80 | 85 | 75 | 85 | 80 | 95 | 100 | 50 |
| 79A | 50 | 65 | 35 | 90 | 100 | 100 | 90 | — |
| 80A | 40 | 40 | 10 | 20 | 60 | 0 | 0 | 30 |
| 81A | 90 | 70 | 60 | 40 | 60 | 60 | 90 | 70 |
| 84A | 100 | 100 | 100 | 20 | 40 | 40 | 80 | 60 |
| 88A | 100 | 95 | 90 | 100 | 85 | 100 | 100 | 50 |
| 89A | 100 | 100 | 75 | 85 | 75 | 85 | 95 | 50 |
| 90A | 100 | 85 | 90 | 90 | 85 | 90 | 100 | 55 |
| 91A | 100 | 100 | 100 | 100 | 95 | 100 | 95 | 60 |
| 105A | 35 | 50 | — | 35 | 100 | 80 | 60 | 30 |
| 117A | 40 | 60 | 0 | 25 | 50 | 50 | 80 | — |
| 118A | 95 | 85 | 85 | 100 | 100 | 90 | 80 | 80 |
| 121A | 65 | 85 | 40 | 100 | 100 | 100 | 60 | 50 |
| 125A | 90 | 95 | 75 | 70 | 100 | 90 | 100 | 60 |
| 126A | 40 | 50 | 20 | 40 | 60 | 50 | 100 | 80 |
| 127A | 100 | 95 | 100 | 95 | 100 | 100 | | 80 |
| 128A | 85 | 95 | 80 | 60 | 100 | 95 | | 80 |
| 129A | 65 | 90 | 60 | 60 | 100 | 98 | | 70 |
| 130A | 100 | 95 | 95 | 95 | 100 | 100 | | 70 |
| 131A | 0 | 20 | 0 | 0 | 30 | 75 | 10 | 0 |
| 132A | 95 | 100 | 100 | 80 | 95 | 95 | | 50 |
| 133A | 80 | 95 | 90 | 60 | 35 | 85 | | 60 |
| 135A | 70 | 100 | 100 | 75 | 100 | 95 | | 70 |

TABLE III-B

Post-Emergence Herbicidal Activity
Application Rate - 4.48 kg/ha

| Cmpd. No. | FT | WG | WO | AMG | VL | MD | CD | YNS |
|---|---|---|---|---|---|---|---|---|
| 1B | 85 | 95 | 20 | 95 | 100 | 100 | 95 | 95 |
| 2B | 90 | 90 | 80 | 100 | 90 | 90 | — | 80 |
| 4B | 60 | 60 | 90 | 40 | 60 | 60 | 90 | 70 |
| 5B | 40 | 60 | 10 | 20 | 40 | 40 | 90 | 80 |
| 6B | 40 | 50 | 10 | 60 | 20 | 20 | 60 | 50 |
| 7B | 80 | 80 | 80 | 60 | 60 | 90 | 6 | 60 |
| 8B | 100 | 80 | 60 | 30 | 80 | 80 | 80 | 80 |
| 9B | 70 | 70 | 60 | 40 | 60 | 60 | 80 | 70 |
| 10B | 40 | 40 | 60 | 30 | 60 | 60 | 90 | 60 |
| 11B | 80 | 90 | 60 | 45 | 90 | 90 | 100 | 80 |
| 12B | 25 | 45 | 10 | 20 | 20 | 20 | 60 | 45 |
| 13B | 100 | 100 | 95 | 70 | 60 | 60 | 80 | 60 |
| 15B | 100 | 60 | 50 | 80 | 90 | 90 | 40 | 60 |
| 16B | 60 | 60 | 80 | 80 | 90 | 90 | 60 | 65 |
| 17B | 100 | 70 | 90 | 100 | — | 90 | 98 | 70 |
| 18B | 100 | 85 | 100 | 85 | — | 100 | 100 | 65 |
| 19B | 100 | 80 | 85 | 100 | 100 | 90 | 100 | 70 |
| 20B | 90 | 65 | 90 | 85 | 70 | 60 | 100 | 40 |
| 21B | 40 | 40 | 10 | 0 | 0 | 0 | 0 | 0 |
| 22B | 40 | 70 | 80 | 90 | 90 | 100 | 95 | 40 |
| 25B | 40 | 70 | 40 | 40 | 40 | 60 | 70 | 50 |
| 26B | 65 | 70 | 80 | 40 | 90 | 80 | 70 | 80 |
| 27B | 100 | 80 | 60 | 20 | 90 | 90 | 80 | 45 |
| 28B | 90 | 60 | 60 | 60 | 60 | 60 | 40 | 70 |
| 29B | 90 | 70 | 70 | 40 | 70 | 70 | 60 | 60 |
| 30B | 100 | 90 | 70 | 50 | 100 | 100 | 80 | 80 |
| 31B | 40 | 50 | 20 | 10 | 20 | 20 | 0 | 40 |
| 32B | 25 | 40 | 40 | 90 | 100 | 100 | 40 | 40 |
| 33B | 20 | 40 | 10 | 60 | 90 | 90 | 60 | 40 |
| 34B | 90 | 80 | 80 | 80 | 100 | 100 | 80 | 50 |
| 35B | 60 | 50 | 50 | 20 | 60 | 60 | 80 | 60 |
| 36B | 100 | 80 | 80 | 75 | — | 100 | 100 | 45 |

TABLE III-B-continued

Post-Emergence Herbicidal Activity
Application Rate - 4.48 kg/ha

| Cmpd. No. | FT | WG | WO | AMG | VL | MD | CD | YNS |
|---|---|---|---|---|---|---|---|---|
| 37B | 100 | 60 | 50 | 80 | 90 | 90 | 40 | 60 |
| 39B | 90 | 80 | 25 | 30 | 30 | 45 | 50 | 30 |
| 40B | 20 | 40 | 10 | 60 | 90 | 90 | 60 | 40 |
| 41B | 25 | 45 | 10 | 20 | 20 | 20 | 60 | 45 |
| 42B | 90 | 80 | 80 | 80 | 100 | 100 | 100 | 70 |
| 43B | 80 | 90 | 95 | 97 | 100 | 100 | 100 | 50 |
| 44B | 100 | 95 | 95 | 95 | 40 | 100 | 100 | 30 |
| 45B | 30 | 65 | 0 | 30 | 45 | 40 | 65 | 50 |
| 46B | 70 | 75 | 0 | 65 | 100 | 100 | 50 | 70 |
| 47B | 100 | 100 | 100 | 90 | 100 | 100 | 100 | 85 |
| 48B | 100 | 65 | 80 | 50 | 100 | 100 | 60 | 60 |
| 49B | 60 | 70 | 70 | 40 | 80 | 70 | 30 | 50 |
| 50B | 0 | 60 | 40 | 60 | 100 | 90 | 20 | 30 |
| 51B | 100 | 75 | 80 | 40 | 100 | 50 | 20 | 30 |
| 52B | 90 | 100 | 100 | 100 | 100 | 100 | 100 | 40 |
| 53B | 60 | 70 | 70 | 70 | 90 | 65 | 40 | 60 |
| 54B | 100 | 100 | 85 | 100 | 100 | 100 | 100 | 60 |
| 55B | 95 | 85 | 90 | 100 | 100 | 100 | 90 | 45 |
| 56B | 85 | 100 | 0 | 10 | 15 | 95 | 40 | 50 |
| 57B | 85 | 70 | 65 | 0 | 0 | 0 | 0 | 35 |
| 58B | 20 | 40 | 10 | 15 | 70 | 40 | 35 | 40 |
| 59B | 100 | 95 | 100 | 95 | 100 | 95 | 100 | 40 |
| 60B | 65 | 75 | 75 | 80 | 90 | 85 | 80 | 60 |
| 61B | 80 | 80 | 70 | 95 | 80 | 85 | 80 | 50 |
| 62B | 100 | 80 | 25 | 80 | 75 | 80 | 85 | 35 |
| 63B | 100 | 100 | 40 | 95 | 95 | 100 | 95 | 50 |
| 64B | 75 | 70 | 50 | 90 | 90 | 100 | 90 | 50 |
| 65B | 100 | 80 | 80 | 60 | 85 | 60 | 0 | — |
| 66B | 98 | 90 | 60 | 35 | — | 100 | 60 | 90 |
| 67B | 70 | 65 | 20 | 15 | 95 | 40 | 70 | 45 |
| 71B | 95 | 50 | 50 | 80 | 80 | 80 | 65 | 50 |
| 72B | 100 | 85 | 75 | 75 | 65 | 85 | 70 | 60 |
| 73B | 100 | 95 | 95 | 85 | 75 | 85 | 95 | 40 |
| 74B | 100 | 85 | 95 | 90 | 80 | 95 | 65 | 50 |
| 75B | 100 | 80 | 80 | 30 | 50 | 60 | 100 | 40 |
| 81B | 50 | 80 | 35 | 70 | 70 | 90 | 80 | 10 |
| 82B | 25 | 60 | 50 | 35 | 50 | 90 | 50 | 25 |
| 91B | 80 | 60 | 40 | 60 | 75 | 90 | 60 | 75 |
| 101B | 10 | 35 | — | 30 | 75 | 70 | 40 | 50 |

(—) = Specie did not germinate for some reason.

TABLE III-C

Post-Emergence Herbicidal Activity
Application Rate - 4.48 kg/ha

| Cmpd. No. | FT | WG | WO | AMG | VL | MD | CD | YNS |
|---|---|---|---|---|---|---|---|---|
| 1C | 98 | 95 | 70 | 60 | 100 | 55 | 100 | 90 |

TABLE III-D

Post-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1D | 95 | 75 | 85 | 70 | 100 | 90 | 85 | 40 |
| 2D | 45 | 70 | 95 | 75 | 100 | 90 | 100 | 65 |
| 3D | 100 | 80 | 100 | 90 | — | 100 | 100 | 80 |
| 4D | 100 | 80 | 100 | 100 | — | 100 | 85 | 75 |
| 5D | 90 | 70 | 45 | 60 | 95 | 70 | 60 | 80 |
| 6D | 95 | 75 | 80 | 70 | 100 | 90 | 90 | 65 |
| 9D | 100 | 90 | 90 | 100 | 100 | 100 | 95 | 85 |
| 10D | 45 | 75 | 10 | 15 | 100 | 100 | 20 | 75 |
| 11D | 100 | 70 | 60 | 75 | 100 | 100 | 100 | 45 |
| 12D | 100 | 75 | 100 | 100 | 100 | 100 | 90 | 90 |
| 13D | 30 | 55 | 0 | 30 | 60 | 60 | 15 | 60 |
| 14D | 20 | 65 | 0 | 40 | 70 | 60 | 40 | 25 |
| 15D | 20 | 75 | 30 | 20 | 100 | 70 | 60 | 40 |
| 17D | 85 | 80 | 50 | 65 | 95 | 95 | 100 | 60 |
| 18D | 100 | 95 | 100 | 100 | 100 | 100 | 100 | 75 |
| 19D | 20 | 95 | 30 | 100 | 100 | 35 | 30 | 70 |
| 20D | 30 | 80 | 15 | 100 | 100 | 45 | 20 | 70 |
| 21D | 100 | 80 | 100 | 55 | 100 | 90 | 100 | 80 |
| 22D | 100 | 80 | 100 | 60 | 100 | 95 | 95 | 95 |
| 23D | 100 | 90 | 90 | 100 | 100 | 100 | 85 | 70 |
| 25D | 70 | 75 | 50 | 85 | 90 | 85 | 60 | 75 |
| 26D | 100 | 85 | 85 | 95 | 95 | 95 | 90 | 60 |
| 27D | 90 | 90 | 60 | 100 | 100 | 100 | 100 | — |
| 28D | 15 | 45 | 20 | 50 | 75 | 80 | 15 | 30 |
| 30D | 100 | 100 | 80 | 85 | 85 | 85 | 100 | — |
| 31D | 80 | 90 | 100 | 100 | 100 | 100 | 100 | 60 |
| 32D | 75 | 85 | 85 | 75 | 75 | 90 | 95 | 50 |
| 36D | 35 | 50 | 35 | 70 | 50 | 50 | 35 | 60 |
| 37D | 60 | 75 | 15 | 70 | 70 | 90 | 90 | 40 |
| 38D | 95 | 90 | 65 | 70 | 90 | 90 | 100 | 50 |
| 39D | 95 | 85 | 30 | 50 | 70 | 80 | 100 | 50 |
| 51D | 60 | 75 | 60 | 35 | 30 | 60 | 40 | 60 |
| 52D | 60 | 75 | 25 | 100 | 100 | 100 | 100 | 75 |
| 65D | 70 | 50 | 70 | 90 | 80 | 85 | — | 80 |

A blank (—) indicates the weed was not tested.

TABLE III-E

Post-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1E | 20 | 20 | 10 | 20 | 40 | 40 | 20 | 40 |
| 2E | 0 | 60 | 60 | 50 | 70 | 30 | 0 | 15 |
| 3E | 20 | 20 | 0 | 10 | 0 | 20 | 0 | 20 |
| 4E | 85 | 90 | 100 | 45 | 75 | 30 | 80 | 65 |
| 5E | 55 | 50 | 60 | 50 | 75 | 85 | 65 | — |
| 6E | 70 | 70 | 50 | 60 | 80 | 70 | 90 | — |
| 16E | 95 | 95 | 40 | 100 | 100 | 100 | 100 | 90 |
| 20E | 95 | 75 | 35 | 40 | 95 | 75 | 35 | 80 |
| 21E | 80 | 70 | 30 | 45 | 80 | 90 | 50 | 70 |

A blank (—) indicates the weed was not tested.

TABLE III-F

Post-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1F | 60 | 40 | 20 | 30 | 40 | 40 | 50 | 60 |
| 2F | 50 | 40 | 10 | 20 | 20 | 20 | 40 | 60 |
| 3F | 100 | 100 | 85 | 100 | 100 | 100 | 100 | 75 |
| 4F | 100 | 100 | 95 | 85 | 100 | 95 | 100 | 60 |
| 5F | 95 | 95 | 100 | 65 | 90 | 25 | 70 | 45 |
| 6F | 40 | 30 | 0 | 20 | 90 | 25 | 20 | 70 |
| 7F | 100 | 100 | 100 | 100 | 100 | 100 | 100 | 90 |
| 8F | 100 | 95 | 100 | 100 | 100 | 100 | 100 | 70 |
| 9F | 65 | 65 | 0 | 20 | 80 | 65 | 90 | 80 |
| 10F | 100 | 100 | 100 | 100 | 100 | 100 | 100 | 70 |
| 11F | 85 | 90 | 90 | 85 | 90 | 80 | 30 | 60 |
| 12F | 100 | 90 | 65 | 80 | 100 | 100 | 100 | 50 |
| 13F | 100 | 95 | 100 | 100 | 100 | 100 | 90 | — |
| 14F | 100 | 100 | 100 | 100 | 100 | 100 | 100 | 50 |
| 15F | 25 | 35 | 15 | 30 | 80 | 25 | 20 | 0 |
| 16F | 100 | 85 | 70 | 75 | 90 | 90 | 50 | — |
| 17F | 100 | 100 | 100 | 100 | 100 | 100 | 100 | — |
| 18F | 90 | 85 | 85 | 85 | 90 | 95 | 70 | 40 |
| 20F | 40 | 60 | 10 | 60 | 100 | 100 | 100 | 50 |
| 21F | 35 | 60 | 10 | 60 | 100 | 100 | 80 | 60 |
| 22F | 95 | 95 | 35 | 100 | 100 | 100 | 90 | 50 |
| 23F | 100 | 100 | 40 | 100 | 100 | 100 | 90 | 50 |
| 24F | 100 | 75 | 100 | 60 | — | 100 | 100 | 60 |
| 25F | 95 | 95 | 90 | 95 | 100 | 100 | 95 | 35 |
| 34F | 50 | 40 | 0 | 35 | 50 | 70 | 30 | 50 |
| 37F | 20 | 60 | 0 | 30 | 30 | 50 | 50 | 50 |
| 38F | 25 | 50 | 0 | 25 | 25 | 50 | 20 | 20 |
| 52F | 0 | 60 | 50 | 50 | 10 | 50 | — | 20 |
| 53F | 0 | 50 | 0 | 50 | 50 | 50 | — | 30 |
| 54F | 90 | 75 | 60 | 50 | 50 | 50 | 80 | 80 |

A blank (—) indicates the weed was not tested.

TABLE III-G

Post-Emergence Herbicidal Activity
Application Rate - 4.48 kg/ha

| Cmpd. No. | FT | WG | WO | AMG | VL | MD | YNG |
|---|---|---|---|---|---|---|---|
| 1G | 100 | 95 | 90 | 90 | 100 | 100 | 80 |
| 2G | 100 | 100 | 100 | 100 | 100 | 100 | 80 |
| 3G | 100 | 100 | 95 | 100 | 100 | 100 | 90 |
| 4G | 100 | 100 | 100 | 100 | 100 | 100 | 90 |
| 5G | 100 | 100 | 100 | 100 | 100 | 100 | 100 |
| 6G* | 10 | 80 | 50 | 75 | 40 | — | 0 |
| 7G | 70 | 75 | 70 | 90 | 90 | 80 | 80 |
| 8G | 50 | 80 | 70 | 90 | 90 | 80 | 30 |
| 9G | 70 | 80 | 70 | 90 | 90 | 80 | 30 |
| 10G | 75 | 80 | 70 | 80 | 60 | 50 | 70 |
| 11G | 70 | 80 | 70 | 80 | 80 | 80 | 80 |
| 12G | 100 | 75 | 90 | 75 | 80 | 80 | 80 |
| 13G | 60 | 70 | 70 | 100 | 100 | 100 | 80 |
| 14G | 20 | 70 | 40 | 60 | 80 | 80 | 70 |
| 15G | 90 | 70 | 70 | 75 | 80 | 90 | 70 |
| 16G | 50 | 70 | 80 | 60 | 80 | 90 | 70 |
| 17G | 90 | 60 | 70 | 65 | 80 | 80 | 80 |
| 18G | 30 | 50 | 80 | 95 | 95 | 80 | 70 |
| 19G | 100 | 100 | 95 | 90 | 100 | 100 | 80 |
| 20G | 10 | 40 | 5 | 70 | 80 | 90 | 70 |
| 21G | 95 | 90 | 95 | 95 | 100 | 100 | 70 |
| 22G | 80 | 90 | 90 | 80 | 100 | 100 | 70 |
| 23G | 90 | 80 | 80 | 80 | 90 | 80 | 30 |
| 24G | 0 | 30 | 0 | 40 | 80 | 20 | 0 |
| 25G | 0 | 20 | 0 | 10 | 10 | 20 | 0 |
| 26G | 80 | 70 | 70 | 80 | 80 | 80 | 70 |
| 27G | 90 | 90 | 90 | 80 | 80 | 90 | 60 |
| 28G | 70 | 65 | 50 | 80 | 80 | 80 | 70 |

A blank (—) indicates the weed was not tested.
* = Tested at 0.56 kg/ha.

Pre-Emergence Multi-Weed Herbicide Test

Several compounds were evaluated at an application rate of 2 lb/acre (2.24 kg/ha) or 1 lb/acre (1.12 kg/ha) for pre-emergence activity against a larger number of weed species.

The process was generally similar to the pre-emergence herbicide test described above except that only 300 or 150 milligrams of test compound were weighed out and the application rate was 40 gallons per acre.

Redroot pigweed (PW) and curly dock (CD) were eliminated in this test and the following weed species were added:

| Grasses: | downy brome | Bromus tectorum | (DB) |
|---|---|---|---|
| | annual ryegrass | Lolium multiflorum | (ARG) |
| | rox-orange sorghum | Sorghum bicolor | (SHC) |
| | hemp sesbania | Sesbania exaltata | (SESB) |
| | nightshade | Solanum sp. | (SP) |
| | cocklebur | Xattiium sp. | (CB) |

The results of the 2.24 kg/ha test are shown in Table IV and the results of the 1.12 kg/ha test are shown in Table VI.

Post-Emergence Multi-Weed Herbicide Test

Several compounds were evaluated at an application rate of 2 lb/acre (2.24 kg/ha) or 1 lb/acre (1.12 kg/ha) for post-emergence activity against the larger number of weed species that are used in the pre-emergent multi-herbicide test.

The process was generally similar to the post-emergence herbicide test described above except that only 300 or 150 milligrams of test compound were weighed out and the application rate was 40 gallons per acre.

The results of the 2.24 kg/ha test are shown in Table V and the results for the 1.12 kg/ha test are shown in Table VII.

TABLE IV-A

Pre-Emergence Multi-weed Herbicide Test
Application Rate - 2.24 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 67A | 20 | 90 | 25 | 98 | 80 | 60 | 90 | 45 | 90 | 45 | 20 | 85 | 85 | 15 |
| 68A | 65 | 98 | 98 | 100 | 100 | 60 | 95 | 100 | 100 | 100 | 80 | 100 | 95 | 100 |
| 69A | 65 | 100 | 70 | 100 | 100 | 65 | 95 | 100 | 95 | 70 | 65 | 100 | 90 | — |
| 70A | 98 | 100 | 100 | 100 | 100 | 90 | 98 | 90 | 100 | 90 | 60 | 100 | 95 | 80 |
| 71A | 60 | 20 | 100 | 100 | 100 | 80 | 95 | 35 | 40 | 100 | 20 | 90 | 100 | 40 |
| 72A | 100 | 100 | 100 | 100 | 100 | 100 | 100 | 100 | 90 | 100 | 60 | 100 | 100 | 20 |
| 83A | 15 | 45 | 25 | 90 | 15 | 5 | 90 | 45 | 35 | 20 | 0 | 20 | 75 | — |
| 86A | 20 | 0 | 15 | 60 | 60 | 20 | 70 | 25 | 45 | 100 | 20 | 100 | 15 | 35 |
| 87A | 100 | 90 | 85 | 100 | 85 | 25 | 30 | 35 | 85 | 100 | 85 | 100 | 95 | 40 |

TABLE VI-A

Post-Emergence Multi-weed Herbicide Test
Application Rate - 2.24 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 86A | 60 | 100 | 50 | 90 | 50 | 60 | 90 | 70 | 100 | 100 | 20 | 100 | 20 | — |
| 87A | 95 | 100 | 30 | 100 | 80 | 70 | 80 | 95 | 100 | 100 | 100 | 100 | 70 | — |

TABLE V-A

Pre-Emergence Multi-weed Herbicide Test
Application Rate - 1.12 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 82A | 35 | 100 | 85 | 100 | 65 | 60 | 90 | 50 | 90 | 60 | 30 | 97 | 90 | 40 |
| 85A | 100 | 100 | 100 | 100 | 100 | 85 | 100 | 20 | 10 | 100 | 65 | 100 | 100 | 30 |
| 92A | 15 | 20 | 45 | 100 | 90 | 40 | 80 | 95 | 95 | 100 | 25 | 100 | 90 | 40 |
| 93A | 30 | 75 | 40 | 100 | 100 | 60 | 90 | 100 | 100 | 100 | 35 | 100 | 90 | 40 |
| 94A | 30 | 70 | 40 | 100 | 100 | 30 | 65 | 95 | 85 | 100 | 0 | 100 | 90 | 30 |
| 95A | 0 | 0 | 0 | 85 | 60 | 15 | 70 | 65 | 60 | 100 | 80 | 90 | 10 | 20 |

TABLE V-A-continued

Pre-Emergence Multi-weed Herbicide Test
Application Rate - 1.12 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 96A | 95 | 100 | 98 | 100 | 100 | 70 | 100 | 100 | 95 | 90 | 80 | 100 | 95 | — |
| 97A | 100 | 100 | 98 | 100 | 100 | 100 | 100 | 100 | 95 | 100 | 70 | 100 | 95 | 100 |
| 98A | 10 | 0 | 0 | 0 | 20 | 25 | 70 | 0 | 20 | 0 | 0 | 80 | 30 | — |
| 99A | 15 | 0 | 0 | 75 | 25 | 0 | 20 | 30 | 60 | 15 | 20 | 30 | 25 | 0 |
| 100A | 0 | 0 | 0 | 0 | 0 | 0 | 20 | 10 | 0 | 0 | 0 | 15 | 0 | — |
| 101A | 100 | 98 | 95 | 100 | 100 | 70 | 98 | 100 | 100 | 100 | 20 | 100 | 95 | — |
| 102A | 25 | 20 | 35 | 100 | 100 | 45 | 95 | 70 | 100 | 100 | 60 | 100 | 90 | — |
| 103A | 80 | 60 | 45 | 100 | 100 | 40 | 90 | 65 | 90 | 100 | 0 | 100 | 95 | 0 |
| 106A | 100 | 100 | 60 | 40 | 95 | 35 | 100 | 35 | 90 | 100 | 70 | 100 | 90 | — |
| 107A | 100 | 100 | 100 | 100 | 100 | 90 | 100 | 100 | 100 | 100 | 80 | 100 | 95 | 30 |
| 108A | 100 | 100 | 100 | 100 | 100 | 85 | 100 | 100 | 100 | 100 | 30 | 100 | 95 | 100 |
| 109A[a] | 65 | 20 | 85 | 100 | 98 | 60 | 90 | 30 | 50 | 100 | 50 | 100 | 90 | 100 |
| 110A | 0 | 60 | 30 | 100 | 65 | 25 | 65 | 25 | 30 | 100 | 0 | 100 | 60 | 0 |
| 111A | 100 | 100 | 100 | 100 | 100 | 75 | 98 | 100 | 100 | 100 | 90 | 100 | — | 70 |
| 112A | 100 | 100 | 90 | 100 | 100 | 95 | 100 | 100 | 100 | 100 | 100 | 100 | — | — |
| 113A | 65 | 95 | 40 | 100 | 100 | 30 | 90 | 70 | 100 | 100 | 0 | 100 | — | 30 |
| 114A | 70 | 100 | 25 | 100 | 100 | 40 | 100 | 100 | 100 | 100 | 30 | 100 | 95 | 80 |
| 115A | 100 | 100 | 100 | 100 | 100 | 100 | 100 | 100 | 100 | 100 | 45 | 100 | 85 | 100 |
| 116A | 25 | 15 | 20 | 100 | 65 | 35 | 65 | 45 | 50 | 100 | 0 | 100 | 95 | 10 |
| 119A | 100 | 100 | 100 | 100 | 100 | 100 | 100 | 100 | 100 | 100 | 95 | 100 | 95 | 90 |
| 120A | 100 | 100 | 100 | 100 | 100 | 95 | 100 | 100 | 100 | 100 | 100 | 100 | 90 | 100 |
| 122A | 80 | 80 | 45 | 100 | 60 | 65 | 70 | 100 | 100 | 100 | 100 | 100 | 90 | 100 |
| 123A | 0 | 100 | 50 | 100 | 85 | 0 | 60 | 100 | 90 | 100 | 80 | 100 | 100 | 20 |
| 124A | 25 | 50 | 65 | 90 | 65 | 0 | 40 | 75 | 80 | 100 | 40 | 90 | 80 | 60 |

[a] application rate was 0.56 kg/ha.

TABLE VII-A

Post-Emergence Multi-weed Herbicide Test
Application Rate - 1.12 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 82A | 60 | 40 | 10 | 98 | 35 | 10 | 30 | 70 | 100 | 100 | 100 | 90 | 45 | — |
| 85A | 60 | 60 | 35 | 100 | 45 | 60 | 85 | 50 | 100 | 100 | 100 | 100 | 60 | — |
| 92A | 70 | 55 | 20 | 80 | 80 | 45 | 100 | 95 | 90 | 80 | 20 | 95 | 70 | 90 |
| 93A | 90 | 90 | 70 | 95 | 95 | 75 | 90 | 98 | 95 | 85 | 35 | 100 | 60 | 90 |
| 94A | 100 | 85 | 45 | 90 | 100 | 90 | 100 | 100 | 90 | 90 | 30 | 100 | 60 | 85 |
| 95A | 20 | 60 | 0 | 80 | 70 | 0 | 45 | 60 | 75 | 90 | 0 | 65 | 20 | — |
| 96A | 95 | 100 | 90 | 95 | 100 | 80 | 95 | 100 | 100 | 100 | 70 | 100 | 70 | 90 |
| 97A | 100 | 100 | 95 | 100 | 100 | 100 | 100 | 100 | 100 | 100 | 90 | 100 | 70 | 100 |
| 98A | 20 | 0 | 0 | 45 | 10 | 50 | 30 | 20 | 65 | 100 | 0 | 75 | 35 | 80 |
| 99A | 25 | 75 | 15 | 80 | 65 | 10 | 25 | 85 | 100 | 100 | 80 | 100 | 10 | — |
| 100A | 10 | 35 | 0 | 70 | 50 | 5 | 20 | 30 | 70 | 40 | 0 | 100 | 10 | 100 |
| 101A | 30 | 60 | 25 | 100 | 60 | 60 | 80 | 100 | 100 | 100 | 30 | 100 | 70 | — |
| 103A | 90 | 100 | 25 | 100 | 100 | 80 | 100 | 100 | 100 | 100 | 15 | 100 | 40 | — |
| 104A | 98 | 98 | 25 | 98 | 100 | 15 | 100 | 100 | 100 | 100 | 60 | 100 | 95 | — |
| 106A | 75 | 90 | 30 | 90 | 70 | 25 | 100 | 100 | 100 | 100 | 80 | 100 | 75 | — |
| 107A | 100 | 100 | 80 | 90 | 85 | 100 | 100 | 100 | 100 | 100 | 60 | 100 | 40 | — |
| 108A | 100 | 100 | 65 | 90 | 60 | 95 | 100 | 100 | 100 | 100 | 90 | 100 | 90 | — |
| 109A[a] | 90 | 60 | 45 | 90 | 70 | 60 | 98 | 95 | 95 | 100 | 98 | 80 | 55 | — |
| 110A | 50 | 50 | 20 | 100 | 50 | 10 | 40 | 100 | 98 | 98 | 20 | 100 | 35 | 45 |
| 111A | 85 | 90 | 80 | 90 | 70 | 60 | 95 | 100 | 90 | 100 | 65 | 100 | 80 | 60 |
| 112A | 100 | 100 | 90 | 100 | 100 | 95 | 100 | 100 | 100 | 100 | 45 | 100 | 95 | 70 |
| 113A | 70 | 50 | 20 | 90 | 60 | 50 | 80 | 95 | 95 | 100 | 60 | 100 | — | 60 |
| 114A | 85 | 100 | 15 | 100 | 100 | 60 | 00 | 100 | 100 | 100 | 100 | 100 | 60 | — |
| 115A | 100 | 100 | 45 | 100 | 100 | 80 | 100 | 100 | 100 | 100 | 100 | 100 | 90 | — |
| 116A | 80 | 60 | 25 | 90 | 35 | 40 | 45 | 75 | 90 | 100 | 40 | 90 | 75 | 60 |
| 119A | 60 | 70 | 30 | 95 | 70 | 20 | 90 | 100 | 100 | 100 | 90 | 100 | 30 | 85 |
| 120A | 75 | 90 | 60 | 95 | 80 | 45 | 100 | 100 | 90 | 100 | 65 | 100 | 35 | 100 |
| 122A | 60 | 90 | 15 | 100 | 30 | 15 | 15 | 100 | 100 | 100 | 75 | 100 | 45 | 95 |
| 123A | 0 | 100 | 35 | 100 | 50 | 15 | 85 | 100 | 100 | 100 | 100 | 100 | 70 | 85 |
| 124A | 25 | 100 | 35 | 40 | 35 | 0 | 40 | 95 | 100 | 100 | 100 | 100 | 85 | 75 |

[a] Application rate was 0.56 kg/ha.

A dash mark (—) is used in Tables II–VII to indicate that no percent control number was available.

TABLE IV-B

Pre-Emergence Multi-Weed Herbicide Test
Application Rate - 2.24 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 14B | 80 | 100 | 100 | 100 | 100 | 80 | 95 | 70 | 60 | 100 | 40 | 85 | 100 | 10 |
| 21B | 85 | 100 | 90 | 100 | 100 | 85 | 100 | 100 | 100 | 100 | 70 | 100 | 95 | 100 |

TABLE IV-B-continued

Pre-Emergence Multi-Weed Herbicide Test
Application Rate - 2.24 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 24B | 100 | 100 | 100 | 100 | 100 | 100 | 100 | 100 | 100 | 100 | 75 | 100 | 95 | — |
| 38B | 100 | 100 | 100 | 100 | 100 | 100 | 100 | 20 | 10 | 100 | 20 | 95 | 100 | 20 |
| 88B | 75 | 100 | 60 | 100 | 100 | 70 | 60 | 20 | 40 | 100 | 0 | 100 | 60 | 20 |
| 89B | 20 | 60 | 30 | 85 | 95 | 55 | 40 | 15 | 20 | 65 | 0 | 100 | 35 | 50 |
| 90B | 60 | 100 | 60 | 100 | 100 | 45 | 30 | 100 | 100 | 100 | 15 | 100 | 50 | 85 |
| 103B | 95 | 100 | 75 | 100 | 100 | 50 | 85 | 100 | 100 | 100 | 80 | 100 | 80 | 40 |
| 104B | 60 | 100 | 60 | 100 | 100 | 45 | 30 | 100 | 100 | 100 | 15 | 100 | 50 | 85 |

— = Specie did not germinate for some reason.

TABLE V-B

Post-Emergence Multi-Weed Herbicide Test
Application Rate - 2.24 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 24B | 35 | 25 | 45 | 60 | 65 | 85 | 90 | 100 | 100 | — | 90 | 100 | 65 | — |
| 88B | 60 | 30 | 30 | 90 | 100 | 80 | 100 | 100 | 100 | 100 | 30 | 100 | 20 | 100 |
| 89B | 50 | 70 | 35 | 90 | 60 | 35 | 20 | 100 | 90 | 100 | 35 | 100 | 15 | 100 |
| 90B | 30 | 100 | 40 | 100 | 70 | 10 | 25 | 100 | 100 | 100 | 30 | 90 | 50 | 95 |
| 103B | 95 | 100 | 70 | 100 | 65 | 75 | 65 | 100 | 100 | 100 | 65 | 100 | 50 | 100 |
| 104B | 30 | 100 | 40 | 100 | 70 | 10 | 25 | 100 | 100 | 100 | 30 | 90 | 50 | 95 |

— = Specie did not germinate for some reason.

TABLE VI-B

Pre-Emergence Multi-Weed Herbicide Test
Application Rate - 1.12 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 1B | 25 | 10 | 30 | 85 | 55 | 0 | — | 55 | — | 100 | — | 75 | 75 | 35 |
| 23B | 55 | 95 | 90 | 100 | 95* | 95 | 95 | 98 | 80 | — | 10 | 100 | 95 | — |
| 68B | 65 | 100 | 60 | 100 | 100* | 6 | 90 | 100 | 90 | 100 | 20 | 100 | 30 | 40 |
| 69B | 70 | 100 | 60 | 100 | 100* | 95 | 95 | 100 | 95 | 100 | 0 | 100 | 85 | 25 |
| 70B | 60 | 100 | 75 | 100 | 100* | 85 | 100 | 100 | 90 | 100 | 25 | 100 | 90 | 25 |
| 76B | 100 | 100 | 85 | 100 | 100* | 85 | 98 | 100 | 95 | — | 35 | 100 | 95 | — |
| 78B | 40 | 70 | 15 | 95 | 75* | 25 | 80 | 65 | 75 | — | 0 | 100 | 80 | — |
| 79B | 100 | 100 | 100 | 100 | 100 | 98 | 100 | 100 | 85 | 100 | 85 | 100 | 95 | — |
| 80B | 98 | 100 | 95 | 100 | 100 | 60 | 98 | 99 | 90 | 100 | 35 | 100 | 85 | — |
| 83B | 20 | 100 | 60 | 100 | 100* | 40 | 90 | 85 | 65 | 100 | 0 | 100 | 85 | — |
| 84B | 0 | 90 | 25 | 98 | 100* | 30 | 90 | 20 | 35 | 100 | 5 | 100 | 50 | — |
| 85B | 80 | 100 | 50 | 100 | 100 | 60 | 90 | 100 | 90 | 100 | 0 | 100 | 95 | — |
| 86B | 60 | 90 | 40 | 100 | 100 | 60 | 70 | 35 | 60 | 100 | 100 | 100 | — | — |
| 87B | 0 | 90 | 15 | 100 | 85 | 15 | 70 | 40 | 60 | 100 | 40 | 90 | 20 | — |
| 92B | 20 | 40 | 10 | 95 | 40 | 10 | 60 | 65 | 30 | 100 | 0 | 55 | 60 | 0 |
| 93B | 60 | 95 | 20 | 100 | 100 | 75 | 100 | 100 | 100 | 100 | 0 | 100 | 40 | 35 |
| 94B | 0 | 80 | 40 | 100 | 95 | 25 | 85 | 80 | 40 | 100 | 10 | 85 | 55 | 10 |
| 95B | 98 | 100 | 30 | 100 | 100 | 40 | 90 | 100 | 100 | 100 | 40 | 100 | 90 | 30 |
| 96B | 100 | 100 | 75 | 100 | 100 | 95 | 100 | 100 | 100 | 100 | 60 | 100 | 85 | 100 |
| 97B | 100 | 100 | 90 | 100 | 100 | 95 | 100 | 100 | 100 | 100 | 60 | 100 | 95 | 100 |
| 98B | 95 | 100 | 100 | 100 | 100 | 80 | 100 | 100 | 100 | 100 | 50 | 100 | 100 | 60 |
| 99B** | — | 100 | 75 | 100 | 100* | 20 | 75 | 50 | 75 | 95 | 0 | — | 85 | 30 |
| 100B | 100 | 98 | 98 | 100 | 100 | 90 | 95 | 100 | 75 | 100 | 70 | 100 | 95 | 40 |
| 102B | 0 | 100 | 25 | 100 | 90 | 75 | 95 | 60 | 60 | 100 | 30 | 100 | 90 | — |

* = seedling johnsongrass (*Sorghum halepense*) was substituted for rox-orange sorghum.
** = Application rate was 0.56 kg/ha
— = Specie did not germinate for some reason.

TABLE VII-B

Post-Emergence Multi-Weed Herbicide Test
Application Rate - 1.12 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 1B | 45 | 35 | 40 | 90 | 35 | 10 | — | 60 | — | 75 | — | 60 | 50 | 55 |
| 23B | 90 | 100 | 80 | 90 | 90* | 90 | 90 | 80 | 90 | 90 | 40 | 70 | 25 | — |
| 68B | 50 | 60 | 40 | 85 | 80* | 75 | 100 | 95 | 90 | 85 | 55 | 100 | 40 | — |
| 69B | 70 | 80 | 35 | 90 | 90* | 80 | 90 | 80 | 85 | 90 | 20 | 90 | 25 | — |
| 70B | 100 | 90 | 80 | 100 | 100* | 95 | 100 | 100 | 95 | 80 | 30 | 75 | 45 | 90 |
| 76B | 100 | 100 | 98 | 100 | 100* | 100 | 100 | 100 | 100 | 100 | 60 | 100 | 40 | — |
| 78B | 100 | 90 | 80 | 85 | 100* | 70 | 90 | 100 | 100 | 100 | 0 | 90 | 45 | — |
| 79B | 80 | 35 | 45 | 70 | 60* | 70 | 70 | 45 | 98 | 100 | 35 | 90 | 20 | — |
| 80B | 60 | 70 | 25 | 90 | 60* | 60 | 85 | 70 | 90 | 100 | 15 | 100 | 25 | 100 |
| 85B | 95 | 100 | 65 | 100 | 80 | 90 | 100 | 100 | 100 | 100 | 25 | 100 | 85 | — |

TABLE VII-B-continued

Post-Emergence Multi-Weed Herbicide Test
Application Rate - 1.12 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 86B | 30 | 60 | 20 | 75 | 50 | 50 | 60 | 50 | 65 | 100 | 10 | 100 | 20 | 80 |
| 87B | 0 | 0 | 0 | 100 | 45 | 20 | 30 | 60 | 90 | 80 | 0 | 100 | 30 | 45 |
| 92B | 20 | 80 | 10 | 85 | 15 | 0 | 30 | 100 | 40 | 100 | 0 | 60 | 60 | 30 |
| 93B | 70 | 100 | 25 | 100 | 100 | 85 | 100 | 100 | 100 | 100 | 100 | 100 | 80 | — |
| 94B | 20 | 70 | 30 | 90 | 80 | 30 | 20 | 100 | 100 | 100 | 60 | 30 | 30 | 100 |
| 95B | 60 | 90 | 15 | 95 | 95 | 25 | 90 | 100 | 100 | 100 | 75 | 100 | 70 | 100 |
| 96B | 50 | 80 | 0 | 90 | 70 | 30 | 100 | 100 | 100 | 100 | 40 | 100 | 20 | 100 |
| 97B | 65 | 100 | 35 | 100 | 75 | 70 | 80 | 100 | 100 | 100 | 50 | 100 | 50 | 100 |
| 98B | 95 | 100 | 65 | 95 | 90 | 100 | 95 | 100 | 100 | 90 | 40 | 80 | 60 | 95 |
| 99B** | — | 100 | 95 | 90 | 90* | 90 | 100 | 25 | 80 | 40 | 100 | — | 35 | 75 |
| 100B | 65 | 75 | 60 | 80 | 75 | 60 | 85 | 100 | 100 | 100 | 45 | 100 | 65 | 60 |
| 102B | 30 | 75 | 20 | 80 | 60 | 0 | 40 | 70 | 100 | 100 | 30 | 100 | 75 | — |

\* = Seedling johnsongrass (*Sorghum halepense*) was substituted for rox-orange sorghum.
\*\* = Application rate was 0.56 kg/ha.
— = Specie did not germinate for some reason.

TABLE IV-C

Pre-Emergence Multi-weed Herbicide Test
Application Rate - 1.12 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 2C | 0 | 100 | 0 | 100 | — | 45 | 70 | 65 | 50 | 100 | 15 | 100 | 90 | — |

— = Not tested.

TABLE V-C

Post-Emergence Multi-Weed Herbicidal Activity
Application Rate - 1.12 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 2D | 0 | 30 | 0 | 100 | — | 0 | 60 | 85 | 95 | 100 | 100 | 90 | 40 | — |

— = Not tested.

TABLE IV-D

Pre-Emergence Multi-weed Herbicide Test
Application Rate - 2.24 kg/ha

| Cmpd. No. | DB | FT | ARG | WG | SHC | WO | BSG | AMG | SESB | VL | SP | MD | YNG | CB |
|---|---|---|---|---|---|---|---|---|---|---|---|---|---|---|
| 7D | 100 | 100 | 100 | 100 | 100 | 100 | 100 | 100 | 100 | 100 | 100 | 100 | 95 | 100 |
| 8D | 100 | 100 | 100 | 100 | 100 | 100 | 100 | 100 | 100 | 100 | 100 | 100 | 95 | — |
| 16D$^a$ | 70 | 100 | 65 | 100 | 100 | 60 | 98 | 55 | 100 | 100 | 90 | 100 | 90 | — |
| 24D | 100 | 100 | 100 | 100 | 100 | 100 | 100 | 100 | 100 | 100 | 100 | 100 | 100 | — |
| 29D | 100 | 100 | 100 | 100 | 100 | 100 | 100 | 100 | 100 | 100 | 30 | 100 | 95 | 80 |
| 33D | 75 | 15 | 60 | 90 | 90 | 20 | 95 | 100 | 100 | 100 | 60 | 100 | 95 | 100 |
| 53D | 100 | 100 | 100 | 100 | 100 | 90 | 100 | 100 | 100 | 100 | 100 | 100 | 95 | 100 |
| 57D | 100 | 100 | 25 | 100 | 100 | 30 | 25 | 100 | 100 | 100 | 100 | 100 | 95 | 100 |
| 64D$^a$ | — | 0 | 0 | 95 | 35 | 0 | 15 | 50 | 75 | 75 | 25 | — | 75 | 40 |
| 66D$^a$ | — | 0 | 15 | 15 | 50 | 20 | 50 | 100 | 100 | 75 | 0 | — | 90 | 100 |
| 67D$^a$ | — | 0 | 0 | 100 | 100 | 0 | 25 | 95 | 75 | 50 | 25 | — | 30 | 75 |
| 69D$^a$ | — | 30 | 0 | 100 | 100 | 0 | 70 | 100 | 100 | 100 | 35 | — | 95 | 100 |
| 70D$^a$ | — | 100 | 10 | 100 | 100 | 25 | 65 | 100 | 100 | 100 | 0 | — | 95 | 100 |

— = Not tested.
$^a$ = Tested at 0.28 kg/ha.

TABLE V-D

Pre-Emergence Multi-weed Herbicide Test
Application Rate - 1.12 kg/ha

| Cmpd. No. | DB | FT | ARG | WG | SHC | WO | BSG | AMG | SESB | VL | SP | MD | YNG | CB |
|---|---|---|---|---|---|---|---|---|---|---|---|---|---|---|
| 34D | 90 | 85 | 30 | 95 | — | 45 | 98 | 75 | 100 | 100 | 40 | 100 | 50 | — |
| 35D | 100 | 85 | 70 | 100 | — | 90 | 100 | 100 | 100 | 100 | 40 | 100 | 75 | — |
| 40D | 100 | 100 | 20 | 100 | — | 70 | 100 | 98 | 98 | 100 | 20 | 100 | 50 | — |
| 41D | 100 | 100 | 80 | 100 | — | 60 | 100 | 100 | 100 | 100 | 25 | 100 | 95 | — |
| 42D | 50 | 60 | 40 | 85 | — | 30 | 100 | 100 | 100 | 100 | 100 | 100 | 90 | — |
| 43D | 90 | 95 | 60 | 100 | — | 30 | 98 | 100 | 98 | 100 | 45 | 100 | 95 | — |
| 44D | 60 | 100 | 20 | 100 | — | 60 | 100 | 100 | 90 | 100 | 20 | 100 | 80 | — |
| 45D | 95 | 100 | 35 | 100 | — | 60 | 90 | 100 | 100 | 100 | 0 | 100 | 90 | — |
| 46D | 100 | 100 | 90 | 100 | — | 95 | 100 | 100 | 100 | 100 | 40 | 100 | 95 | — |

TABLE V-D-continued

Pre-Emergence Multi-weed Herbicide Test
Application Rate - 1.12 kg/ha

| Cmpd. No. | DB | FT | ARG | WG | SHC | WO | BSG | AMG | SESB | VL | SP | MD | YNG | CB |
|---|---|---|---|---|---|---|---|---|---|---|---|---|---|---|
| 47D | 100 | 100 | 100 | 100 | — | 98 | 100 | 100 | 98 | 100 | 30 | 100 | 95 | — |
| 48D | 100 | 100 | 100 | 100 | — | 100 | 100 | 100 | 100 | 100 | 90 | 100 | 100 | — |
| 49D | 100 | 100 | 100 | 100 | — | 100 | 100 | 100 | 100 | 100 | 90 | 100 | — | — |
| 50D | 100 | 100 | 100 | 100 | 100 | 85 | 100 | 100 | 100 | 100 | 90 | 100 | 98 | — |
| 54D | 100 | 100 | 85 | 100 | 100 | 15 | 100 | 25 | 100 | 100 | 65 | 100 | 95 | 100 |
| 55D | 85 | 100 | 35 | 100 | 98 | 15 | 100 | 15 | 100 | 100 | 65 | 100 | 95 | — |
| 56D | 100 | 100 | 100 | 100 | 100 | 100 | 100 | 100 | 100 | 100 | 100 | 100 | 100 | 100 |
| 58D | 98 | 100 | 40 | 95 | 40 | 20 | 95 | 100 | 100 | 100 | 85 | 100 | 100 | 95 |
| 59D | 100 | 100 | 100 | 100 | 100 | 90 | 100 | 100 | 100 | 100 | 100 | 100 | 85 | 80 |
| 60D | 100 | 100 | 100 | 100 | 100 | 100 | 100 | 100 | 100 | 100 | 75 | 100 | 85 | 80 |

— = Not tested.

TABLE VI-D

Pre-Emergence Multi-weed Herbicide Test
Application Rate - 0.56 kg/ha

| Cmpd. No. | DB | FT | ARG | WG | SHC | WO | BSG | AMG | SESB | VL | SP | MD | YNG | CB |
|---|---|---|---|---|---|---|---|---|---|---|---|---|---|---|
| 61D | — | 100 | 65 | 100 | 65 | 20 | 80 | 20 | 40 | 80 | 10 | — | 20 | 0 |
| 62D | — | 50 | 35 | 70 | 50 | 0 | 0 | 0 | 25 | 50 | 0 | — | 0 | 0 |
| 63D | 100 | 100 | 100 | 100 | 100 | 95 | 100 | 90 | 95 | 100 | 75 | 100 | 100 | 85 |
| 68D | — | 0 | 20 | 0 | 0 | 0 | 0 | 60 | 100 | 100 | 90 | — | 75 | 75 |
| 71D | — | 50 | 40 | 50 | 75 | 40 | 35 | 75 | 50 | 70 | 0 | — | 75 | 75 |
| 72D | — | 35 | 60 | 100 | 85 | 50 | 100 | 25 | 65 | 100 | 35 | — | 100 | 35 |
| 73D | — | 90 | 70 | 100 | 95 | 25 | 0 | 70 | 100 | 100 | 0 | — | 50 | 25 |

— = Not tested.

TABLE VII-D

Post-Emergence Multi-Weed Herbicidal Activity
Application Rate - 2.24 kg/ha

| Cmpd. No. | DB | FT | ARG | WG | SHC | WO | BSG | AMG | SESB | VL | SP | MD | YNG | CB |
|---|---|---|---|---|---|---|---|---|---|---|---|---|---|---|
| 7D | 100 | 100 | 100 | 100 | 80 | 90 | 10 | 95 | 100 | 100 | 55 | 100 | 45 | 100 |
| 16D[a] | 100 | 85 | 35 | 100 | 100 | 100 | 100 | 100 | 100 | 100 | 100 | 100 | 85 | 70 |
| 24D | 100 | 100 | 100 | 100 | 100 | 100 | 100 | 100 | 100 | 100 | 100 | 100 | 100 | — |
| 29D | 100 | 100 | 60 | 100 | 90 | 100 | 100 | 100 | 100 | 100 | 100 | 100 | 100 | — |
| 33D | 90 | 98 | 85 | 100 | 100 | 80 | 100 | 100 | 100 | 100 | 90 | 100 | 90 | 100 |
| 53D | 100 | 100 | 60 | 100 | 100 | 100 | 100 | 100 | 100 | 100 | 100 | 100 | 100 | — |
| 57D | 25 | 40 | 10 | 100 | 10 | 0 | 10 | 100 | 95 | 100 | 35 | 100 | — | 100 |
| 64D[a] | — | 0 | 0 | 90 | 0 | 0 | 85 | 40 | 100 | 80 | 50 | — | 35 | 100 |
| 66D[a] | — | 0 | 0 | 65 | 0 | 0 | 70 | 75 | 80 | 75 | 0 | — | 25 | 75 |
| 67D[a] | — | 0 | 0 | 75 | 35 | 0 | 40 | 70 | 80 | 60 | 0 | — | 0 | 100 |
| 69D[a] | — | 0 | 0 | 80 | 35 | 0 | 100 | 90 | 100 | 100 | 40 | — | 35 | 100 |
| 70D[a] | — | 100 | 0 | 100 | 70 | 90 | 90 | 100 | 100 | 100 | 30 | — | 25 | 100 |

— = Not tested.
[a] = Tested at 0.28 kg/ha.

TABLE VIII-D

Post-Emergence Multi-weed Herbicide Test
Application Rate - 1.12 kg/ha

| Cmpd. No. | DB | FT | ARG | WG | SHC | WO | BSG | AMG | SESB | VL | SP | MD | YNG | CB |
|---|---|---|---|---|---|---|---|---|---|---|---|---|---|---|
| 34D | 90 | 85 | 30 | 95 | — | 45 | 98 | 75 | 100 | 100 | 40 | 100 | 50 | — |
| 35D | 100 | 85 | 70 | 100 | — | 90 | 100 | 100 | 100 | 100 | 40 | 100 | 75 | — |
| 40D | 75 | 100 | 5 | 100 | — | 50 | 75 | 100 | 100 | 100 | 40 | 100 | 30 | — |
| 41D | — | — | — | — | — | — | — | — | — | — | — | — | — | — |
| 42D | 40 | 100 | 35 | 100 | — | 50 | 80 | 100 | 100 | 100 | 80 | 100 | 70 | — |
| 43D | 60 | 70 | 20 | 100 | — | 55 | 60 | 100 | 100 | 100 | 95 | 100 | 70 | — |
| 44D | — | — | — | — | — | — | — | — | — | — | — | — | — | — |
| 45D | — | — | — | — | — | — | — | — | — | — | — | — | — | — |
| 46D | — | — | — | — | — | — | — | — | — | — | — | — | — | — |
| 47D | 90 | 100 | 35 | 100 | — | 75 | 90 | 100 | 100 | 100 | 25 | 100 | 45 | — |
| 48D | 80 | 100 | 60 | 100 | — | 60 | 80 | 100 | 100 | 100 | 85 | 100 | 60 | — |
| 49D | — | — | — | — | — | — | — | — | — | — | — | — | — | — |
| 50D | 90 | 80 | 60 | 95 | 80 | 90 | 100 | 100 | 100 | 100 | 65 | 100 | 80 | — |
| 54D | 35 | 50 | 30 | 100 | 30 | 15 | 90 | 100 | 100 | 100 | 100 | 100 | 95 | — |
| 55D | 100 | 100 | 20 | 100 | 90 | 20 | 100 | 90 | 100 | 100 | 100 | 100 | — | — |
| 56D | 75 | 90 | 75 | 95 | 90 | 25 | 100 | 100 | 100 | 100 | 90 | 100 | 90 | 100 |
| 58D | 70 | 100 | 40 | 100 | 95 | 30 | 95 | 100 | 95 | 100 | 95 | 100 | 95 | 85 |
| 59D | 90 | 100 | 95 | 100 | 100 | 50 | 100 | 100 | 100 | 100 | 95 | 100 | 100 | 95 |

TABLE VIII-D-continued

Post-Emergence Multi-weed Herbicide Test
Application Rate - 1.12 kg/ha

| Cmpd. No. | DB | FT | ARG | WG | SHC | WO | BSG | AMG | SESB | VL | SP | MD | YNG | CB |
|---|---|---|---|---|---|---|---|---|---|---|---|---|---|---|
| 60D | 95 | 100 | 100 | 100 | 100 | 75 | 95 | 100 | 100 | 100 | 95 | 100 | 100 | 100 |

— = Not tested.

TABLE IX-D

Post-Emergence Multi-weed Herbicide Test
Application Rate - 0.56 kg/ha

| Cmpd. No. | DB | FT | ARG | WG | SHC | WO | BSG | AMG | SESB | VL | SP | MD | YNG | CB |
|---|---|---|---|---|---|---|---|---|---|---|---|---|---|---|
| 61D | — | 40 | 0 | 50 | 35 | 0 | 40 | 75 | 95 | 100 | 0 | — | 25 | 50 |
| 62D | — | 35 | 0 | 20 | 0 | 0 | 20 | 35 | 60 | 100 | 0 | — | 0 | 100 |
| 63D | 100 | 100 | 85 | 98 | 85 | 100 | 100 | 100 | 100 | 100 | 100 | 85 | 85 | 95 |
| 68D | — | 30 | 40 | 85 | 0 | 25 | 60 | 80 | 95 | 100 | 95 | — | 0 | 80 |
| 71D | — | 50 | 0 | 80 | 65 | 0 | 75 | 100 | 80 | 100 | 50 | — | 25 | 100 |
| 72D | — | 90 | 70 | 80 | 50 | 50 | 75 | 85 | 100 | 100 | 90 | — | 100 | 100 |
| 73D | — | 100 | 15 | 100 | 75 | 75 | 85 | 100 | 100 | 90 | 60 | — | 80 | 100 |

(—) = Not tested.

TABLE IV-E

Pre-Emergence Multi-weed Herbicide Test
Application Rate - 2.24 kg/ha

| Cmpd. No. | DB | FT | ARG | WG | JG | WO | BSG | AMG | SESB | VL | SP | MD | YNG |
|---|---|---|---|---|---|---|---|---|---|---|---|---|---|
| 17E | 95 | 85 | 35 | 100 | 85 | 25 | 90 | 100 | 100 | 100 | 40 | 100 | 95 |
| 18E | 0 | 0 | 0 | 50 | 20 | 0 | 15 | 60 | 45 | 100 | 0 | 100 | — |

TABLE V-E

Pre-Emergence Multi-weed Herbicide Test
Application Rate - 1.12 kg/ha

| Cmpd. No. | DB | FT | ARG | WG | JG | WO | BSG | AMG | SESB | VL | SP | MD | YNG |
|---|---|---|---|---|---|---|---|---|---|---|---|---|---|
| 7E | 30 | 70 | 20 | 100 | 75 | 0 | 90 | 100 | 95 | 100 | 100 | 100 | 90 |
| 8E | 95 | 95 | 45 | 100 | 98 | 25 | 90 | 100 | 95 | 100 | 90 | 100 | 90 |
| 9E | 10 | 70 | 40 | 100 | 20 | 0 | 80 | 100 | 85 | 100 | 40 | 100 | 95 |
| 10E | 100 | 100 | 10 | 100 | 40 | 0 | 90 | 100 | 100 | 100 | 80 | 100 | 100 |
| 11E | 90 | 100 | 90 | 100 | 100 | 65 | 100 | 100 | 90 | 100 | 30 | 100 | 65 |
| 12E | 100 | 100 | 80 | 100 | 100 | 85 | 90 | 100 | 100 | 100 | 85 | 100 | 90 |
| 13E | 0 | 100 | 10 | 100 | 100 | 80 | 70 | 80 | 90 | 100 | 70 | 100 | 80 |
| 15E | 0 | 10 | 0 | 90 | 0 | 0 | 15 | 35 | 30 | 100 | 10 | 85 | 75 |
| 19E | 100 | 90 | 0 | 100 | 20 | 10 | 40 | 95 | 100 | 100 | 100 | 100 | 65 |

TABLE VI-E

Post-Emergence Multi-Weed Herbicidal Activity
Application Rate - 2.24 kg/ha

| Cmpd. No. | DB | FT | ARG | WG | JG | WO | BSG | AMG | SESB | VL | SP | MD | YNG |
|---|---|---|---|---|---|---|---|---|---|---|---|---|---|
| 17E | 80 | 100 | 55 | 95 | 90 | 20 | 60 | 100 | 100 | 100 | 75 | 100 | 70 |
| 18E | 0 | 100 | 0 | 98 | 20 | 0 | 10 | 70 | 60 | 100 | 10 | 100 | 45 |

TABLE VII-E

Post-Emergence Multi-Weed Herbicidal Activity
Application Rate - 1.12 kg/ha

| Cmpd. No. | DB | FT | ARG | WG | JG | WO | BSG | AMG | SESB | VL | SP | MD | YNG |
|---|---|---|---|---|---|---|---|---|---|---|---|---|---|
| 7E | 25 | 30 | 0 | 70 | 60 | 20 | 90 | 75 | 95 | 85 | 50 | 100 | 35 |
| 8E | 80 | 80 | 20 | 70 | 70 | 40 | 80 | 50 | 80 | 80 | 60 | 60 | 35 |
| 9E | 0 | 30 | 0 | 75 | 15 | 25 | 100 | 95 | 100 | 100 | 60 | 100 | 25 |
| 10E | 60 | 80 | 20 | 70 | 35 | 25 | 80 | 75 | 90 | 90 | 70 | 100 | 45 |
| 11E | 45 | 100 | 20 | 100 | 100 | 40 | 50 | 100 | 100 | 100 | 20 | 100 | 35 |
| 12E | 70 | 60 | 30 | 100 | 100 | 80 | 98 | 90 | 100 | 100 | 70 | 98 | 40 |
| 13E | 25 | 100 | 10 | 100 | 100 | 85 | 100 | 80 | 100 | 100 | 10 | 90 | 25 |
| 15E | 30 | 65 | 10 | 90 | 50 | 30 | 20 | 85 | 80 | 98 | 30 | 65 | 15 |

TABLE VII-E-continued

Post-Emergence Multi-Weed Herbicidal Activity
Application Rate - 1.12 kg/ha

| Cmpd. No. | DB | FT | ARG | WG | JG | WO | BSG | AMG | SESB | VL | SP | MD | YNG |
|---|---|---|---|---|---|---|---|---|---|---|---|---|---|
| 19E | 20 | 60 | 10 | 90 | 10 | 15 | 90 | 100 | 100 | 70 | 100 | 40 | 85 |

TABLE IV-F

Pre-Emergence Multi-weed Herbicide Test
Application Rate - 1.12 kg/ha

| Cmpd. No. | DB | FT | ARG | WG | JG | WO | BSG | AMG | SESB | VL | SP | MD | YNG | CB |
|---|---|---|---|---|---|---|---|---|---|---|---|---|---|---|
| 19F | 40 | 35 | 60 | 100 | 90 | 30 | 90 | 100 | 100 | — | 20 | 100 | 90 | — |
| 26F | 25 | 70 | 45 | 95 | 60 | 25 | 85 | 35 | 75 | — | 20 | 100 | 95 | 90 |
| 27F | 45 | 65 | 40 | 100 | 60 | 25 | 80 | 100 | 85 | 100 | 40 | 100 | 95 | 35 |
| 28F | 80 | 100 | 90 | 100 | 100 | 90 | 100 | 70 | 90 | 100 | 30 | 100 | 95 | 35 |
| 29F | 90 | 45 | 75 | 100 | 85 | 40 | 90 | 95 | 90 | 100 | 40 | 100 | 95 | — |
| 30F | 90 | 45 | 75 | 100 | 90 | 75 | 100 | 100 | 80 | 100 | 60 | 100 | 95 | — |
| 31F | 60 | 65 | 75 | 100 | 100 | 55 | 95 | 100 | 100 | 100 | 100 | 100 | 95 | — |
| 32F | 90 | 100 | 90 | 100 | 100 | 65 | 85 | 100 | 90 | 100 | 95 | 100 | 85 | — |
| 33F | 100 | 100 | 95 | 100 | 100 | 95 | 100 | 100 | 100 | 100 | 25 | 100 | 90 | — |
| 35F | 90 | 100 | 100 | 100 | — | 90 | 90 | 100 | 90 | 100 | 10 | 100 | 75 | — |
| 36F | 90 | 35 | 85 | 100 | — | 15 | 80 | 95 | 90 | 100 | 50 | 100 | 95 | — |
| 39F | 100 | 100 | 100 | 100 | 100 | 95 | 100 | 100 | 100 | 100 | 100 | 100 | 98 | — |
| 40F | 100 | 100 | 80 | 100 | 100 | 70 | 100 | 100 | 100 | 100 | 90 | 100 | 95 | — |
| 41F | 100 | 100 | 100 | 100 | 100 | 100 | 100 | 100 | 100 | 100 | 60 | 100 | 98 | — |
| 42F | 60 | 100 | 85 | 100 | 100 | 70 | 95 | 100 | 95 | 100 | 10 | 100 | 95 | 50 |
| 43F | 85 | 100 | 25 | 100 | 60 | 25 | 98 | 100 | 100 | 100 | 100 | 100 | 90 | 100 |
| 44F | 0 | 80 | 10 | 85 | 0 | 0 | 75 | 0 | 30 | 100 | 0 | 100 | 0 | 10 |
| 45F | 25 | 100 | 40 | 100 | 60 | 0 | 65 | 60 | 60 | 100 | 50 | 100 | 70 | 0 |
| 50F | — | 100 | 50 | 100 | 35 | 35 | 75 | | 100 | 100 | — | | | |

(—) = Not tested.

TABLE V-F

Pre-Emergence Multi-weed Herbicide Test
Appication Rate - 0.56 kg/ha

| Cmpd. No. | DB | FT | ARG | WG | JG | WO | BSG | AMG | SESB | VL | SP | MD | YNG | CB |
|---|---|---|---|---|---|---|---|---|---|---|---|---|---|---|
| 46F | 0 | 65 | 35 | 75 | 65 | 0 | 0 | 0 | 35 | 100 | 25 | 90 | 80 | 0 |
| 47F | — | 60 | 35 | 100 | 100 | 0 | 90 | 100 | 100 | 100 | 70 | — | 100 | 75 |
| 48F | — | 75 | 20 | 90 | 60 | 0 | 15 | 70 | 35 | 90 | 0 | — | 20 | 40 |
| 49F | — | 60 | 10 | 100 | 60 | 0 | 50 | 100 | 95 | 100 | 40 | — | 90 | 100 |
| 51F | — | 40 | 10 | 95 | 40 | 10 | 50 | 65 | 100 | 100 | 0 | — | 95 | 65 |

(—) - Not tested.

TABLE VI-F

Post-Emergence Multi-Weed Herbicidal Activity
Application Rate -- 2.24 kg/ha

| Cmpd. No. | DB | FT | ARG | WG | JG | WO | BSG | AMG | SESB | VL | SP | MD | YNG | CB |
|---|---|---|---|---|---|---|---|---|---|---|---|---|---|---|
| 19F | 100 | 90 | 65 | 100 | 100 | 98 | 100 | 100 | 100 | 100 | 60 | 100 | 70 | 100 |
| 26F | 60 | 75 | 60 | 95 | 45 | 50 | 90 | 50 | 90 | 100 | 40 | 90 | 60 | — |
| 27F | 80 | 70 | 65 | 95 | 100 | 90 | 100 | 100 | 100 | 100 | 85 | 100 | 75 | — |
| 28F | 80 | 100 | 75 | 90 | 85 | 80 | 100 | 80 | 80 | 100 | 30 | 100 | 85 | 85 |
| 29F | 85 | 70 | 55 | 90 | 98 | 90 | 100 | 100 | 100 | 100 | 35 | 100 | 60 | 100 |
| 30F | 90 | 80 | 40 | 90 | 85 | 80 | 80 | 70 | 100 | 100 | 20 | 100 | 40 | — |
| 31F | 100 | 80 | 20 | 100 | 100 | 100 | 100 | 100 | 100 | 100 | 100 | 100 | 85 | — |
| 32F | 70 | 90 | 60 | 100 | 100 | 98 | 100 | 100 | 100 | 100 | 100 | 100 | 60 | — |
| 33F | 95 | 100 | 80 | 100 | 90 | 100 | 100 | 100 | 100 | 100 | 70 | 100 | 40 | — |
| 35F | 70 | 90 | 40 | 100 | — | 100 | 100 | 100 | 100 | 100 | 98 | 100 | 30 | — |
| 36F | 85 | 100 | 35 | 100 | — | 20 | 100 | 100 | 100 | 100 | 100 | 100 | 15 | — |
| 39F | 100 | 100 | 85 | 100 | 100 | 100 | 100 | 100 | 100 | 100 | 100 | 100 | 90 | 100 |
| 40F | 100 | 100 | 30 | 100 | 100 | 100 | 100 | 100 | 100 | 100 | 90 | 100 | 75 | — |
| 41F | 100 | 100 | 35 | 90 | 70 | 100 | 90 | 100 | 100 | 100 | 50 | 100 | 70 | — |
| 42F | 45 | 100 | 50 | 100 | 70 | 55 | 80 | 100 | 100 | 100 | 70 | 100 | 75 | 100 |
| 43F | 25 | 80 | 15 | 98 | 35 | 0 | 20 | 100 | 100 | 100 | 100 | 100 | 60 | 95 |
| 44F | 0 | 15 | 0 | 65 | 0 | 0 | 0 | 70 | 100 | 100 | 40 | 100 | 0 | 100 |
| 45F | 0 | 75 | 35 | 70 | 35 | 0 | 60 | 50 | 85 | 100 | 50 | 100 | 75 | 70 |
| 50F | — | 40 | 0 | 75 | 45 | 40 | 60 | 100 | 100 | 95 | 30 | — | 60 | 100 |

(—) = Not tested.

TABLE VII-F

Post-Emergence Multi-Weed Herbicidal Activity
Application Rate - 0.56 kg/ha

| Cmpd. No. | DB | FT | ARG | WG | JG | WO | BSG | AMG | SESB | VL | SP | MD | YNG | CB |
|---|---|---|---|---|---|---|---|---|---|---|---|---|---|---|
| 46F | 25 | 35 | 20 | 50 | 35 | 35 | 0 | 20 | 75 | 100 | 35 | 95 | — | 50 |
| 47F | — | 75 | 25 | 90 | 40 | 25 | 80 | 100 | 100 | 100 | 80 | — | 75 | 100 |
| 48F | — | 50 | 35 | 80 | 35 | 40 | 0 | 75 | 100 | 85 | 15 | — | 50 | 75 |
| 49F | — | 35 | 0 | 75 | 30 | 0 | 20 | 100 | 100 | 100 | 80 | — | 25 | 85 |
| 51F | — | 35 | 0 | 80 | 35 | 20 | 70 | 50 | 95 | 95 | 25 | — | 65 | 50 |

(—) = Not Tested.

The compounds of the present invention and their salts are useful as herbicides and can be applied in a variety of ways at various concentrations. In practice, the compounds or salts are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds or salts can be formulated as granules of relatively large particle size, as wettable powders, as emulsifiable concentrates, as powdery dusts, as flowables, as solutions or as any of several other known types of formulations, depending upon the desired mode of application. These formulations may contain as little as about 0.5% to as much as about 95% or more by weight of active ingredient. A herbicidally effective amount depends upon the nature of the seeds or plants to be controlled and the rate of application varies from about 0.01 to approximately 10 pounds per acre, preferably from about 0.02 to about 4 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound or salt with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which may be coated with the toxicant. Granular formulations normally are prepared to contain about 0.1% to about 25% of active ingredients which may include surface-active agents such heavy aromatic naphthas, kerosene or other petroleum fractions, or vegetable oils; and/or stickers such as dextrins, glue or synthetic resins.

Typical wetting, dispersing or emulsifying agents and adjuvants used in agricultural formulations include, for example, the alkyl and alkylaryl sulfonates and sulfates and their salts; polyhydric alcohols; polyethoxylated alcohols, esters and fatty amines; and other types of surface-active agents, many of which are available in commerce. The surface-active agent, when used, normally comprises from 0.1% to 30% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as water, acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention can be applied to the plants in the conventional manner. Thus, the dust and liquid compositions can be applied to the plant by the use of powder-dusters, boom and hand sprayers and spray dusters. The compositions can also be applied from airplanes as a dust or a spray or by rope wick applications because they are effective in very low dosages. In order to modify or control growth of germinating seeds or emerging seedlings, as a typical example, the dust and liquid compositions can be applied to the soil according to conventional methods and can be distributed in the soil to a depth of at least $\frac{1}{2}$0 inch below the soil surface. It is not necessary that the phytotoxic compositions be mechanically admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations. In the following examples the herbicidal compound can be substituted with the herbicidal salt of the compound.

| General Formula with Ranges | | Specific Formula | |
|---|---|---|---|
| EMULSIFIABLE CONCENTRATE FORMULATIONS | | | |
| Herbicidal compound | 5-55 | herbicidal compound | 24 |
| surfactant(s) | 5-25 | proprietary blend of oil-soluble sulfonates and polyoxyethylene ethers | 10 |
| solvent(s) | 20-90 | | |
| | 100% | polar solvent | 27 |
| | | petroleum hydrocarbon | 39 |
| | | | 100% |
| WETTABLE POWDER FORMULATIONS | | | |
| herbicidal compound | 3-90 | herbicidal compound | 80 |
| wetting agent | 0.5-2 | sodium dialkyl naphthalene sulfonate | 0.5 |
| dispersing agent | 1-8 | | |
| diluent(s) | 8.5-87 | sodium lignosulfonate | 7 |
| | 100% | attapulgite clay | 12.5 |
| | | | 100% |
| EXTRUDED GRANULAR FORMULATIONS | | | |
| herbicidal compound | 1-20 | herbicidal compound | 10 |
| binding agent | 0-10 | lignin sulfonate | 5 |
| diluent(s) | 70-99 | calcium carbonate | 85 |
| | 100% | | 100% |
| FLOWABLE FORMULATIONS | | | |
| herbicidal compound | 20-70 | herbicidal compound | 45 |
| surfactant(s) | 1-10 | polyoxyethylene ether | 5 |
| suspending agent(s) | 0.05-1 | attagel | 0.05 |
| antifreeze agent | 1-10 | propylene glycol | 10 |
| antimicrobial agent | 1-10 | 1,2-benzisothiazoline-3-one | 0.03 |
| antifoam agent | 0.1-1 | silicone defoamer | 0.02 |
| solvent | 7.95-77.85 | water | 39.9 |
| | 100% | | 100% |

When salts are used as the active ingredient in the herbicidal compositions of this invention it is recommended to use salts that are agriculturally acceptable.

The phytotoxic compositions of this invention can also contain other additives, for example, fertilizers, other herbicides and other pesticides, used as adjuvant or in combination with any of the above-described adjuvants. Fertilizers useful in combination with the active ingredients include, for example, ammonium nitrate, urea and superphosphate.

We claim:

1. Compounds having the structural formula

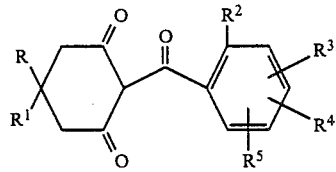

wherein

R and $R^1$ are hydrogen, $C_1$-$C_4$ alkyl, $R^aOC(O)$—, where $R^a$ is $C_1$-$C_4$ alkyl;

$R^2$ is chlorine, bromine, or iodine; and $R^3$, $R^4$ and $R^5$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein $R^b$ is $C_1$-$C_4$ alkyl, $C_1$-$C_4$ haloalkyl, phenyl, benzyl, —$NR^dR^e$ wherein $R^d$ and $R^e$ independently are hydrogen or $C_1$-$C_4$ alkyl; and n is the integer 0, 1 or 2;

wherein $R^c$ is $C_1$-$C_4$ alkyl and $R^j$ is hydrogen; (11) $R^fC(O)$ wherein $R^f$ is hydrogen, $C_1$-$C_4$ alkyl, $C_1$-$C_4$ haloalkyl, $C_1$-$C_4$ alkoxy; (12) —$NR^gR^h$ wherein $R^g$ and $R^h$ independently are hydrogen or $C_1$-$C_4$ alkyl; or (13) $R^3$ and $R^4$ together can form a ring structure with two adjacent carbon atoms of the phenyl ring; and their salts.

2. The compounds of claim 1 wherein R and $R^1$ are hydrogen or $C_1$-$C_4$ alkyl; $R^2$ is chlorine, bromine, or iodine; $R^3$ and $R^4$ independently are hydrogen, halogen, $C_1$-$C_4$ alkyl, $C_1$-$C_4$ alkoxy, trifluoromethoxy, cyano, nitro, $C_1$-$C_4$ haloalkyl, $R^bSO_n$ wherein $R^b$ is $C_1$-$C_4$ alkyl, $C_1$-$C_4$ haloalkyl, phenyl, benzyl, —$NR^dR^e$ wherein $R^d$ and $R^e$ independently are hydrogen and $C_1$-$C_4$ alkyl; and n is the integer 0, 1 or 2; $R^cC(O)NH$— wherein $R^c$ is $C_1$-$C_4$ alkyl; $R^fC(O)$— wherein $R^f$ is hydrogen, $C_1$-$C_4$ alkyl, $C_1$-$C_4$ haloalkyl, $C_1$-$C_4$ alkoxy; or —$NR^gR^h$ wherein $R^g$ and $R^h$ independently are hydrogen or $C_1$-$C_4$ alkyl; and $R^5$ is hydrogen and their salts.

3. The compounds of claim 1 wherein R and $R^1$ are hydrogen or methyl; $R^2$ is chlorine or bromine; $R^3$ is hydrogen, chlorine, $C_1$-$C_4$ alkoxy, $R^bSO_n$ wherein $R^b$ is $C_1$-$C_4$ alkyl and n is the integer 0; $R^4$ is hydrogen, chlorine, cyano, nitro, $R^bSO_n$ wherein $R^b$ is $C_1$-$C_4$ alkyl and n is 0 or 2, $SO_2N(CH_3)_2$ or trifluoromethyl; and $R^5$ is hydrogen and their salts.

4. The compounds of claim 2 wherein $R^2$ is chlorine, $R^3$ is substituted at the 3-position, and $R^4$ is substituted at the 4-position and their salts.

5. The compounds of claim 3 wherein R and $R^1$ are hydrogen; $R^2$ is chlorine; $R^3$ is hydrogen, 3-chlorine, 3-methoxy, 3-ethoxy or 3-n-propoxy and $R^4$ is 4-chlorine, 4-bromine, 4-$CH_3SO_2$— or 4-$C_2H_5SO_2$; and $R^5$ is hydrogen and their salts.

6. The compounds of claim 1 wherein R and $R^1$ are hydrogen or $C_1$-$C_4$ alkyl; $R^2$ is chlorine, bromine, or iodine or; $R^3$ is hydrogen, halogen, $C_1$-$C_4$ alkyl, $C_1$-$C_4$ alkoxy, nitro, $C_1$-$C_4$ haloalkyl or $R^bSO_n$ wherein $R^b$ is $C_1$-$C_4$ alkyl and n is the integer 0; $R^4$ is hydrogen, halogen, $C_1$-$C_4$ alkyl, $C_1$-$C_4$ alkoxy, cyano, nitro, $C_1$-$C_4$ haloalkyl or $R^bSO_n$ wherein $R^b$ is $C_1$-$C_4$ alkyl and n is the integer 0, 1 or 2; and $R^5$ is hydrogen and their salts.

7. The compounds of claim 1 wherein R and $R^1$ are hydrogen or methyl; $R^2$ is chlorine, bromine, or iodine; $R^3$ is hydrogen, halogen, methyl, $C_1$-$C_4$ alkoxy, nitro, trifluoromethyl or methylthio; $R^4$ is hydrogen, halogen, methyl, methoxy, cyano, nitro, trifluoromethyl, methylthio or $CH_3SO_2$; and $R^5$ is hydrogen and their salts.

8. The compounds of claim 6 wherein $R^3$ is in the 3-position and $R^4$ is in the 4-position and their salts.

9. The compounds of claim 7 wherein $R^3$ is in the 3-position and $R^4$ is in the 4-position and their salts.

10. The compounds of claim 1 wherein R and $R^1$ are hydrogen or $C_1$-$C_4$ alkyl; $R^2$ is chlorine, bromine, or iodine or; $R^3$ is hydrogen, halogen, $C_1$-$C_4$ alkoxy, or $R^bSO_n$ wherein $R^b$ is $C_1$-$C_4$ alkyl and n is the integer 0; $R^4$ is $R^bSO_n$— wherein $R^b$ is $C_1$-$C_4$ alkyl and n is the integer 2; and $R^5$ is hydrogen.

11. The compounds of claim 1 wherein R and $R^1$ are hydrogen or methyl; $R^2$ is chlorine or bromine; $R^3$ is hydrogen, halogen, methoxy or methylthio; $R^4$ is $R^bSO_n$— wherein $R^b$ is methyl and n is the integer 2; and $R^5$ is hydrogen.

12. The compounds of claim 10 wherein $R^3$ is in the 3-position and $R^4$ is in the 4-position.

13. The compounds of claim 11 wherein $R^3$ is in the 3-position and $R^4$ is in the 4-position.

14. The compound of claim 1 wherein R is hydrogen, $R^1$ is hydrogen, $R^2$ is chlorine, $R^3$ is hydrogen, $R^4$ is 4-chlorine and $R^5$ is hydrogen and its salts.

15. The compound of claim 1 wherein R is hydrogen, $R^1$ is hydrogen, $R^2$ is chlorine, $R^3$ is 3-chlorine, $R^4$ is 4-chlorine and $R^5$ is hydrogen and its salts.

16. The compound of claim 1 wherein R is hydrogen, $R^1$ is hydrogen, $R^2$ is chlorine, $R^3$ is 3-chlorine, $R^4$ is 4-methoxy and $R^5$ is hydrogen and its salts.

17. The compound of claim 1 wherein R is hydrogen, $R^1$ is hydrogen, $R^2$ is chlorine, $R^3$ is hydrogen, $R^4$ is 4-bromine and $R^5$ is hydrogen and its salts.

18. The compound of claim 1 wherein R is hydrogen, $R^1$ is hydrogen, $R^2$ is chlorine, $R^3$ is hydrogen, $R^4$ is 4-$CH_3SO_2$ and $R^5$ is hydrogen and its salts.

19. The sodium, isopropylamine, triethylamine and potassium salts of the compound of claim 15.

20. The method of controlling undesirable vegetation comprising applying to the area where control is desired, an herbicidally effective amount of a compound having the formula

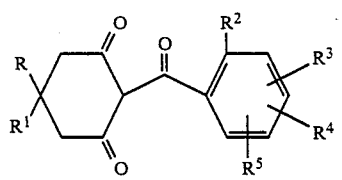

wherein
R and $R^1$ are hydrogen, $C_1$-$C_4$ alkyl, $R^aOC(O)$—, where $R^a$ is $C_1$-$C_4$ alkyl;
$R^2$ is chlorine, bromine, iodine or $C_1$-$C_4$ alkoxy; and
$R^3$, $R^4$ and $R^5$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein $R^b$ is $C_1$-$C_4$ alkyl, $C_1$-$C_4$ haloalkyl, phenyl, benzyl, —$NR^dR^e$ wherein $R^d$ and $R^e$ independently are hydrogen or $C_1$-$C_4$ alkyl; and n is the integer 0, 1 or 2;

wherein $R^c$ is $C_1$-$C_4$ alkyl and $R^j$ is hydrogen; (11) $R^fC(O)$ wherein $R^f$ is hydrogen, $C_1$-$C_4$ alkyl, $C_1$-$C_4$ haloalkyl, $C_1$-$C_4$ alkoxy; (12) —$NR^gR^h$ wherein $R^g$ and $R^h$ independently are hydrogen or $C_1$-$C_4$ alkyl; or (13) $R^3$ and $R^4$ together can form a ring structure with two adjacent carbon atoms of the phenyl ring; and their salts.

21. The method of claim 20 wherein R and $R^1$ are hydrogen or $C_1$-$C_4$ alkyl; $R^2$ is chlorine, bromine, iodine or $C_1$-$C_4$ alkoxy; $R^3$ and $R^4$ independently are hydrogen, halogen, $C_1$-$C_4$ alkyl, $C_1$-$C_4$ alkoxy, trifluoromethoxy; cyano, nitro, $C_1$-$C_4$ haloalkyl, $R^bSO_n$ wherein $R^b$ is $C_1$-$C_4$ alkyl, $C_1$-$C_4$ haloalkyl, phenyl, benzyl, —$NR^dR^e$ wherein $R^d$ and $R^e$ independently are hydrogen and $C_1$-$C_4$ alkyl; and n is the integer 0, 1 or 2; $R^cC(O)NH$— wherein $R^c$ is $C_1$-$C_4$ alkyl; $R^fC(O)$— wherein $R^f$ is hydrogen, $C_1$-$C_4$ alkyl, $C_2$-$C_4$ haloalkyl, $C_1$-$C_4$ alkoxy; or —$NR^gR^h$ wherein $R^g$ and $R^h$ independently are hydrogen or $C_1$-$C_4$ alkyl; and $R^5$ is hydrogen and their salts.

22. The method of claim 20 wherein R and $R^1$ are hydrogen or methyl; $R^2$ is chlorine or bromine; $R^3$ is hydrogen, chlorine, $C_1$-$C_4$ alkoxy, $R^bSO_n$ wherein $R^b$ is $C_1$-$C_4$ alkyl and n is the integer 0; $R^4$ is hydrogen, chlorine, cyano, nitro, $R^bSO_n$ wherein $R^b$ is $C_1$-$C_4$ alkyl and n is 0 or 2, $SO_2N(CH_3)_2$ or trifluoromethyl; and $R^5$ is hydrogen and their salts.

23. The method of claim 21 wherein $R^2$ is chlorine, $R^3$ is substituted at the 3-position, and $R^4$ is substituted at the 4-position and their salts.

24. The method of claim 20 wherein R and $R^1$ are hydrogen; $R^2$ is chlorine; $R^3$ is hydrogen, 3-chlorine, 3-methoxy, 3-ethoxy or 3-n-propoxy and $R^4$ is 4-chlorine, 4-bromine, 4-$CH_3SO_2$— or 4-$C_2H_5SO_2$; and $R^5$ is hydrogen and their salts.

25. The method of claim 20 wherein R an $R^1$ are hydrogen or $C_1$-$C_4$ alkyl; $R^2$ is chlorine, bromine, iodine or $C_1$-$C_4$ alkoxy; $R^3$ is hydrogen, halogen, $C_1$-$C_4$ alkyl, $C_1$-$C_4$ alkoxy, nitro, $C_1$-$C_4$ haloalkyl or $R^bSO_n$ wherein $R^b$ is $C_1$-$C_4$ alkyl and n is the integer 0; $R^4$ is hydrogen, halogen, $C_1$-$C_4$ alkyl, $C_1$-$C_4$ alkoxy, cyano, nitro, $C_1$-$C_4$ haloalkyl or $R^bSO_n$ wherein $R^b$ is $C_1$-$C_4$ alkyl and n is the integer 0, 1 or 2; and $R^5$ is hydrogen and their salts.

26. The method of claim 20 wherein R and $R^1$ are hydrogen or methyl; $R^2$ is chlorine, bromine, iodine or methoxy; $R^3$ is hydrogen, halogen methyl, $C_1$-$C_4$ alkoxy, nitro, trifluoromethyl or methylthio; $R^4$ is hydrogen, halogen, methyl, methoxy, cyano, nitro, trifluoromethyl, methylthio or $CH_3SO_2$; and $R^5$ is hydrogen and their salts.

27. The method of claim 25 wherein $R^3$ is in the 3-position and $R^4$ is in the 4-position and their salts.

28. The method of claim 26 wherein $R^3$ is in the 3-position and $R^4$ is in the 4-position and their salts.

29. The method of claim 20 wherein R and $R^1$ are hydrogen or $C_1$-$C_4$ alkyl; $R^2$ is chlorine, bromine, iodine or $C_1$-$C_4$ alkoxy; $R^3$ is hydrogen, halogen, $C_1$-$C_4$ alkyl, $C_1$-$C_4$ alkoxy, nitro, $C_1$-$C_4$ haloalkyl or $R^bSO_n$ wherein $R^b$ is $C_1$-$C_4$ alkyl and n is the integer 0; $R^4$ is $R^bSO_n-$ wherein $R^b$ is $C_1$-$C_4$ alkyl and n is the integer 2; and $R^5$ is hydrogen and their salts.

30. The method of claim 20 wherein R and $R^1$ are hydrogen or methyl; $R^2$ is chlorine, bromine, iodine or methoxy; $R^3$ is hydrogen, halogen, methyl, methoxy, nitro, trifluoromethyl, or methylthio; $R^4$ is $R^bSO_n-$ wherein $R^b$ is methyl and n is the integer 2; and $R^5$ is hydrogen and their salts.

31. The method of claim 29 wherein $R^3$ is in the 3-position and $R^4$ is in the 4-position and their salts.

32. The method of claim 30 wherein $R^3$ is in the 3-position and $R^4$ is in the 4-position and their salts.

33. The method of claim 20 wherein R is hydrogen, $R^1$ is hydrogen, $R^2$ is chlorine, $R^3$ is hydrogen, $R^4$ is 4-chlorine and $R^5$ is hydrogen and its salts.

34. The method of claim 20 wherein R is hydrogen, $R^1$ is hydrogen, $R^2$ is chlorine, $R^3$ is 3-chlorine, $R^4$ is 4-chlorine and $R^5$ is hydrogen and its salts.

35. The method of claim 20 wherein R is hydrogen, $R^1$ is hydrogen, $R^2$ is chlorine, $R^3$ is hydrogen, $R^4$ is 4-bromine and $R^5$ is hydrogen and its salts.

36. The method of claim 20 wherein R is hydrogen, $R^1$ is hydrogen, $R^2$ is chlorine, $R^3$ is hydrogen, $R^4$ is 4-$CH_3SO_2$ and $R^5$ is hydrogen and its salts.

37. The method of claim 34 wherein the salts are the sodium, isopropylamine, triethylamine and potassium salts.

38. An herbicidal composition comprising an herbicidally active 2-(2-chlorine, bromine, iodine or $C_1$-$C_4$ alkoxy)benzoyl-1,3-cyclohexanedione or its salts and an inert carrier therefor.

39. The herbicidal composition of claim 38 wherein the 2-position of the benzoyl moiety is substituted with chlorine, bromine or $C_1$-$C_4$ alkoxy.

40. The herbicidal composition of claim 39 wherein the 2-position of the benzoyl moiety is substituted with chlorine, bromine or methoxy.

41. The herbicidal composition of claim 38 wherein the 2-position of the benzoyl moiety is substituted with chlorine, bromine or $C_1$-$C_4$ alkoxy and the 5-position of the 1,3-cyclohexanedione moiety is substituted with one or two $C_1$-$C_4$ alkyl groups.

42. The herbicidal composition of claim 38 wherein the 2-position of the benzoyl moiety is substituted with chlorine, bromine, iodine or methoxy and the 5-position of the 1,3-cyclohexanedione moiety is substituted with one or two methyl groups.

43. The compound of claim 1 wherein R is hydrogen, $R^1$ is hydrogen, $R^2$ is chlorine, $R^3$ is 3-chlorine, $R^4$ is 4-$C_2H_5SO_2$, and $R^5$ is hydrogen and its salts.

44. The compound of claim 1 wherein R is hydrogen, $R^1$ is hydrogen, $R^2$ is is chlorine, $R^3$ is 3-methoxy, $R^4$ is 4-$CH_3SO_2$, $R^5$ is hydrogen and its salts.

45. The compound of claim 1 wherein R is hydrogen, $R^1$ is hydrogen, $R^2$ is chlorine, $R^3$ is 3-chlorine, $R^4$ is 4-n-$C_3H_7SO_2$, and $R^5$ is hydrogen and its salts.

46. The compound of claim 1 wherein R is hydrogen, $R^1$ is hydrogen, $R^2$ is chlorine, $R^3$ is 3-methoxy, $R^4$ is 4-bromine and $R^5$ is hydrogen and its salts.

47. The compound of claim 1 wherein R is hydrogen, $R^1$ is hydrogen, $R^2$ is chlorine, $R^3$ is 3-ethoxy, $R^4$ is 4-$C_2H_5SO_2$ and $R^5$ is hydrogen and its salts.

48. The compound of claim 1 wherein R is hydrogen, $R^1$ is hydrogen, $R^2$ is chlorine, $R^3$ is 3-methoxy, $R^4$ is 4-$C_2H_5SO_2$ and $R^5$ is hydrogen and its salts.

49. The compound of claim 1 wherein R is hydrogen, $R^1$ is hydrogen, $R^2$ is chlorine, $R^3$ is 3-n-$C_3H_7O$, $R^4$ is 4-$C_2H_5SO_2$ and $R^5$ is hydrogen and its salts.

50. The compound of claim 1 wherein R is hydrogen, $R^1$ is hydrogen, $R^2$ is chlorine, $R^3$ is 3-n-$C_3H_7O$, $R^4$ is 4-$CH_3SO_2$ and $R^5$ is hydrogen and its salts.

51. The compound of claim 1 wherein R is hydrogen, $R^1$ is hydrogen, $R^2$ is chlorine, $R^3$ is 3-ethylthio, $R^4$ is 4-$C_2H_5SO_2$ and $R^5$ is hydrogen and its salts.

52. The compound of claim 1 wherein R is hydrogen, $R^1$ is hydrogen, $R^2$ is chlorine, $R^3$ is 3-n-$C_4H_9O$, $R^4$ is 4-$C_2H_5SO_2$, and $R^5$ is hydrogen and its salts.

53. The compound of claim 1 wherein R is hydrogen, $R^1$ is hydrogen, $R^2$ is chlorine, $R^3$ is hydrogen, $R^4$ is 4-methylthio, $R^5$ is hydrogen and its salts.

54. The method of claim 20 wherein R is hydrogen, $R^1$ is hydrogen, $R^2$ is chlorine, $R^3$ is 3-chlorine, $R^4$ is 4-$C_2H_5SO_2$ and $R^5$ is hydrogen and its salts.

55. The method of claim 20 wherein R is hydrogen, $R^1$ is hydrogen, $R^2$ is chlorine, $R^3$ is 3-methoxy, $R^4$ is 4-$CH_3SO_2$ and $R^5$ is hydrogen and its salts.

56. The method of claim 20 wherein R is hydrogen, $R^1$ is hydrogen, $R^2$ is chlorine, $R^3$ is 3-chlorine, $R^4$ is 4-n-$C_3H_7SO_2$ and $R^5$ is hydrogen and its salts.

57. The method of claim 20 wherein R is hydrogen, $R^1$ is hydrogen, $R^2$ is chlorine, $R^3$ is 3-methoxy, $R^4$ is 4-bromine and $R^5$ is hydrogen and its salts.

58. The method of claim 20 wherein R is hydrogen, $R^1$ is hydrogen, $R^2$ is chlorine, $R^3$ is 3-ethoxy, $R^4$ is 4-$C_2H_5SO_2$, $R^5$ is hydrogen and its salts.

59. The method of claim 20 wherein R is hydrogen, $R^1$ is hydrogen, $R^2$ is chlorine, $R^3$ is 3-methoxy, $R^4$ is 4-$C_2H_5SO_2$ and $R^5$ is hydrogen and its salts.

60. The method of claim 20 wherein R is hydrogen, $R^1$ is hydrogen, $R^2$ is chlorine, $R^3$ is 3-n-$C_3H_7O$, $R^4$ is 4-$C_2H_5SO_2$ and $R^5$ is hydrogen and its salts.

61. The method of claim 20 wherein R is hydrogen, $R^1$ is hydrogen, $R^2$ is chlorine, $R^3$ is 3-n-$C_3H_7O$, $R^4$ is 4-$CH_3SO_2$ and $R^5$ is hydrogen and its salts.

62. The method of claim 20 wherein R is hydrogen, $R^1$ is hydrogen, $R^2$ is chlorine, $R^3$ is 3-ethylthio, $R^4$ is 4-$C_2H_5SO_2$ and $R^5$ is hydrogen and its salts.

63. The method of claim 20 wherein R is hydrogen, $R^1$ is hydrogen, $R^2$ is chlorine, $R^3$ is 3-n-$C_4H_9O$, $R^4$ is 4-$C_2H_5SO_2$ and $R^5$ is hydrogen and its salts.

64. The method of claim 20 wherein R is hydrogen, $R^1$ is hydrogen, $R^2$ is chlorine, $R^3$ is hydrogen, $R^4$ is 4-methylthio and $R^5$ is hydrogen and its salts.

* * * * *

UNITED STATES PATENT AND TRADEMARK OFFICE
CERTIFICATE OF CORRECTION

PATENT NO. : 4,780,127

DATED : October 25, 1988

INVENTOR(S) : William J. Michaely and Gary W. Kraatz

It is certified that error appears in the above-identified patent and that said Letters Patent is hereby corrected as shown below:

In Column 5, lines 24-29, "═══" should read --- ⇌ ---.

In Column 14, line 34, "RR$^8$" should read ---R$^{48}$---.

In Column 32, line 4, "$H_2SO_4$" should read ---$H_2SO_4$--->.

In Column 77, under heading BSG, Compound No. 114A, "00" should read ---100---.

In Columns 49 and 50, under the heading "R$^{14}$" for Compound No. 78B, the term "4-$(CH_3)_2NHO_2$" should read ---4-$(CH_3)_2NSO_2$---.

In Columns 49 and 50, under the headings "R$^{13}$" and "R$^{14}$" for Compound 19 counting up from the last compound, the terms "4-Cl" and "H" should read ---3-Cl--- and ---4-Cl---, respectively.

UNITED STATES PATENT AND TRADEMARK OFFICE
CERTIFICATE OF CORRECTION

PATENT NO. : 4,780,127

DATED : October 25, 1988

INVENTOR(S) : William J. Michaely and Gary W. Kraatz

It is certified that error appears in the above-identified patent and that said Letters Patent is hereby corrected as shown below:

In Column 1, lines 45-54, Column 3, lines 15-20, Column 3, lines 38-42, Column 5, lines 24-29, Column 5, lines 50-55, Column 15, line 10, Column 17, lines 14-19, Column 17, lines 39-44, Column 19, lines 23-28, add an additional "bond" between the phenyl ring and the carbon atom.

In Column 8, lines 39-44, Column 8, lines 51-54, Column 9, lines 3-8, Column 9, lines 14-19, Column 11, lines 10-15, Column 11, lines 24-29, Column 11, lines 38-43, Column 11, lines 49-54, Column 14, lines 30-35, Column 14, lines 44-49, Column 14, lines 57-62, Column 15, lines 2-7, the two slanted lines between the structural formulae should read --- ⇄ ---.

In Column 9, line 54, Column 11, line 15, Column 25, line 41, the bond between $R^{38}$ and the ring should be inserted.

In Column 15, line 50, the bond between $R^{58}$ and the ring should be inserted.

In Column 23, line 43, the bond between $R^{28}$ and the ring should be inserted.

UNITED STATES PATENT AND TRADEMARK OFFICE
CERTIFICATE OF CORRECTION

PATENT NO. : 4,780,127

DATED : October 25, 1988

INVENTOR(S) : William J. Michaely and Gary W. Kraatz

Page 3 of 3

It is certified that error appears in the above-identified patent and that said Letters Patent is hereby corrected as shown below:

In Column 36, line 67, after the word "reaction" add the word ---product---.

In Column 43, under heading "R" for Compound No. 81A, the term "HB" should read ---H---.

In Column 71, under heading VL, for Compound No. 133A, "35" should read ---85---.

Signed and Sealed this

Twenty-fourth Day of August, 1993

Attest:

BRUCE LEHMAN

*Attesting Officer*    Commissioner of Patents and Trademarks